US007297782B2

(12) United States Patent
Labas et al.

(10) Patent No.: US 7,297,782 B2
(45) Date of Patent: Nov. 20, 2007

(54) CHROMOPHORES/FLUOROPHORES AND METHODS FOR USING THE SAME

(75) Inventors: Yulii Aleksandrovich Labas, Moscow (RU); Nadezda Georgievna Gurskaya, Moscow (RU); Yuriy Yanushevich, Moscow (RU); Arcady Fedorovich Fradkov, Moscow (RU); Konstantin Lukyanov, Moscow (RU); Sergey Lukyanov, Moscow (RU); Mikhail Vladimirovich Matz, Moscow (RU)

(73) Assignee: Clontech Laboratories, Inc., Mountain View, CA (US)

( * ) Notice: Subject to any disclaimer, the term of this patent is extended or adjusted under 35 U.S.C. 154(b) by 360 days.

(21) Appl. No.: 10/757,356

(22) Filed: Jan. 13, 2004

(65) Prior Publication Data
US 2005/0032085 A1    Feb. 10, 2005

Related U.S. Application Data

(63) Continuation-in-part of application No. PCT/US02/36499, filed on Nov. 12, 2002.

(60) Provisional application No. 60/332,980, filed on Nov. 13, 2001.

(51) Int. Cl.
C07H 21/04 (2006.01)
C12N 15/63 (2006.01)
C12N 15/85 (2006.01)

(52) U.S. Cl. .................... 536/23.1; 435/320.1; 435/325
(58) Field of Classification Search ...................... None
See application file for complete search history.

(56) References Cited

U.S. PATENT DOCUMENTS

| | | | |
|---|---|---|---|
| 5,491,084 A | 2/1996 | Chalfie et al. | |
| 5,874,304 A | 2/1999 | Zolotukhin et al. | |
| 5,919,445 A | 7/1999 | Chao | |
| 5,958,713 A | 9/1999 | Thastrup et al. | |
| 5,968,738 A | 10/1999 | Anderson et al. | |
| 5,968,750 A | 10/1999 | Zolotukhin et al. | |
| 5,976,796 A | 11/1999 | Szalay et al. | |
| 5,985,577 A | 11/1999 | Bulinski | |
| 6,020,192 A | 2/2000 | Muzyczka et al. | |
| 6,066,476 A | 5/2000 | Tsien et al. | |
| 6,933,375 B2* | 8/2005 | Falkowski et al. | 536/23.5 |
| 6,969,597 B2* | 11/2005 | Lukyanov et al. | 435/69.1 |

FOREIGN PATENT DOCUMENTS

| | | |
|---|---|---|
| DE | 197 18 640 A1 | 7/1999 |
| WO | WO 99/49019 | 9/1999 |
| WO | WO 00/46233 | 8/2000 |
| WO | WO 01/27150 | 4/2001 |

OTHER PUBLICATIONS

Carter et al, Comparative Biochemistry and Physiology, Part C 138:259-270, 2004.*
Lesser et al, GenBank Accession AF406766, 2001.*
Singh et al, Journal of Virological Methods, 86:121-129, 2000.*
Anderluh et al. "Cloning, Sequencing, and Expression of Equinatoxin II" *Biochemical and Biophysical Research Communications*, (1996) 220:437-442.
Dove et al. "Isolation and Partial Characterization of the Pink and Blue Pigments of Pocilloporid and Acroporid Corals" *Biological Bulletin*, (1995) 189:288-297.
Fradkov et al. "Novel Fluorescent Protein from Discosoma Coral and its Mutants Possesses a Unique Far-Red Fluorescence" *FEBS Letters* (2000) 479:127-130.
Gurskaya et al. "GFP-Like Chromoproteins as a Source of Far-Red Fluorescent Proteins" *FEBS Letters* (2001) 507:16-20.
Gurskaya et al. "Color Transitions in Coral's Fluorescent Proteins by Site-Directed Mutagenesis" *BMC Biochemistry* (2001) 2:6.
Lukyanov et al. "Natural Animal Coloration Can be Determined by a Nonfluorescent Green Fluorescent Protein Homolog" *The Journal of Biological Chemistry* (2000) 275:25879-25882.
Macek et al. "Intrinsic Tryptophan Fluorescence of Equinatoxin II, a Pore-Forming Polypeptide from the Sea Anemone *Actinia equina* L, Monitors its Interaction with Lipid Membranes" *Eur. J. Biochemistry* (1995) 234:329-335.
Martynov et al. "Alternative Cyclization in GFP-Like Proteins Family" *The Journal of Biological Chemistry* (2001) 276:21012-21016.
Matz et al. "Fluorescent Proteins from Nonbioluminescent Anthozoa Species" *Nature Biotechnology*, (1999) 17:969-973.

(Continued)

*Primary Examiner*—Peter Paras, Jr.
*Assistant Examiner*—David A. Montanari
(74) *Attorney, Agent, or Firm*—Bret E. Field; David C. Scherer; Bozicevic, Field & Francis LLP

(57) ABSTRACT

Nucleic acid compositions encoding novel chromo/fluoroproteins and mutants thereof, as well as the proteins encoded the same, are provided. The proteins of interest are proteins that are colored and/or fluorescent, where this feature arises from the interaction of two or more residues of the protein. The subject proteins are further characterized in that they are either obtained from non-bioluminescent *Cnidarian*, e.g., *Anthozoan*, species or are obtained from *Anthozoan* non-*Pennatulacean* (sea pen) species. Specific proteins of interest include the following specific proteins: hcriGFP; dendGFP; zoanRFP; scubGFP1; scubGFP2; rfloRFP; rfloGFP; mcavRFP; mcavGFP; cgigGFP; afraGFP; rfloGFP2; mcavGFP2; and mannFP. Also of interest are proteins that are substantially similar to, or mutants of, the above specific proteins. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

10 Claims, 26 Drawing Sheets

OTHER PUBLICATIONS

Terskikh et al. "Fluorescent Timer": Protein that Changes Color with Time *SCIENCE* (2000) 290:1585-1588.

Tsien "The Green Fluorescent Protein" *Annu Rev. Biochem.* (1998) 67:509-44.

Tsien "Rosy Dawn for Fluorescent Proteins" *Nature Biotechnology* (1999) 17:956-957.

Ward et al. "An Energy Transfer Protein in Coelenterate Bioluminescence" *The Journal of Biological Chemistry* (1979) 254:781-788.

Yarbrough et al. "Refined Crystal Structure of DsRed, a Red Fluorescent Protein from Coral, at 2.0-Å Resolution" Proc. Nat'l Acad. Sci. (2001) 98:462-467.

Wiedenmann et al. "Cracks in the β-can: Fluorescent Proteins From Anemonia Sulcata (Anthozoa, Actinaria)," (2000), PNAS, 97(26):14091-14096.

Labas et al. "Diversity and Evolution of the Green Fluorescent Protein Family," (2002) PNAS 99(7):4256-4261.

\* cited by examiner

FIG. 4A

| Protein ID (original ID) | GenBank accession # | Reference |
|---|---|---|
| amajGFP (amFP486)<br>dstrGFP (dsFP483)<br>clavGFP (cFP484) | AF168421<br>AF168420<br>AF168424 | 2<br>2<br>2 |
| GFP<br>cgigGFP<br>hcriGFP | M62653<br>AY037776<br>AF420592 | 34<br>this paper<br>this paper |
| ptilGFP<br>rmulGFP<br>zoanGFP (zFP506)<br>asulGFP (asFP499)<br>dis3GFP<br>dendGFP<br>mcavGFP<br>rfloGFP<br>scubGFP1<br>scubGFP2 | AY015995<br>AY015996<br>AF168422<br>AF322221<br>AF420593<br>AF420591<br>AY037769<br>AY037772<br>AY037767<br>AY037771 | 35<br>35<br>2<br>4<br>this paper<br>this paper<br>this paper<br>this paper<br>this paper<br>this paper |
| zoanYFP (zFP538) | AF168423 | 2 |
| DsRed (drFP583)<br>dis2RFP (dsFP593)<br>zoan2RFP | AF168419<br>AF272711<br>AY059642 | 2<br>36<br>this paper |
| mcavRFP<br>rfloRFP | AY037770<br>AY037773 | this paper<br>this paper |
| asulCP (asCP) | AF246709 | 3, 4 |
| hcriCP (hcCP)<br>cgigCP (cgCP)<br>cpasCP (cgCP)<br>gtenCP (gtCP) | AF363776<br>AF363775<br>AF383155<br>AF383156 | 5<br>5<br>5<br>5 |

FIG. 4B

| |
|---|
| Taxonomy<br>*Genus species* (Class, Sub-class, Order) |
| *Anemonia majano* (Anthozoa, Zoantharia, Actiniaria)<br>*Discosoma striata* (Anthozoa, Zoantharia, Corallimorpharia)<br>*Clavularia sp.* (Anthozoa, Alcyonaria, Alcyonacea) |
| *Aequorea victoria* (Hydrozoa,......, Hydroida)<br>*Condylactis gigantea* (Anthozoa, Zoantharia, Actiniaria)<br>*Heteractis crispa* (Anthozoa, Zoantharia, Actiniaria) |
| *Ptilosarcus sp.* (Anthozoa, Alcyonaria, Pennatulacea)<br>*Renilla muelleri* (Anthozoa, Alcyonaria, Pennatulacea)<br>*Zoanthus sp.* (Anthozoa, Alcyonaria, Zoanthidea)<br>*Anemonia sulcata* (Anthozoa, Zoantharia, Actiniaria)<br>*Discosoma sp.3* (Anthozoa, Zoantharia, Corallimorpharia)<br>*Dendronephthya sp.* (Anthozoa, Alcyonaria, Alcyonacea)<br>*Montastraea cavernosa* (Anthozoa, Zoantharia, Scleractinia)<br>*Ricordea florida* (Anthozoa, Zoantharia, Corallimorpharia)<br>*Scolymia cubensis* (Anthozoa, Zoantharia, Scleractinia)<br>*Scolymia cubensis* (Anthozoa, Zoantharia, Scleractinia) |
| *Zoanthus sp.* (Anthozoa, Zoantharia, Zoanthidea) |
| *Discosoma sp.1* (Anthozoa, Zoantharia, Corallimorpharia)<br>*Discosoma sp.2* (Anthozoa, Zoantharia, Corallimorpharia)<br>*Zoanthus sp.2* (Anthozoa, Zoantharia, Zoanthidea) |
| *Montastraea cavernosa* (Anthozoa, Zoantharia, Scleractinia)<br>*Ricordea florida* (Anthozoa, Zoantharia, Corallimorpharia) |
| *Anemonia sulcata* (Anthozoa, Zoantharia, Actiniaria) |
| *Heteractis crispa* (Anthozoa, Zoantharia, Actiniaria)<br>*Condylactis gigantea* (Anthozoa, Zoantharia, Actiniaria)<br>*Condylactis passiflora* (Anthozoa, Zoantharia, Actiniaria)<br>*Goniopora tenuidens* (Anthozoa, Zoantharia, Scleractinia) |

| color | Representative chromophore structure |
|---|---|
| GREEN | GFP:  |
| YELLOW | ? |
| ORANGE-RED | DsRed:  |
| | ? |
| PURPLE-BLUE | asulCP:  |
| | ? |

FIG. 5

Table 2

| clade | colors | Zoantharia orders |
|---|---|---|
| A | Green, purple-blue | Actiniaria |
| B | Green, orange-red, purple-blue | Corallimorpharia, Scleractinia |
| C | Green, yellow, orange-red | Actiniaria, Zoanthidea |
| D | Green, orange-red | Corallimorpharia, Scleractinia |

FIG. 7A

```
                         10              20              30              40              50              60
GFP           :                                                                                                   :
rmulGFP       : ----MSKGEELFTG-VVPILVELDGDVNGHKFSVSGEGEGDAITYGKLTLKFICTT-GKLPVP--WPTLVTTFSYG :  67
ptilGFP       : ------MSKQILKNTCLQE-VMSYKVNLEGIVNNHVFTMEGCGKGNILFGNQLVQIRVT--KGAPLPFAFDIVSPAFQYG :  71
asulGFP       : ----MNRNVLKNTGLKE-IMSAKASVEGIVNNHVFSMEGFGKGNVLFGNQIMQIRVT--EGAPLPFAFDIVSIAFQYG :  71
hcriCP        : ---------MASFLKK-TMPFKITIEGTVNGHYFKCTGKGEGNPFTGTQSMRIHVT--EGGPLPFAFHILSTSCMYG :  65
cgigCP        : --------MAGLLKE-SMRIKMYMEGTVNGHYFKCEGEGDGNPFTGTQSMRIHVT--EGAPLPFAFDILAPCCEYG :  65
cpasCP        : --------MAGLLKE-SMRIKIYMEGTVNGHYFKCEGEGDGNPFTGTQNMRIRVT--EGAPLPFAFDILSPCCAYG :  65
asulGFP       : --------MAGLLKE-SMRIKIYMEGTVNGHYHFKCEGEGDGNPYEGTQNMRIRVT--EGAPLPFAFDILSPCCAYG :  65
cgigGFP       : --------MYPSIKE-TMRVQLSMEGSVNYAAPKCTGKGEGKPYEGTQSLNITIT--EGGPLPFAFDILSHAFQYG :  65
cgigGFP       : --------MYPWIKE-TMRSKVYMEGDVNNHAFKCTAVGEGKPYKGSQDLITITVT--EGGPLPFAFDILSHAFQYG :  65
hcriGFP       : --------MCSYIKE-TMQSKVYMEGKVNDHNFKCTAEGKGEPYKGSQSLITITVT--EGGPLPFAFDILSHAFRYG :  65
aaspFFP       : --------MSVIAK-QMTYKVYMSGTVNGHYFEVEGDGKG-PYEGEQTVRLTVT--KGGPLPFAWDILSPQSQYG :  63
gtenCP        : --------MSVIAK-QMTYKVYMSGTVNGHYFEVQGDGKGKPYEGEQTVRLTVT--KGGPLPFTAWDILSPQSQIG :  64
dstrGFP       : --------MCSKSVIKE-EMLIDLHLEGTFNGHYFEIKGKGKGQPNEGTINTVTLEVT--KGGPLPFGWHILCPQFQYG :  68
DsRed         : --------MRSSKNVIKE-FMRFKVRMEGTVNGHEFELEGEGEGRPYEGHNTVKLKVT--KGGPLPFAWDILSPQFQYG :  68
dis2RFP       : --------MSCSKNVIKE-FMRFKVRMEGTVNGHEFEIKGEGEGRPYEGHCSVKLMVT--KGGPLPFAFDILSPQFQYG :  68
amajGFP       : --------MALSNKFIGD-DMRMTYHMDGCVNGHYFTVKGEGNGKPYEGTQTSFKVTMANGGPLAFSFDILSTVFKYG :  70
zoanGFP       : --------MAQSKHGLIK-EMTMKYHMEGCVNGHKFVITGEGIGYPFKGKQAINLCVV--EGGPLPFAEDILSAAFNYG :  68
zoanYFP       : --------MAHSKHGLIE-EMTMKYHMEGCVNGHKFVITGESIGYPFKGKQTINLCVI--EGGPLPFSEDILSAGFKYG :  68
zoan2RFP      : --------MAHSKHGLID-DMIMHFRMEGCVDGHKFVIEGNGNPFKGKQFINLCVI--EGGPLPFSEDILSAATDYG :  68
rfloRFP       : --------MSALKE-EMKIKLTLVGVVNGHPFKIIGDGKGKPYEGTQTLAVV--EGGPLPFSYDILTTVHYG :  64
rfloGFP       : --------MSALKE-EMKIKLKNVGVVNGQSFQIDGEGKGKPYEGSQKLTLEVV--KGGPLLFSYDILTTIFQYG :  64
dis3GFP       : --------MSALKE-YMKINIIMEGVVNGLPFKIRGDGKGKPYQGSQEITITVV--KGGPLPFSYDILTTMFQYG :  64
scubGFP1      : --------MQRAGMKVKE-HMKIKLRMGGTVNGKHFAVNGTEDGYPYQGKQILKLIVE--GSEPLPFAFDILSAAFQYG :  68
scubGFP2      : --------MQSAGKKNVKD-FMRITLRMDGAVNGRPFAVNGTEDGNPYGIQSLKLTVD--GNKPLPFAFDILSAAFQYG :  70
mcavRFP       : --------MSVIKS-VMKIKLRMEGSVNGHNFVTVGEGEGKPYEGTQSMDLTVK--EGAPLPFAYDIMTTVFHYG :  64
mcavGFP       : --------MTSVAQEKGVIKP-DMRMKLRMEGAVNGHKFVVEGDGKGKPFDGTQTMDLTVI--EGAPLPFAYDILTTVFDYG :  71
dendGFP       : --------MNLIKE-DMRVKVHMEGNVNGHAFVLEGEGKGRPYEGTQTLNLITVK--EGAPLPFSYDILTTALHYG :  64
clavGFP       : MKCKFVFCLSFLVLAITNANIFLRNEADLEEKTLRIPKALTTMGVIKPDMKIKLKMEGNVNGHAFVIEGEGEGKPYDGTHTLNLEVK--EGAPLPFSYDILSNAFQYG :  106

6  6 G vlgh F    gGGpG q             g P6pf  di6            YG
```

FIG. 7B

```
              70         80         90        100        110        120        130        140        150        160
GFP       : VQCFSRYPDHMKQHDFFKSAM---PEGYVQERTIFYKDDGNYKSRAEVKFEGD---TLVNRIELKGIDFKEDGNILGHKMEYNYNSHNVYIMADKQKNGIKVNFKIRH : 169
rmulGFP   : NRIFTKYPNDIS--DYFIQSF---PAGFMYERTLRYEDGGLVEIRSDINLIED---KFVVRVEYKGSNFPDDGPVM-QKTILGIEPSFEAMYM--NNGVLVGEVILVY : 168
ptilGFP   : NRIFTKYPDDIA--DYFVQSF---PAGFFYERNLRFEDGAIVDIRSDISLEDD---KFHYKVEYRGNGFPPSNGPVM-QKAILGMEPSFEVVYM--NSGVLNGEVDLVY : 168
asulGFP   : SKTFIKVVSGIP--DYFKQSF---PEGFTWERTTTYEDCGFLTAHQDTSLDGD---CLVFKVKILGMNFPADGPVM-QNKAGRWEPATEIVEE--VDGVLRGQSIMAL : 162
hcriCP    : SRTFVIHTAEIP--DFFKQSF---PEGFTWERTTTYEDGGILTAHQDTSLEGN---CLIYKVKVLGTNFPADGPVM-KNRSGGWEPCTEVVVP--ENGVLCGRNVMAL : 162
cgigCP    : SKTFIKTSGIP--DYFKQSF---PEGFTWERTTTIYEDGGVLTAHQDTSLEGN---CLIYKVKVLGTNFPADGPVM-KKISGGWEPCTEIVYQ--DNGVLRGRNVMAL : 162
cpasCP    : SKTFIKTSGIP--DYFKQSF---PEGFTWERTTTYEDGGVLTAHQDTSLEGN---CLNYKVKVLGTNFPADGPVM-KNLSGGWEPCTEIVYQ--DNGVLRGRNVMAL : 162
asulGFP   : IKVFAKYPKEIP--DFFKQSL---PDGFSWERVSTYEDGGVLSATQETSLQGD---CIICKVKVLGTNFPADGPVM-QKKTCGWEPSTETVIP--RDGGLILRDTPAL : 162
cgigGFP   : NKVFIDYPDDIP--DFFKQSL---SDGFTWRRVSNYDDGGVLTVTQDTSLKGD---CIICNIKVHGTNFPPENGPVM-QMKTDGWEPSTETVIP--QDGGIVAARSPAL : 162
hcriGFP   : NKVFAKYPKDHP--DFFKQSL---PEGFTWERVSNYEDGGVLTVKQETSLEGD---CIICKIKAHGTNFPADGPVM-QKRTNGWEPSTETVIP--RGGGILMRDVPAL : 162
aaspFP    : SIPFTKYPEDIP--DYVKQSF---PEGYTWERIMNFEDGAVCTVSND-SIQGN---CFIYHVKFSGLNFPPNGPVM-QKKTQGWEPNTERLFA--RDGMLIGNNFMAL : 159
gtenCP    : SIPFTKYPEDIP--DYVKQSF---PEGYTWERIMNFEDGAVCTVSNDSSIQGN---CFIYNVKFSGLNFPPNGPVM-QKKTQGWEPNTERLFA--RDGMLIGNNFMAL : 161
dstrGFP   : NKAFVHPDNTH--DYLKLSF---PEGYTWERSMHFEDGGLLCCITNSIDLTGN---CFYDIKFTGLNFPPNGPVV-QKKTTGWEPSTERLYP--RDGVLIGDIHHAL : 165
DsRed     : SKVYVKHPADIP--DYKKLSF---PEGFKWERVMNFEDGGVTVTVIQDSSLQDG---CFIYEVKFIGVNFPSDGPVM-QKKIMGWEASTERLYP--RDGVLKGEIHKAL : 165
dis2RFP   : SKVYVKHPADIP--DYKKLSF---PEGFKWERVMNFEDGGVTVSQDSSLKDG---CFIYEVKFIGVNFPSDGPVM-QRRTRGWEPSSERLYP--RDGVLKGDIHMAI : 165
amajGFP   : NRCFTAYPTSMP--DYFKQAF---PDGMSYERTFTYEDGGVATASWEISLKGN---CFEHKSTFHGVNFPADGPVM-AKKTTGWDPSFEKMTV--CDGILKGDVTAFL : 167
zoanGFP   : NRVFTEYPQDIV--DYFKNSC---PAGYTNDRSFLFEDGAVCICNADITVSVE-ENCMYIESKPYGVNFPADGPVM-KKMTDNWEPSCEKIIPVPKGILKGDVSMYL : 169
zoan2GFP  : DRIFTEYPQDIV--DYFKNSC---PAGYTWGRSFLFEDGAVCICNVDITVSVK-ENCIYHKSIFNGMNFPADGPVM-KKMTINWEASCEKIMPVPKQGILKGDVSMYL : 169
zoan2RFP  : NRLFTEYPEGIV--DYFKNSC---PAGYTWHRSFRFEDGAVCICSADITVNVR-ENCIYHESTFYGVNFPADGPVM-KKMTTNMEPSCEKIIPINSQKILKGDVSMYL : 169
rfloRFP   : NRAFVNYPKDIP--DIFKQTCSGPEGAGYSWQRTMSFEDGGVCTATSHIRVDGD---TFNYDIHFMGADFPLNGPVM-QKRITVKWEPSTEIMFQ--CDGLLRGDVAMSL : 164
rfloGFP   : NRAFVNYPKDIP--DIFKQTCSGPDGGFSWQRTMTYEDGGVCTASNHISVDGD---TFYVIRFNGENFPPNGPVM-QKRTVKWEPSTEIMFE--RDGLLRGDIAMSL : 164
dis3GFP   : NRAFVNYPEDIP--DIFKQTCSGPNGGYSWQRTMTYEDGGVCTATSNISVVGD---TFNYDIHFMGANFPLDGPMM-QKRTMKWEPSTEIMFE--RDGLLRGDIAMSL : 164
scubGFP1  : NRAFTEYPTEIA--DYFKQSFEF-GEGFSWERSFTFEDGAICVATNDITMVGG---EFQYDIRFDGLNFPEDGPVM-QKKTVKWEPSTEIMZM--QNGVLKGEVNMAL : 167
scubGFP2  : NRAFTEYPKEIS--DYFKQSFEF-GEGFTWGRSFTFEDGAICVATNDIKMVGD---EFQYNTRFDGVNFPEDGPVM-QKKTVKWEPSTEIMRV--QGGVLKGEVNMAL : 169
mcavRFP   : NRVFAKYPKHIP--DYFKQVF---PEGYSWERSMFEDGGICTARNEITMEGD---CFFNKVRFDGVNFPPNGPVM-QKKTLKWEPSTEKMYV--RDGVLTGDINMAL : 161
mcavGFP   : NRVFAKYPEDIA--DYFKQTF---PEGYFWERSMTYEDQGICTATNDITMMEGVDDCFAYKIRFDGVNFPANGPVM-QRKTILKWEPSTEIMYA--RDGVLKGDVNMAL : 171
dendGFP   : NRVFTEYPADIT--DYFKQSF---PEGYSWERTMTYEDKGICTIRSDISLEGD---CFQNIRFNGMNFPPNGPVM-QKKTLKWEPSTEKLHV--RDGLLVGNINMAL : 161
clavGFP   : NRALTKYPDDIA--DYFKQSF---PEGYSWERTMTFEDKGIVKVKSDISMEED----SFTYEIRFDGWNFPPNGPVM-QKKTLKWEPSTEIMYV--RDGVLVGDISHSL : 203 yp    D fk    pG    R   5cDg                                 G  Fp 1Gp66        ep e 6              g 9
```

FIG. 7C

```
              170        180        190        200        210        220        230
GFP      : NIEDG-SVQLADHYQQNTPIGDG-PVLLPDNHYLSTQSALSKDPNEKRDHMILLEFVTAAGITHGMDELYK------- : 238
rmulGFP  : KLNSG-KYYSCHMKTLMKSKGV--VKEFPSYHFIQHRLEKTYVEDGG--FVEQHETAIAQMTSIGKPLGSLHEWV---- : 238
ptilGFP  : KLESG-NYYSCHMKTFYRSKGG---VKEFPEYHFIHHRLEKTYVEEGS--FVEQHETAIAQLTTIGKPLGSLHEWV--- : 238
asulGFP  : KCPGG-RHLTCHLHTTYRSKKPASALKMPGFHFEDHRIEIMEEVEKGK-CYKQYEAAVGRYCDAAPSKLGHN------- : 232
hcriCP   : KVGDR--RLICHLYTSYRSKKAVRALTMPGFHFTDIRLQMPRKKDE---YFELYEASVARYSDLPEKAN---------- : 227
cgigCP   : KVSGR-PPLICHLHSTYRSKK-ACALTMPGFHFADLRIQMPKKKKDE--YFELYEASVARYSDVPEKAT---------- : 227
cpasCP   : KVSGR-PPLICHLHSTYRSKK-ACALTMPGFHFADLRIQMPKKKKDE--YFELYEASVARYSDLPEKAN---------- : 227
asulGFP  : MLADG-GHLSCFMETTYKSKK---EVKLPELHFHHLRMEKLNISDDWK-TVEQHESVVASYSQVPSKLGHN-------- : 228
cgigGFP  : RLRDK-GHLICHMETTYKPNK---EVKLPELHFHHLRMEKLSVSDDGK-TIKQHEYVVASYSKVPSKIGRQW------- : 229
hcriGFP  : KLLGNKGHLLCVMETTYKSKK---KVNLPKPHFHHLRMEKDSVSDDEK-TIEQHENVRASYFNDSGK------------ : 225
aasp?FP  : KLEGG-GHYLCEFKSTYKAKK---PVRMPGYHYVDRKLDVTNHNKDYT-SVEQCEISIARKPVVA-------------- : 219
gtenCP   : KLEGG-GHYLCEFKSTYKAKK---PVRMPGYHYVDRKLDVTNHNIDYT-SVEQCEISIARKPVVA-------------- : 221
dstrGFP  : TVEGG-GHYACDIKTVYRAKKA--ALKMPGYHYVDTKLVIWNNDKEFM-KVEEHEIAVARHHPFYEPKKDK-------- : 232
DsRed    : RLKDG-GHYLVEFKSIYMAKK---PVQLPGYYYVDSKLDITSHNEDYT-IVEQYERTEGRHHLFL-------------- : 225
dis2RFP  : RLEGG-GHYLVEFKSIYMVKK---PSVQLPGYYYVDSKLDMTSHNEDYT-VVEQYEKTQGRHHPFIKPL----------- : 229
amajGFP  : MLQGG-GNYRCQFHTSYKIKK---PVTMPPNHVEHRIARTDLDKGGN-SVQLTEHAVAHITSVF--PF----------- : 229
zoanGFP  : LLKDG-GRLRCQFDTVYKAKSV--PRIMPDWHFIQHKLTREDRSDAKNQKMHLTEHATASGSALP------------- : 231
zoanYFP  : LLKDG-GRYRCQFDTVYKAKSV--PSKMPEWHFIQHKLLREDRSDAKNQKMQLTEHAIAFPSALA------------- : 231
zoan2RFP : LLKDG-GRYRCQFDTIYKAKTE--PKEMPDWHFIQHKLNREDRSDAKNQKWQLIEHAIASRSALP------------- : 231
rfloRFP  : LLKGG-GHYRCDFKTIYKPKK---NVIKMPGYHFVDHCIEITSQQDDYN-VVELYEGAVAHYSPLQKPCQAKA------ : 231
rfloGFP  : LLKGG-GHYRCDFKTIYTPKR---KVNMPGYHYFVDHCIEIQKHDKDYN-MAVLSEDAVAHNSPLEKKSQAKA------ : 231
dis3GFP  : LLKGG-GHYRCDFETIYKPNK---VVKMPDYHFVDHYIEITSQQNYYN-VVELTEVAEARYSSLEKIGKSKA------ : 231
scubGFP1 : LLQDK-SHYRCDLKTTYKAKNNVP--HPPGYHYVDHCIETLEERKDH---VKLREHAKARSSLSPTSAKERKA----- : 234
scubGFP2 : LLKDK-SHYRCDFKTTYKAKNPVPPTALPDYHYVDHCIETEENRDY---VNLQEYAKARSGLHLPELQK--------- : 235
mcavRFP  : LLEGG-GHYRCDFRTTYRAKKK---GVKLPDYHFVDHSIEILRHDKEYT-EVKLYEHAEAHSGLPRGQRKA-------- : 227
mcavGFP  : LLEGG-GHYLCDFKTTYKAKK----VVRLPDYHFVDHRIEIVSHDKDYN-KVKLHEHAEARHGLSRKAK--------- : 234
dendGFP  : LLEGG-GHYLCDFKTTYKAKK---VVQLPDYHFVDHRIEILSNDSDYN-KVKLYEHGVARYSPLPKSGLVEVQGKAIMTA : 236
clavGFP  : LLEGG-GHYRCDFKSIYKAKK---VVKLPDYHFVDHRIEILNHDKDYN-KVTLYENAVARYSLL--PSQA--------- : 266
                 c    y  k                  P   h                  E        a
```

FIG. 8

Green fluorescent protein from *Heteractis crispa* hcriGFP

```
          10        20        30        40        50        60
ATTTTGGACAGGTGTTCAACCAAGCAAATTTAAGAAGTCATCATCTTTATCTCAGTCAGG 70        80        90       100       110       120
AAAATGTGTTCTTACATCAAAGAAACCATGCAAAGTAAGGTTTACATGGAAGGAAAAGTT
     M   C   S   Y   I   K   E   T   M   Q   S   K   V   Y   M   E   G   K   V 130       140       150       160       170       180
AACGACCACAACTTCAAGTGCACTGCAGAAGGAAAAGGAGAACCATACAAAGGCTCACAA
 N   D   H   N   F   K   C   T   A   E   G   K   G   E   P   Y   K   G   S   Q 190       200       210       220       230       240
AGCCTGACGATCACCGTAACTGAAGGAGGTCCTCTGCCATTTGCCTTCGACATTCTTTCA
 S   L   T   I   T   V   T   E   G   G   P   L   P   F   A   F   D   I   L   S 250       260       270       280       290       300
CACGCCTTTCGATATGGCAATAAGGTGTTCGCCAAGTACCCCAAAGATCATCCTGATTTT
 H   A   F   R   Y   G   N   K   V   F   A   K   Y   P   K   D   H   P   D   F 310       320       330       340       350       360
TTTAAGCAGTCTCTTCCTGAAGGTTTTACTTGGGAAAGAGTAAGCAACTATGAGGACGGA
 F   K   Q   S   L   P   E   G   F   T   W   E   R   V   S   N   Y   E   D   G 370       380       390       400       410       420
GGAGTCCTTACCGTTAAACAAGAAACTAGTCTGGAGGGAGATTGCATTATTTGCAAAATT
 G   V   L   T   V   K   Q   E   T   S   L   E   G   D   C   I   I   C   K   I 430       440       450       460       470       480
AAAGCACATGGCACTAACTTCCCCGCAGATGGTCCGGTGATGCAAAAACGGACCAATGGA
 K   A   H   G   T   N   F   P   A   D   G   P   V   M   Q   K   R   T   N   G 490       500       510       520       530       540
TGGGAGCCATCAACTGAAACGGTTATTCCACGGGGTGGAGGAATTCTGATGCGCGATGTG
 W   E   P   S   T   E   T   V   I   P   R   G   G   G   I   L   M   R   D   V 550       560       570       580       590       600
CCCGCACTGAAGCTGCTTGGTAACAAAGGACATCTTCTCTGCGTCATGGAAACAACTTAC
 P   A   L   K   L   L   G   N   K   G   H   L   L   C   V   M   E   T   T   Y 610       620       630       640       650       660
AAGTCAAAAAAAAAAGGTGAACCTGCCAAACCGCACTTTCATCATTTGAGAATGGAGAAG
 K   S   K   K   K   G   E   P   A   K   P   H   F   H   H   L   R   M   E   K 670       680       690       700       710       720
GATAGTGTTAGTGACGATGAGAAGACCATTGAGCAGCACGAGAATGTGAGGGCAAGCTAC
 D   S   V   S   D   D   E   K   T   I   E   Q   H   E   N   V   R   A   S   Y 730       740       750       760       770       780
TTCAATGATAGTGGAAAATGATCATTTCCTTATTGATTTCAATGTTAGGGCATTCAGTTT
 F   N   D   S   G   K   *

790       800       810       820       830       840
CCAAATTTTCTTAGACACAGTCTTTTCCTTTAGCTTCGTAGCCTACTTACCCATGTTTTG 850       860
TTGAAGTCAATAAATAGCTAAGCACTAC      (SEQ ID NOS: 01 & 02)
```

FIG. 9

Green fluorescent protein from *Dendronephthya sp.* dendGFP

```
            10         20         30         40         50         60
5' CATATCGAGAAAGTTGTGAAACCAAATTCTTACTCTACTTTTACTACCATGAATCTGATT
                                                       M  N  L  I 70         80         90        100        110        120
   AAAGAAGATATGAGGGTTAAGGTGCATATGGAAGGGAATGTAAACGGGCATGCTTTTGTG
   K  E  D  M  R  V  K  V  H  M  E  G  N  V  N  G  H  A  F  V 130        140        150        160        170        180
   ATTGAAGGGGAAGGAAAAGGAAGGCCCTACGAAGGGACACAGACCTTGAACCTGACAGTG
   I  E  G  E  G  K  G  R  P  Y  E  G  T  Q  T  L  N  L  T  V 190        200        210        220        230        240
   AAAGAAGGCGCGCCTCTCCCATTTTCTTACGACATCTTGACAACAGCATTGCACTACGGA
   K  E  G  A  P  L  P  F  S  Y  D  I  L  T  T  A  L  H  Y  G 250        260        270        280        290        300
   AACAGAGTATTCACTGAATACCCAGCAGATATCACGGATTATTTCAAGCAATCATTTCCT
   N  R  V  F  T  E  Y  P  A  D  I  T  D  Y  F  K  Q  S  F  P 310        320        330        340        350        360
   GAAGGATATTCCTGGGAAAGAACCATGACTTATGAAGACAAGGGCATTTGTACCATCAGA
   E  G  Y  S  W  E  R  T  M  T  Y  E  D  K  G  I  C  T  I  R 370        380        390        400        410        420
   AGCGACATAAGCTTGGAAGGTGACTGCTTTTTCCAAAACATTCGTTTTAATGGGATGAAC
   S  D  I  S  L  E  G  D  C  F  F  Q  N  I  R  F  N  G  M  N 430        440        450        460        470        480
   TTTCCCCCAAATGGTCCAGTTATGCAGAAGAAAACTTTGAAGTGGGAACCATCCACAGAG
   F  P  P  N  G  P  V  M  Q  K  K  T  L  K  W  E  P  S  T  E 490        500        510        520        530        540
   AAGCTGCACGTGCGTGATGGGTTGCTTGTCGGTAATATTAACATGGCTCTGCTGCTTGAA
   K  L  H  V  R  D  G  L  L  V  G  N  I  N  M  A  L  L  L  E 550        560        570        580        590        600
   GGAGGTGGACATTACCTGTGTGACTTCAAAACTACTTACAAAGCGAAGAAGGTTGTTCAG
   G  G  G  H  Y  L  C  D  F  K  T  T  Y  K  A  K  K  V  V  Q 610        620        630        640        650        660
   TTGCCAGATTATCATTTTGTGGACCATCGCATTGAGATCTTGAGTAATGACAGCGATTAC
   L  P  D  Y  H  F  V  D  H  R  I  E  I  L  S  N  D  S  Y 670        680        690        700        710        720
   AACAAAGTGAAGCTGTACGAGCATGGGGTTGCTCGCTATTCTCCGTTGCCCAAGTCAGGC
   N  K  V  K  L  Y  E  H  G  V  A  R  Y  S  P  L  P  K  S  G 730        740        750        760        770        780
   CTGGTAGAGGTTCAAGGGAAAGCCATAATGACTGCATAGATAAACATGTAGTGAAGACCA
   L  V  E  V  Q  G  K  A  I  M  T  A  *

790        800        810        820        830        840
   CATACTCGGGATTAGAGTTTAGGGATTGGTAGTTGTGGTAGATTCTAGCCTACAAATTTT
```

TTGGG 3' (SEQ ID NO:03 & 04)

FIG. 10

Red fluorescent protein from *Zoanthus sp.* zoanRFP

```
         10        20        30        40        50        60
GAGTTGAGTTCTCGACTTCAGTTGTATCACTTTTGACGTATCAAGTGATCTATTCTCAAC 70        80        90       100       110       120
ATGGCCCATTCAAAGCACGGACTAACAGATGACATGACAATGCATTTCCGTATGGAAGGG
 M  A  H  S  K  H  G  L  T  D  D  M  T  M  H  F  R  M  E  G 130       140       150       160       170       180
TGCGTCGATGGACATAAGTTTGTAATCGAGGGCAACGGCAATGGAAATCCTTTCAAAGGG
 C  V  D  G  H  K  F  V  I  E  G  N  G  N  G  N  P  F  K  G 190       200       210       220       230       240
AAACAGTTTATTAATCTGTGTGTGATTGAAGGAGGACCACTGCCATTCTCCGAAGACATA
 K  Q  F  I  N  L  C  V  I  E  G  G  P  L  P  F  S  E  D  I 250       260       270       280       290       300
TTGTCTGCTGCGTTTGACTACGGAAACAGGCTCTTCACTGAATATCCTGAAGGCATAGTT
 L  S  A  A  F  D  Y  G  N  R  L  F  T  E  Y  P  E  G  I  V 310       320       330       340       350       360
GACTATTTCAAGAACTCGTGTCCTGCTGGATATACGTGGCACAGGTCTTTTCGCTTTGAA
 D  Y  F  K  N  S  C  P  A  G  Y  T  W  H  R  S  F  R  F  E 370       380       390       400       410       420
GATGGAGCAGTTTGCATATGCAGTGCAGATATAACAGTAAATGTTAGGGAAAACTGCATT
 D  G  A  V  C  I  C  S  A  D  I  T  V  N  V  R  E  N  C  I 430       440       450       460       470       480
TATCATGAGTCCACGTTTTATGGAGTGAACTTTCCTGCTGATGGACCTGTGATGAAAAAG
 Y  H  E  S  T  F  Y  G  V  N  F  P  A  D  G  P  V  M  K  K 490       500       510       520       530       540
ATGACAACTAATTGGGAACCGTCCTGCGAGAAAATCATACCAATAAATAGTCAGAAGATA
 M  T  T  N  W  E  P  S  C  E  K  I  I  P  I  N  S  Q  K  I 550       560       570       580       590       600
TTAAAAGGGGATGTCTCCATGTACCTCCTTCTGAAGGATGGTGGGCGTTACCGCTGCCAG
 L  K  G  D  V  S  M  Y  L  L  L  K  D  G  G  R  Y  R  C  Q 610       620       630       640       650       660
TTTGACACAATTTACAAAGCAAAGACTGAGCCAAAAGAAATGCCGGACTGGCACTTCATC
 F  D  T  I  Y  K  A  K  T  E  P  K  E  M  P  D  W  H  F  I 670       680       690       700       710       720
CAGCATAAGCTCAACCGTGAAGACCGCAGCGATGCTAAGAATCAGAAATGGCAACTGATA
 Q  H  K  L  N  R  E  D  R  S  D  A  K  N  Q  K  W  Q  L  I 730       740       750       760       770       780
GAACATGCTATTGCATCCCGATCTGCTTTACCCTGATAACAAGGAGTTGCTATTGCATG
 E  H  A  I  A  S  R  S  A  L  P  *

790       800       810       820       830       840
TGCATGCCTATTACGCTGATAAAAATGTAGTTTTAACATGCAATTGTATGTGCATGCACA

850
TTACCCTGATA                    (SEQ ID NOS:05 & 06)
```

FIG. 11

Green fluorescent protein from *Scolymia cubensis* scubGFP1 (AY037767)

```
           10         20         30         40         50         60
5'TGTGACATTCAGTCATATAGGAGCCTCTATCGGAGCTGAGGTCCCATTCACCGTTGTGAT
           70         80         90        100        110        120
  TTGGACGGGAGCAGATCGAGAACAACMAGGGCTGTACGAGTCTGATAATTTACTTTACAT
          130        140        150        160        170        180
  CTACCAACATGCAGCGTGCTGGGATGAAGGTTAAGGAACATATGAAGATCAAACTGCGTA
            M  Q  R  A  G  M  K  V  K  E  H  M  K  I  K  L  R  M
          190        200        210        220        230        240
  TGGGAGGTACTGTAAACGGAAAGCATTTCGCGGTTAATGGGACAGGAGACGGCTACCCTT
     G  G  T  V  N  G  K  H  F  A  V  N  G  T  G  D  G  Y  P  Y
          250        260        270        280        290        300
  ATCAGGGAAAACAGATTTTGAAACTTATCGTCGAAGGCAGCGAACCTCTGCCTTTCGCTT
     Q  G  K  Q  I  L  K  L  I  V  E  G  S  E  P  L  P  F  A  F
          310        320        330        340        350        360
  TTGATATCTTGTCAGCAGCATTCCAGTATGGCAACAGGGCATTCACCGAATACCCAACAG
     D  I  L  S  A  A  F  Q  Y  G  N  R  A  F  T  E  Y  P  T  E
          370        380        390        400        410        420
  AGATAGCAGACTATTTCAAGCAGTCGTTTGAGTTTGGCGAGGGGTTCTCCTGGGAACGAA
     I  A  D  Y  F  K  Q  S  F  E  F  G  E  G  F  S  W  E  R  S
          430        440        450        460        470        480
  GTTTCACTTTCGAAGATGGGGCCATTTGCGTCGCCACCAACGATATAACGATGGTTGGTG
     F  T  F  E  D  G  A  I  C  V  A  T  N  D  I  T  M  V  G  G
          490        500        510        520        530        540
  GTGAGTTTCAGTATGATATTCGATTTGATGGTCTGAACTTCCCTGAAGATGGTCCAGTGA
     E  F  Q  Y  D  I  R  F  D  G  L  N  F  P  E  D  G  P  V  M
          550        560        570        580        590        600
  TGCAAAAGAAAACCGTAAAATGGGAGCCATCCACTGAGATAATGTATATGCAAAATGGAG
     Q  K  K  T  V  K  W  E  P  S  T  E  I  M  Y  M  Q  N  G  V
          610        620        630        640        650        660
  TGCTGAAGGGTGAGGTTAACATGGCTCTGTTGCTTCAAGACAAAAGCCATTACCGTTGCG
     L  K  G  E  V  N  M  A  L  L  L  Q  D  K  S  H  Y  R  C  D
          670        680        690        700        710        720
  ACCTCAAAACTACTTACAAAGCTAAGAATAATGTGCCGCATCCTCCAGGCTACCACTATG
     L  K  T  T  Y  K  A  K  N  N  V  P  H  P  P  G  Y  H  Y  V
          730        740        750        760        770        780
  TGGATCACTGCATTGAAATACTCGAAGAACGTAAGGATCACGTTAAGCTGCGGGAGCATG
     D  H  C  I  E  I  L  E  E  R  K  D  H  V  K  L  R  E  H  A
          790        800        810        820        830        840
  CTAAAGCTCGTTCTAGCCTGTCACCTACCAGTGCAAAAGAACGAAAGGCTTAGGTGATAG
     K  A  R  S  S  L  S  P  T  S  A  K  E  R  K  A  *
          850        860        870        880        890        900
  TCAAAAAGACAACAAGACGAAAATGAAAGGTGTTCATTGTTAGAATTTGATATTTTCGAT
          910        920        930        940        950        960
  TCAATGATTCGTTAAGGGATTTGCTAGAGGCTAGCTAACAGGTTAACATCATAAGGATAG
          970        980        990       1000       1010       1020
  AGATTYCGTTGCGGAGTTAGAACCTTWATATTTTCCGAATTCCAMCTAGAGTCGTTGAGA
         1030       1040       1050       1060       1070       1080
  AATTTATTAGAGACTAGCTTTAGAGTTACTTTTGTGGAAAAAAGGTTTCCATTTTTTGC
         1090       1100       1110       1120       1130       1140
  GTTATTACAGCATTTAAAGCATAGGAATAGAGATTCGGTTATGGAAAATAACAGTAGGAA
         1150       1160       1170
  AATACGTTGTGAAAATAAACTTGTTGTCGAAAAAAAAA 3'
```

(SEQ ID NOS:07&08)

FIG. 12

Green fluorescent protein from *Scolymia cubensis* scubGFP2 (AY037771)

```
         10         20         30         40         50         60
5'CCTGGTGATTTGGACGAGAGCAGATCGAGAATAGCAAGGTTTTACCAGCGTGATAATTTA
         70         80         90        100        110        120
  CTTTACATCTAACAACATGCAATCTGCTGGGAAGAAGAATGTCGTTAAGGACTTCATGAA
                       M  Q  S  A  G  K  K  N  V  V  K  D  F  M  K
        130        140        150        160        170        180
  GATCACACTGCGTATGGACGGTGCTGTAAACGGGAAGCCCTTCGCGGTTAATGGAACAGG
   I  T  L  R  M  D  G  A  V  N  G  K  P  F  A  V  N  G  T  G
        190        200        210        220        230        240
  AGATGGCAACCCTTATGGTGGAATACAGAGTTTGAAGCTTACCGTCGATGGCAACAAACC
   D  G  N  P  Y  G  G  I  Q  S  L  K  L  T  V  D  G  N  K  P
        250        260        270        280        290        300
  TCTGCCTTTTGCTTTTGATATCTTGTCAGCAGCATTCCAGTATGGCAACAGGGCATTCAC
   L  P  F  A  F  D  I  L  S  A  A  F  Q  Y  G  N  R  A  F  T
        310        320        330        340        350        360
  CGAATACCCAAAAGAGATATCAGACTATTTCAAGCAGTCGTTTGAGTTTGGCGAGGGGTT
   E  Y  P  K  E  I  S  D  Y  F  K  Q  S  F  E  F  G  E  G  F
        370        380        390        400        410        420
  TACCTGGGAACGAAGTTTCACTTTCGAAGACGGGGCCATTTGCGTCGCCACGAACGATAT
   T  W  E  R  S  F  T  F  E  D  G  A  I  C  V  A  T  N  D  I
        430        440        450        460        470        480
  AAAGATGGTTGGCGATGAGTTTCAATATAACATTCGATTTGATGGTGTGAATTTCCCTGA
   K  M  V  G  D  E  F  Q  Y  N  I  R  F  D  G  V  N  F  P  E
        490        500        510        520        530        540
  AGATGGTCCWGTYATGCAGAAGAAAACGGTGAAGTGGGAGCCATCCACAGAGATAATGCG
   D  G  P  V  M  Q  K  K  T  V  K  W  E  P  S  T  E  I  M  R
        550        560        570        580        590        600
  TGTGCAAGGTGGAGTGCTAAAGGGTGAGGTTAACATGGCTCTGTTGCTTAAAGACAAAAG
   V  Q  G  G  V  L  K  G  E  V  N  M  A  L  L  L  K  D  K  S
        610        620        630        640        650        660
  CCATTACCGATGTGACTTCAAAACTACTTACAAAGCTAAGAATCCTGTCCCGCCGACGGC
   H  Y  R  C  D  F  K  T  T  Y  K  A  K  N  P  V  P  P  T  A
        670        680        690        700        710        720
  GCTTCCAGACTACCACTATGTGGATCACTGTATTGAAATCACCGAGGAAAATAGGGATTA
   L  P  D  Y  H  Y  V  D  H  C  I  E  I  T  E  E  N  R  D  Y
        730        740        750        760        770        780
  CGTTAAGCTGCAGGAGTATGCTAAAGCTCGTTCTGGCCTGCACCTGCCCGAACTGCAAAA
   V  K  L  Q  E  Y  A  K  A  R  S  G  L  H  L  P  E  L  Q  K
        790        800        810
  GTAAAGGCTTAGGCGATAGTCAAGACGACAACGAGAAGA 3'
   *
```

(SEQ ID NO:09 & 10)

FIG. 13

Red fluorescent protein from *Ricordea florida* rfloRFP (AY037773)

```
         10        20        30        40        50        60
5'TGTGAAAGTTAACATTTTACTTTACTTCTACCAGCATGAGTGCACTCAAAGAGGAAATGA
                                     M  S  A  L  K  E  E  M  K 70        80        90       100       110       120
  AAATCAAGCTTACATTGGTGGGCGTTGTTAACGGGCACCCATTCAAGATCATTGGGGACG
   I  K  L  T  L  V  G  V  V  N  G  H  P  F  K  I  I  G  D  G 130       140       150       160       170       180
  GAAAAGGCAAACCCTATGAGGGATCGCAGGAATTAACCCTTGCCGTGGTGGAAGGAGGGC
   K  G  K  P  Y  E  G  S  Q  E  L  T  L  A  V  V  E  G  G  P 190       200       210       220       230       240
  CTCTGCCTTTCTCTTATGATATCCTGACAACGATAGTTCACTATGGCAACAGGGCATTTG
   L  P  F  S  Y  D  I  L  T  T  I  V  H  Y  G  N  R  A  F  V 250       260       270       280       290       300
  TGAACTACCCAAAGGACATACCAGATATTTTCAAGCAGACCTGCTCTGGTCCTGGTGCTG
   N  Y  P  K  D  I  P  D  I  F  K  Q  T  C  S  G  P  G  A  G 310       320       330       340       350       360
  GATATTCCTGGCAAAGGACCATGAGTTTTGAAGACGGAGGCGTTTGCACTGCTACGAGCC
   Y  S  W  Q  R  T  M  S  F  E  D  G  V  C  T  A  T  S  H 370       380       390       400       410       420
  ATATCAGGGTGGATGGCGACACTTTCAATTATGACATTCACTTCATGGGAGCGGATTTCC
   I  R  V  D  G  D  T  F  N  Y  D  I  H  F  M  G  A  D  F  P 430       440       450       460       470       480
  CTCTTAATGGTCCAGTGATGCAGAAAAGAACAGTGAAATGGGAGCCATCCACTGAGATAA
   L  N  G  P  V  M  Q  K  R  T  V  K  W  E  P  S  T  E  I  M 490       500       510       520       530       540
  TGTTTCAATGTGATGGATTGCTGAGGGGTGATGTTGCCATGTCTCTGTTGCTGAAAGGAG
   F  Q  C  D  G  L  L  R  G  D  V  A  M  S  L  L  K  G  G 550       560       570       580       590       600
  GCGGCCATTACCGATGTGACTTTAAAACTATTTATAAACCCAAGAAGAATGTCAAGATGC
   G  H  Y  R  C  D  F  K  T  I  Y  K  P  K  K  N  V  K  M  P 610       620       630       640       650       660
  CAGGTTACCATTTTGTGGACCACTGCATTGAGATAACGAGTCAACAGGACGATTACAACG
   G  Y  H  F  V  D  H  C  I  E  I  T  S  Q  Q  D  D  Y  N  V 670       680       690       700       710       720
  TGGTTGAGCTGTACGAGGGTGCTGTAGCCCACTACTCTCCTCTGCAGAAACCATGCCAAG
   V  E  L  Y  E  G  A  V  A  H  Y  S  P  L  Q  K  P  C  Q  A 730       740       750       760       770       780
  CAAAGGCATAAAGCCAAACAACCCAAGAGGACAACAAGACATTTAATCAAATCACATCTT
   K  A  *

790       800
  TGTATTTTTGGTTAGAGTTGAAAAAAA 3'
```

(SEQ ID NO:11 & 12)

FIG. 14

Green fluorescent protein from *Ricordea florida* rfloGFP (AY037772)

```
            10         20         30         40         50         60
5'AGTCACCTCGGTGTTTTTAGGACAGGAAGGATCACGAGCAAGAGAAGAACTGTGAAAGTT
            70         80         90        100        110        120
  AACACTTTACTCTACTTCTACCAGCATGAGTGCACTCAAAGAGGAAATGAAAATCAAGCT
                                  M  S  A  L  K  E  E  M  K  I  K  L
           130        140        150        160        170        180
  TAAAATGGTGGGCGTTGTTAACGGGCAGTCATTTCAGATCGATGGGGAAGGAAAAGGCAA
   K  M  V  G  V  V  N  G  Q  S  F  Q  I  D  G  E  G  K  G  K
           190        200        210        220        230        240
  ACCTTACGAGGGATCACAGAAATTAACCCTTGAAGTGGTGGAAGGAGGGCCTCTGCTCTT
   P  Y  E  G  S  Q  K  L  T  L  E  V  V  E  G  G  P  L  L  F
           250        260        270        280        290        300
  CTCTTATGATATCCTGACAACGATATTTCAGTATGGCAACAGGGCATTCGTGAACTACCC
   S  Y  D  I  L  T  T  I  F  Q  Y  G  N  R  A  F  V  N  Y  P
           310        320        330        340        350        360
  AAAGGACATACCAGATATTTTCAAGCAGACCTGCTCTGGTCCTGATGGTGGATTTTCCTG
   K  D  I  P  D  I  F  K  Q  T  C  S  G  P  D  G  G  F  S  W
           370        380        390        400        410        420
  GCAAAGGACCATGACTTATGAAGACGGAGGGGTTTGCACTGCTTCAAACCACATCAGCGT
   Q  R  T  M  T  Y  E  D  G  G  V  C  T  A  S  N  H  I  S  V
           430        440        450        460        470        480
  GGACGGCGACACTTTTTATTATGTGATAAGATTTAATGGAGAGAATTTTCCTCCAAATGG
   D  G  D  T  F  Y  Y  V  I  R  F  N  G  E  N  F  P  P  N  G
           490        500        510        520        530        540
  TCCAGTAATGCAGAAAAGAACAGTGAAATGGGAGCCATCCACTGAGATAATGTTTGAACG
   P  V  M  Q  K  R  T  V  K  W  E  P  S  T  E  I  M  F  E  R
           550        560        570        580        590        600
  TGATGGATTGCTGAGGGGTGACATTGCCATGTCTCTGTTGCTGAAAGGAGGCGGCCATTA
   D  G  L  L  R  G  D  I  A  M  S  L  L  L  K  G  G  H  Y
           610        620        630        640        650        660
  CCGATGTGACTTTAAAACTATTTATACACCCAAGAGGAAGGTCAACATGCCAGGTTACCA
   R  C  D  F  K  T  I  Y  T  P  K  R  K  V  N  M  P  G  Y  H
           670        680        690        700        710        720
  TTTTGTGGACCACTGCATTGAGATACAGAAGCACGACAAGGATTACAACATGGCTGTGCT
   F  V  D  H  C  I  E  I  Q  K  H  D  K  D  Y  N  M  A  V  L
           730        740        750        760        770        780
  CTCTGAGGATGCTGTAGCCCACAACTCTCCTCTGGAGAAAAAAGCCAAGCAAAGGCGTA
   S  E  D  A  V  A  H  N  S  P  L  E  K  K  S  Q  A  K  *
           790
  AAGCCAAACAACCTAA 3'
```

(SEQ ID NO:13&14)

FIG. 15

Red fluorescent protein from *Montastraea cavernosa* mcavRFP (AY037770)

```
          10        20        30        40        50        60
5'ACGCAGGGATTCACCCTGGTGATTTGGAAGAGAGCAGACCGAGAACAACAAGAGCTGTAT
          70        80        90       100       110       120
  AAGGCTGATATCTTACTTTACGTCTACCATCATGAGTGTGATTAAATCAGTCATGAAGAT
   R  L  I  S  Y  F  T  S  T  I  M  S  V  I  K  S  V  M  K  I 130       140       150       160       170       180
  CAAGCTGCGTATGGAAGGCAGTGTAAACGGGCACAACTTCGTAATTGTTGGAGAAGGAGA
   K  L  R  M  E  G  S  V  N  G  H  N  F  V  I  V  G  E  G  E 190       200       210       220       230       240
  AGGCAAGCCTTATGAGGGAACACAGAGTATGGACCTTACAGTCAAAGAAGGCGCACCTCT
   G  K  P  Y  E  G  T  Q  S  M  D  L  T  V  K  E  G  A  P  L 250       260       270       280       290       300
  GCCTTTCGCCTACGATATCATGACAACAGTATTCCATTACGGCAATAGGGTATTCGCAAA
   P  F  A  Y  D  I  M  T  T  V  F  H  Y  G  N  R  V  F  A  K 310       320       330       340       350       360
  ATACCCAAAACATATCCCAGACTATTTCAAGCAGATGTTTCCTGAGGAGTATTCCTGGGA
   Y  P  K  H  I  P  D  Y  F  K  Q  M  F  P  E  E  Y  S  W  E 370       380       390       400       410       420
  ACGAAGCATGAATTTCGAAGGCGGGGGCATTTGCACCGCCAGGAACGAGATAACAATGGA
   R  S  M  N  F  E  G  G  G  I  C  T  A  R  N  E  I  T  M  E 430       440       450       460       470       480
  AGGCGACTGTTTTTTTCAATAAAGTTCGATTTGATGGTGTGAACTTCCCCCCCAATGGTCC
   G  D  C  F  F  N  K  V  R  F  D  G  V  N  F  P  P  N  G  P 490       500       510       520       530       540
  AGTCATGCAGAAGAAGACGCTGAAATGGGAGCCATCCACTGAAAAAATGTATGTGCGTGA
   V  M  Q  K  K  T  L  K  W  E  P  S  T  E  K  M  Y  V  R  D 550       560       570       580       590       600
  TGGAGTGCTGACGGGTGATATCAACATGGCTTTGTTGCTTGAAGGAGGTGGCCATTACCG
   G  V  L  T  G  D  I  N  M  A  L  L  L  E  G  G  G  H  Y  R 610       620       630       640       650       660
  ATGTGACTTCAGAACTACTTACAGAGCTAAGAAGAAGGGTGTCAAGTTACCAGATTATCA
   C  D  F  R  T  T  Y  R  A  K  K  K  G  V  K  L  P  D  Y  H 670       680       690       700       710       720
  CTTTGAGGATCACTCCATTGAGATTTTGCGCCATGACAAAGAATACACTGAGGTTAAGCT
   F  E  D  H  S  I  E  I  L  R  H  D  K  E  Y  T  E  V  K  L 730       740       750       760       770       780
  GTATGAGCATGCCGAAGCTCATTCTGGGCTGCCGAGGGTGGCAAAGTAAAGGCTTAACGA
   Y  E  H  A  E  A  H  S  G  L  P  R  V  A  K  *

790
  AAAGCCAAGACCACA 3'
```

(SEQ ID NO:15 & 16)

FIG. 16

Green fluorescent protein from *Montastraea cavernosa* mcavGFP (AY037769)

```
              10         20         30         40         50         60
5'ATTCGCCCTGGTGATTTGGAAGAGAGCAGATCGAGAACAACAAGAGCTGTAAGGTTGATA
              70         80         90        100        110        120
  TCTTACTTACGTCTACCATCATGACAAGTGTTGCACAGGAAAAGGGTGTGATTAAACCAG
                         M  T  S  V  A  Q  E  K  G  V  I  K  P  D
             130        140        150        160        170        180
  ACATGAAGATGAAGCTGCGTATGGAAGGTGCTGTAAACGGGCACAAGTTCGTGGTTGAAG
    M  K  M  K  L  R  M  E  G  A  V  N  G  H  K  F  V  V  E  G
             190        200        210        220        230        240
  GAGATGGAAAAGGGAAGCCTTTCGACGGAACACAGACTATGGACCTTACAGTCATAGAAG
    D  G  K  G  K  P  F  D  G  T  Q  T  M  D  L  T  V  I  E  G
             250        260        270        280        290        300
  GCGCACCATTGCCTTTCGCTTACGATATCTTGACAACAGTATTCGATTACGGCAACAGGG
    A  P  L  P  F  A  Y  D  I  L  T  T  V  F  D  Y  G  N  R  V
             310        320        330        340        350        360
  TATTCGCCAAATACCCAGAAGACATAGCAGATTATTTCAAGCAGACGTTTCCTGAGGGGT
    F  A  K  Y  P  E  D  I  A  D  Y  F  K  Q  T  F  P  E  G  Y
             370        380        390        400        410        420
  ACTTCTGGGAACGAAGCATGACATACGAAGACCAGGGCATTTGCATCGCCACAAACGACA
    F  W  E  R  S  M  T  Y  E  D  Q  G  I  C  I  A  T  N  D  I
             430        440        450        460        470        480
  TAACAATGATGGAAGGCGTCGACGACTGTTTTGCCTATAAAATTCGATTTGATGGTGTGA
    T  M  M  E  G  V  D  D  C  F  A  Y  K  I  R  F  D  G  V  N
             490        500        510        520        530        540
  ACTTTCCTGCCAATGGTCCAGTTATGCAGAGGAAGACGCTGAAATGGGAGCCATCCACTG
    F  P  A  N  G  P  V  M  Q  R  K  T  L  K  W  E  P  S  T  E
             550        560        570        580        590        600
  AGATAATGTATGCGCGTGATGGAGTGCTGAAGGGTGATGTTAACATGGCTCTGTTGCTTG
    I  M  Y  A  R  D  G  V  L  K  G  D  V  N  M  A  L  L  L  E
             610        620        630        640        650        660
  AAGGAGGTGGCCATTACCGATGTGACTTCAAAACTACTTACAAAGCTAAGAAGGTTGTCC
    G  G  G  H  Y  R  C  D  F  K  T  T  Y  K  A  K  K  V  V  R
             670        680        690        700        710        720
  GGTTGCCAGACTATCACTTTGTGGACCATCGCATTGAGATTGTGAGCCACGACAAAGATT
    L  P  D  Y  H  F  V  D  H  R  I  E  I  V  S  H  D  K  D  Y
             730        740        750        760        770        780
  ACAACAAGGTTAAGCTGCACGAGCATGCCGAAGCTCGTCATGGACTGTCAAGGAAGGCCA
    N  K  V  K  L  H  E  H  A  E  A  R  H  G  L  S  R  K  A  K
             790        800        810        820        830        840
  AGTAAAGGCTTAATGAAAAGTCAAGACGACAACGAGGAGAAACAAAGTACTTTTTTGTTA
    *
             850        860        870        880        890        900
  AATTTGAAGGCATTTACTCGGAATTAGTATTTGATACTTTCGATTCAAGGATTTGTTCCG
             910        920        930        940        950        960
  GGATTTGTTAGAGACTAGCTCTAGAGTTGTATTTTGTGAAAAAAGATAGTTTCCAGTTTT
             970        980        990       1000       1010       1020
  TGCGGGATTACAGCATGGGGATAGACTTTTTAAACTCAGTTGTGGTCAAATGCAAGTAAG
            1030       1040       1050       1060
  AAAACTGTAGTGAGAATAAACTTGTTATCGAAGCCGAAAAAAAAAA 3'
```

(SEQ ID NOS: 17 & 18)

FIG. 17

Green fluorescent protein from *Condylactis gigantea* cgigGFP (AY037776)

```
         10        20        30        40        50        60
5'ACAGCTGTTCATCCACGCTCATTCAAGACGCCGTCAACTTTATTCCAGTCAGGAAAATGT
                                                             M  Y
         70        80        90       100       110       120
  ATCCTTGGATCAAGGAAACCATGCGCAGTAAGGTTTACATGGAAGGAGATGTTAACAACC
  P  W  I  K  E  T  M  R  S  K  V  Y  M  E  G  D  V  N  N  H
        130       140       150       160       170       180
  ACGCCTTCAAGTGCACTGCAGTAGGAGAAGGAAAACCATACAAAGGCTCACAAGACCTGA
   A  F  K  C  T  A  V  G  E  G  K  P  Y  K  G  S  Q  D  L  T
        190       200       210       220       230       240
  CGATTACCGTCACTGAAGGAGGTCCTCTGCCATTTGCTTTCGACATTCTTTCACACGCCT
   I  T  V  T  E  G  G  P  L  P  F  A  F  D  I  L  S  H  A  F
        250       260       270       280       290       300
  TTCAGTATGGCAACAAGGTGTTCACCGATTACCCCGACGATATTCCTGATTTCTTTAAGC
   Q  Y  G  N  K  V  F  T  D  Y  P  D  D  I  P  D  F  F  K  Q
        310       320       330       340       350       360
  AGTCTCTCTCGGATGGTTTTACTTGGAGAAGAGTAAGCACSTATGACGATGGAGGAGTCC
   S  L  S  D  G  F  T  W  R  R  V  S  T  Y  D  D  G  G  V  L
        370       380       390       400       410       420
  TCACAGTTACCCAAGACACTAGTCTGAAGGGAGATTGCATTATTTGCAACATTAAAGTCC
   T  V  T  Q  D  T  S  L  K  G  D  C  I  I  C  N  I  K  V  H
        430       440       450       460       470       480
  ATGGCACTAACTTCCCCGAAAATGGTCCGGTGATGCAAAACAAGACCGATGGATGGGAGC
   G  T  N  F  P  E  N  G  P  V  M  Q  N  K  T  D  G  W  E  P
        490       500       510       520       530       540
  CATCCAGCACTGAAACGGTTATTCCACAAGATGGAGGAATTGTTGCTGCGCGATCACCCG
   S  S  T  E  T  V  I  P  Q  D  G  G  I  V  A  A  R  S  P  A
        550       560       570       580       590       600
  CACTAAGGCTGCGTGATAAAGGTCATCTTATCTGCCACATGGAAACAACTTACAAGCCAA
   L  R  L  R  D  K  G  H  L  I  C  H  M  E  T  T  Y  K  P  N
        610       620       630       640       650       660
  ACAAAGAGGTGAAGCTGCCAGAACTCCACTTTCATCATTTGCGAATGGAAAAGCTGAGTG
   K  E  V  K  L  P  E  L  H  F  H  H  L  R  M  E  K  L  S  V
        670       680       690       700       710       720
  TTAGTGACGATGGGAAGACCATTAAGCAGCACGAGTATGTGGTGGCTAGCTACTCCAAAG
   S  D  D  G  K  T  I  K  Q  H  E  Y  V  V  A  S  Y  S  K  V
        730       740       750       760       770       780
  TGCCTTCGAAGATAGGACGTCAATGATCATTTCCCTTATTAAATATCAATGATGTGGCTT
   P  S  K  I  G  R  Q  *
        790       800       810       820       830       840
  TCAATTTTCCAAAATTTTGTTAAGACATAGGTCTTTTGGATTTTTGGTAACCCCAACCTT
        850       860       870       880       890
  AATTCCCAATAATTTTTGTTGGAAAGTCAAATAAAACCAGCCTTCCCTGGGCCTTTAA 3'
```

(SEQ ID NOS: 19 & 20)

FIG. 18

Green fluorescent protein from *Agaricia fragilis* afraGFP (AY037765)

```
         10        20        30        40        50        60
5'CAAGGAAGCCAAATCTTTTACCAGAGATCTCGCGTGAAAGCAACCTATGAGTGATGGCGA
                                                        M  A  I
         70        80        90       100       110       120
  TTTCTACTCTAAAGAACGTCATCATCATCGTTATTATATACTCCTGCAGCACTTGTGCTG
   S  T  L  K  N  V  I  I  I  V  I  I  Y  S  C  S  T  C  A  V
        130       140       150       160       170       180
  TTTGGTCGAATTCAAACTCTGAATCCTCTTTCACTAATGGGATTGCAGAGGAAATGAAGA
   W  S  N  S  N  S  E  S  S  F  T  N  G  I  A  E  E  M  K  T
        190       200       210       220       230       240
  CTAGGGTACATTTGGAGGGTACTGTTAACGGGCACTCCTTTACAATTAAAGGCGAAGGAA
   R  V  H  L  E  G  T  V  N  G  H  S  F  T  I  K  G  E  G  R
        250       260       270       280       290       300
  GAGGCTACCCTTACAAAGGAGAACAGTTTATGAGCCTTGAGGTCGTCAATGGTGCTCCTC
   G  Y  P  Y  K  G  E  Q  F  M  S  L  E  V  V  N  G  A  P  L
        310       320       330       340       350       360
  TGCCGTTCTCTTTTGATATCTTGACACCAGCATTTATGTATGGCAACAGAGTGTTCACCA
   P  F  S  F  D  I  L  T  P  A  F  M  Y  G  N  R  V  F  T  K
        370       380       390       400       410       420
  AGTACCCACCAAACATACCAGACTATTTCAAGCAGACGTTTCCTGAAGGGTATCACTGGG
   Y  P  P  N  I  P  D  Y  F  K  Q  T  F  P  E  G  Y  H  W  E
        430       440       450       460       470       480
  AAAGAAACATTCCCTTTGAAGATCAGGCCGCGTGCACGGTAACCAGCCACATAAGATTGG
   R  N  I  P  F  E  D  Q  A  A  C  T  V  T  S  H  I  R  L  E
        490       500       510       520       530       540
  AAGAGGAAGAGAGGCGTTTTGTAAATAACGTCAGATTTCACTGTGTGAACTTTCCCCCTA
   E  E  E  R  R  F  V  N  N  V  R  F  H  C  V  N  F  P  P  N
        550       560       570       580       590       600
  ATGGTCCAGTCATGCAGAGGAGGATACTGAAATGGGAGCCATCCACTGAGAACATTTATC
   G  P  V  M  Q  R  R  I  L  K  W  E  P  S  T  E  N  I  Y  P
        610       620       630       640       650       660
  CGCGTGATGGGTTTCTGGAGGGCCATGTTGATATGACTCTTCGGGTTGAAGGAGGTGGCT
   R  D  G  F  L  E  G  H  V  D  M  T  L  R  V  E  G  G  Y
        670       680       690       700       710       720
  ATTACCGAGCTGAGTTCAAAAGTACTTACAAAGGGAAGACCCCAGTCCGCGACATGCCAG
   Y  R  A  E  F  K  S  T  Y  K  G  K  T  P  V  R  D  M  P  D
        730       740       750       760       770       780
  ACTTTCACTTCATAGACCACCGCATTGAGATTACGGAGCATGACGAAGACTACACCAATG
   F  H  F  I  D  H  R  I  E  I  T  E  H  D  E  D  Y  T  N  V
        790       800       810       820       830       840
  TTGAGCTGCATGACGTATCCTGGGCTCGTTACTCTATGCTGCCGACTATGTAAGCGGAAA
   E  L  H  D  V  S  W  A  R  Y  S  M  L  P  T  M
        850       860       870       880       890       900
  AGGCAAGGCAACAAGACGCAAAACCGCCCTGTTTGTCTCTTTTCATAAGAGATTTGACAA
        910       920       930       940       950       960
  CCGTGGTTCTTTGCCATTTAATTTGAATTAGTTTAAATTAAATCTTTGGGATTGATGTAG
        970       980       990      1000      1010      1020
  ACGCTTTGGTTGCTAAGTAAGAAAACATTTGTGATTATTAAATTTGTTGCCTGAAGCAAA
       1030
  AAAAAAAAA 3'
```

(SEQ ID NOS:21 & 22)

FIG. 19

Green fluorescent protein from *Ricordea florida* rfloGFP2 (AY037774)

```
          10         20         30         40         50         60
5'AGCCACTTCGGTGTCTTGTCGAGAGGAAGGATCACGAACAAGAGAAGAGCTGTAAAAGTT
          70         80         90        100        110        120
  AAAATTTTACTTTACTTCTTCCAGCATGAATGCACTTCAAGAGGAAATGAAAATCAAGCT
                                  M  N  A  L  Q  E  E  M  K  I  K  L
         130        140        150        160        170        180
  TACAATGGTGGGCGTTGTTAACGGGCAGTCATTTAAGATCGATGGGAAAGGAAAAGGGAA
   T  M  V  G  V  V  N  G  Q  S  F  K  I  D  G  K  G  K  G  K
         190        200        210        220        230        240
  ACCTTACGAGGGATCACAGGAATTGACCCTTAAAGTGGTGGAAGGCGGGCCTCTGCTCTT
   P  Y  E  G  S  Q  E  L  T  L  K  V  V  E  G  G  P  L  L  F
         250        260        270        280        290        300
  CTCTTATGATATCCTGACAACGATATTTCAGTATGGCAACAGGGCATTCGTGAACTACCC
   S  Y  D  I  L  T  T  I  F  Q  Y  G  N  R  A  F  V  N  Y  P
         310        320        330        340        350        360
  AAAGGACATACCAGATATTTTCAAGCAAACGTGTTCTGGTCTTGATGGCGGATATTCGTG
   K  D  I  P  D  I  F  K  Q  T  C  S  G  L  D  G  G  Y  S  W
         370        380        390        400        410        420
  GCAAAGGACCATGACTTATGAGGACGGAGGGGTTTGTACTGCTACAAGCAACGTCAGCGT
   Q  R  T  M  T  Y  E  D  G  G  V  C  T  A  T  S  N  V  S  V
         430        440        450        460        470        480
  GGTCGGCGACACTTTCAATTATGAAATTCACTTTATGGGGGCGAATTTTCCTCCAAATGG
   V  G  D  T  F  N  Y  E  I  H  F  M  G  A  N  F  P  P  N  G
         490        500        510        520        530        540
  TCCRGTGATGCAGAAAAGAACAGTGAAGTGGGAGCCCTCCACTGAGATAATGTTTGAACG
   P  V  M  Q  K  R  T  V  K  W  E  P  S  T  E  I  M  F  E  R
         550        560        570        580        590        600
  TGATGGATTGCTGAGGGGTGATGTTCCCATGTCTCTGTTGCTGAAAGGAGGCGACCATTA
   D  G  L  L  R  G  D  V  P  M  S  L  L  L  K  G  G  D  H  Y
         610        620        630        640        650        660
  CCGATGTGACTTTAAAACTATTTATAAACCCAACAAGAAGGTCAAGCTGCCAGGTTACCA
   R  C  D  F  K  T  I  Y  K  P  N  K  K  V  K  L  P  G  Y  H
         670        680        690        700        710        720
  TTTTGTGGACCACTGCATTGAGATAAAGAGTCAAGAGAATGATTACAACATGGTTGCGCT
   F  V  D  H  C  I  E  I  K  S  Q  E  N  D  Y  N  M  V  A  L
         730        740        750        760        770        780
  CTTTGAGGATGCTGTAGCACACTACTCTCCTCTGGAGAAAAAGAGCCAGGCAAAGGCGTA
   F  E  D  A  V  A  H  Y  S  P  L  E  K  K  S  Q  A  K  A  *
         790        800        810        820        830        840
  AATCCAAACAACCTAAGAAGACGACAAGGCATTCAATCTAATCGCATGTTTGAATTTTTG
         850        860        870        880        890        900
  GTTAGGAATGTGTTGGGTCAGACTAGGTCTAGAACGTTTCATTTTGGCTGGATTTGTTTT
         910        920        930        940        950        960
  ACTCAGTTATAGACAAGAAAAAAATCTTAAATGACTTGGGTTGGATTTAGCTTTCGGCAC
         970        980        990       1000       1010       1020
  TGTCAATTCCGGATTCCTTAGAAATATTTGAGACCAAGCCTTTTTTTGAGCTGAGAACGT
  AATC 3'
```

(SEQ ID NOS: 23 & 24)

FIG. 20

Green fluorescent protein from *Montastraea cavernosa* mcavGFP2 (AY037768)

```
         10         20         30         40         50         60
5'AGAGCTGTAGGGTGATATCTTACTTACGTCTACCATCATGACCAGTGTTGCACAGGAAAA
                                           M  T  S  V  A  Q  E  K
         70         80         90        100        110        120
  GGGTGTGATTAAACCAGACATGAAGATGAAGCTGCGTATGGAAGGTGCTGTAAACGGGCA
   G  V  I  K  P  D  M  K  M  K  L  R  M  E  G  A  V  N  G  H
        130        140        150        160        170        180
  CAAGTTCGTGATTGAAGGAGATGGAAAAGGGAAGCCTTTCGACGGAACACAGACTATGGA
   K  F  V  I  E  G  D  G  K  G  K  P  F  D  G  T  Q  T  M  D
        190        200        210        220        230        240
  CCTTACAGTCATAGAAGGCGCACCATTGCCTTTCGCTTACGCTATCTTGACAACAGTATT
   L  T  V  I  E  G  A  P  L  P  F  A  Y  A  I  L  T  T  V  F
        250        260        270        280        290        300
  CGATTACGGCAACAGGGTATTCGCCAAATACCCAGAAGACATAGCAGATTATTTCAAGCA
   D  Y  G  N  R  V  F  A  K  Y  P  E  D  I  A  D  Y  F  K  Q
        310        320        330        340        350        360
  GACATTTCCTGAGGGGTACTTCTGGGAACGAAGCATGACATACGAAGACCAGGGCATTTG
   T  F  P  E  G  Y  F  W  E  R  S  M  T  Y  E  D  Q  G  I  C
        370        380        390        400        410        420
  CATCGCCACAAACGACATAACAATGATGAAAGGCGTCGACGACTGTTTTGTCTATAAAAT
   I  A  T  N  D  I  T  M  M  K  G  V  D  D  C  F  V  Y  K  I
        430        440        450        460        470        480
  TCGATTTGATGGTGTGAACTTTCCTGCCAATGGTCCAGTTATGCAGAGGAAGACGCTGAA
   R  F  D  G  V  N  F  P  A  N  G  P  V  M  Q  R  K  T  L  K
        490        500        510        520        530        540
  ATGGGAGCCATCCACTGAGAAAATGTATGCGCGTGATGGAGTGCTGAAGGGTGATGTTAA
   W  E  P  S  T  E  K  M  Y  A  R  D  G  V  L  K  G  D  V  N
        550        560        570        580        590        600
  CATGGCTCTGTTGCTTGAAGGAGGTGGCCATTACCGATGTGACTTCAAAACTACTTACAG
   M  A  L  L  E  G  G  G  H  Y  R  C  D  F  K  T  T  Y  R
        610        620        630        640        650        660
  AGCTAAGAAGGTTGTCCAGTTGCCAGACTATCATTTTGTGGACCATCGCATTGAGATTGT
   A  K  K  V  V  Q  L  P  D  Y  H  F  V  D  H  R  I  E  I  V
        670        680        690        700        710        720
  GAGCCACGACAAAGATTACAACAAGGTTAAGCTGTATGAGCATGCCGAAGCTCATTCTGG
   S  H  D  K  D  Y  N  K  V  K  L  Y  E  H  A  E  A  H  S  G
        730        740        750        760        770        780
  GCTGCCGAGGCAGGCCAAGTAAAGGCTTAATGAAAAGCCAAGACGACAACAAGGAGAAAC
   L  P  R  Q  A  K  *
        790        800        810        820        830        840
  AAAGTATTTTTTTTGTTAAATTTCAAGGCATTTACTCGGAATTAGTATTTGATACTTTCG
        850        860        870        880        890        900
  ATTCAAGGATTTGTTTCGGGACTTGTTAGAGACCAGCTCTAGAGTTGTATTTTGTGAAAA
        910
  AAAGATAGTTTCC 3'
```

(SEQ ID NOS: 25 & 26)

FIG. 21

Green fluorescent protein homolog from *Montastraea annularis* mannFP (AY037766)

```
         10         20         30         40         50         60
5'TGGTTAACGCAGAGTCGCGGGGGGTTCCTGGCTAATAATTGATTCTATTTTGGGTGTGAC
         70         80         90        100        110        120
ATTCAGGTTTAAAGCAGCATCCTCAGTGCTGAGGTCTCATTCACCCTGGTGATTTGGAAG
        130        140        150        160        170        180
AGAGCAGATCGAGAACACCAAGAGCTGTATTACGCTAAAATCTTACTTGCCTCTACCACC
        190        200        210        220        230        240
ATGAGTATGATTAAACCAGAAATGAAGATCAAGATGCGTATGGACGGTGCTGTAAACGGG
  M  S  M  I  K  P  E  M  K  I  K  M  R  M  D  G  A  V  N  G
        250        260        270        280        290        300
CACAAGTTCGTGATTACACGGGAAGGAAGCGGCGAGCCTTTCGAGGGAAAACAGACTATG
  H  K  F  V  I  T  G  E  G  S  G  E  P  F  E  G  K  Q  T  M
        310        320        330        340        350        360
AACCTGACAGTCATAGACGGCGGACCTCTGCCTTTCGCTTTCGACATCTTGACAACAGCA
  N  L  T  V  I  D  G  G  P  L  P  F  A  F  D  I  L  T  T  A
        370        380        390        400        410        420
TTCGATTACGGCAMCAGGGTATTCGCCAAATACCCAGAAGACATCCCAGACTATTTCAAG
  F  D  Y  G  X  R  V  F  A  K  Y  P  E  D  I  P  D  Y  F  K
        430        440        450        460        470        480
CAGTCGTTTCCTGAGGGGTTTTCTTGGGAACGAAGCATGACTTACGAAGACGGGGGCATT
  Q  S  F  P  E  G  F  S  W  E  R  S  M  T  Y  E  D  G  G  I
        490        500        510        520        530        540
TGCATCGCCACAAATGACATAAAAATGGAAGGCGACTGCTTTTCCTATGAAATTCGATTT
  C  I  A  T  N  D  I  K  M  E  G  D  C  F  S  Y  E  I  R  F
        550        560        570        580        590        600
GATGGGGTGAACTTTCCTGCCAATAGTCCAGTTATGCAGAAGAAGACCGTGAAATGGGAG
  D  G  V  N  F  P  A  N  S  P  V  M  Q  K  K  T  V  K  W  E
        610        620        630        640        650        660
CCATGCACTGRGGAAATGTATGTGCGTGATGGAGTGCTTAAAGGTGGTCTTAACATGGCT
  P  C  T  X  E  M  Y  V  R  D  G  V  L  K  G  G  L  N  M  A
        670        680        690        700        710        720
CTGTTGCTTGAAGGAGGTGGCCATTTCCGATGTGACTTGAAAACTACTTACAAAGCTAAG
  L  L  L  E  G  G  H  F  R  C  D  L  K  T  T  Y  K  A  K
        730        740        750        760        770        780
AAGGTTGTCCAGATGCCAGACTATCACTTTGTGAATCACCGACTTGAGATAACATGGCAT
  K  V  V  Q  M  P  D  Y  H  F  V  N  H  R  L  E  I  T  W  H
        790        800        810        820        830        840
GACGAGGATTACAACAATGTTAAGCTGTCTGAGCATGCAGAAGCTCATTCTGGACTGCCA
  D  E  D  Y  N  N  V  K  L  S  E  H  A  E  A  H  S  G  L  P
        850        860        870        880        890        900
AGGCAGGCCAAATAAAGGCTTGACGAAAAGCCAAAACGGCAAAGAGTACAAGAAAGTATA
  R  Q  A  K  *
        910        920        930        940        950        960
TATAAATGTATATTTTTCAACTGAAAGGCATTCCACTCGGAATTAGTATTTGATACTTTC
        970        980        990       1000       1010       1020
AATTCAAGGATTTATTTTGGGATTTGCTAGCCACTAGCTTTATTGTTAAATTAAGTTAAA
       1030       1040       1050       1060       1070       1080
GACGGTTTAGCATTTTTTCGGTATTACAACATAGGCACAGACGTCTTAACCCCAGTAGTG
       1090       1100       1110       1120       1130
GTCAGGTACAAGTAAGAAAACTTTGGTGAGAATAGACTTGTAGTCGAAAAAAA 3'
```

(SEQ ID NOS:27 & 28)

SEQUENCE LISTING

<160> NUMBER OF SEQ ID NOS: 28

<210> SEQ ID NO 1
<211> LENGTH: 868
<212> TYPE: DNA
<213> ORGANISM: Heteractis crispa

<400> SEQUENCE: 1

```
attttggaca ggtgttcaac caagcaaatt taagaagtca tcatctttat ctcagtcagg      60
aaaatgtgtt cttacatcaa agaaaccatg caaagtaagg tttacatgga aggaaaagtt    120
aacgaccaca acttcaagtg cactgcagaa ggaaaaggag aaccatacaa aggctcacaa    180
agcctgacga tcaccgtaac tgaaggaggt cctctgccat tgccttcga cattctttca     240
cacgccttc gatatggcaa taaggtgttc gccaagtacc ccaaagatca tcctgatttt     300
tttaagcagt ctcttcctga aggttttact tgggaaagag taagcaacta tgaggacgga   360
ggagtcctta ccgttaaaca agaaactagt ctggagggag attgcattat ttgcaaaatt    420
aaagcacatg gcactaactt ccccgcagat ggtccggtga tgcaaaaacg accaatgga    480
tgggagccat caactgaaac ggttattcca cggggtggag gaattctgat gcgcgatgtg   540
cccgcactga agctgcttgg taacaaagga catcttctct gcgtcatgga aacaacttac   600
aagtcaaaaa aaaaggtga acctgccaaa ccgcactttc atcatttgag aatggagaag    660
gatagtgtta gtgacgatga aagaccatt gagcagcacg agaatgtgag ggcaagctac    720
ttcaatgata gtggaaaatg atcatttcct tattgatttc aatgttaggg cattcagttt   780
ccaaattttc ttagacacag tcttttcctt tagcttcgta gcctacttac ccatgttttg    840
ttgaagtcaa taaatagcta agcactac                                        868
```

<210> SEQ ID NO 2
<211> LENGTH: 225
<212> TYPE: PRT
<213> ORGANISM: Heteractis crispa

<400> SEQUENCE: 2

```
Met Cys Ser Tyr Ile Lys Glu Thr Met Gln Ser Lys Val Tyr Met Glu
  1               5                  10                  15

Gly Lys Val Asn Asp His Asn Phe Lys Cys Thr Ala Glu Gly Lys Gly
             20                  25                  30

Glu Pro Tyr Lys Gly Ser Gln Ser Leu Thr Ile Thr Val Thr Glu Gly
         35                  40                  45

Gly Pro Leu Pro Phe Ala Phe Asp Ile Leu Ser His Ala Phe Arg Tyr
     50                  55                  60

Gly Asn Lys Val Phe Ala Lys Tyr Pro Lys Asp His Pro Asp Phe Phe
 65                  70                  75                  80

Lys Gln Ser Leu Pro Glu Gly Phe Thr Trp Glu Arg Val Ser Asn Tyr
                 85                  90                  95

Glu Asp Gly Gly Val Leu Thr Val Lys Gln Glu Thr Ser Leu Glu Gly
            100                 105                 110

Asp Cys Ile Ile Cys Lys Ile Lys Ala His Gly Thr Asn Phe Pro Ala
        115                 120                 125

Asp Gly Pro Val Met Gln Lys Arg Thr Asn Gly Trp Glu Pro Ser Thr
    130                 135                 140

Glu Thr Val Ile Pro Arg Gly Gly Ile Leu Met Arg Asp Val Pro
145                 150                 155                 160
```

```
Ala Leu Lys Leu Leu Gly Asn Lys Gly His Leu Leu Cys Val Met Glu
            165                 170                 175

Thr Thr Tyr Lys Ser Lys Lys Gly Glu Pro Ala Lys Pro His Phe
            180                 185                 190

His His Leu Arg Met Glu Lys Asp Ser Val Ser Asp Glu Lys Thr
            195                 200                 205

Ile Glu Gln His Glu Asn Val Arg Ala Ser Tyr Phe Asn Asp Ser Gly
    210                 215                 220

Lys
225

<210> SEQ ID NO 3
<211> LENGTH: 845
<212> TYPE: DNA
<213> ORGANISM: Dendronephthya sp

<400> SEQUENCE: 3
catatcgaga aagttgtgaa accaaattct tactctactt ttactaccat gaatctgatt      60
aaagaagata tgagggttaa ggtgcatatg gaagggaatg taaacgggca tgcttttgtg     120
attgaagggg aaggaaaagg aaggccctac gaagggacac agaccttgaa cctgacagtg     180
aaagaaggcg cgcctctccc attttcttac gacatcttga aacagcatt gcactacgga      240
aacagagtat tcactgaata cccagcagat atcacggatt atttcaagca atcatttcct     300
gaaggatatt cctgggaaag aaccatgact tatgaagaca agggcatttg taccatcaga     360
agcgacataa gcttggaagg tgactgcttt ttccaaaaca ttcgttttaa tgggatgaac     420
tttccccaa atggtccagt tatgcagaag aaaactttga agtgggaacc atccacagag      480
aagctgcacg tgcgtgatgg gttgcttgtc ggtaatatta acatggctct gctgcttgaa     540
ggaggtggac attacctgtg tgacttcaaa actacttaca aagcgaagaa ggttgttcag     600
ttgccagatt atcattttgt ggaccatcgc attgagatct tgagtaatga cagcgattac     660
aacaaagtga agctgtacga gcatgggggt gctcgctatt ctccgttgcc caagtcaggc     720
ctggtagagg ttcaagggaa agccataatg actgcataga taaacatgta gtgaagacca     780
catactcggg attagagttt agggattggt agttgtggta gattctagcc tacaaattt      840
ttggg                                                                 845

<210> SEQ ID NO 4
<211> LENGTH: 236
<212> TYPE: PRT
<213> ORGANISM: Dendronephthya sp

<400> SEQUENCE: 4

Met Asn Leu Ile Lys Glu Asp Met Arg Val Lys Val His Met Glu Gly
1               5                   10                  15

Asn Val Asn Gly His Ala Phe Val Ile Glu Gly Glu Gly Lys Gly Arg
            20                  25                  30

Pro Tyr Glu Gly Thr Gln Thr Leu Asn Leu Thr Val Lys Glu Gly Ala
        35                  40                  45

Pro Leu Pro Phe Ser Tyr Asp Ile Leu Thr Thr Ala Leu His Tyr Gly
    50                  55                  60

Asn Arg Val Phe Thr Glu Tyr Pro Ala Asp Ile Thr Asp Tyr Phe Lys
65                  70                  75                  80

Gln Ser Phe Pro Glu Gly Tyr Ser Trp Glu Arg Thr Met Thr Tyr Glu
                85                  90                  95
```

```
Asp Lys Gly Ile Cys Thr Ile Arg Ser Asp Ile Ser Leu Glu Gly Asp
            100                 105                 110

Cys Phe Phe Gln Asn Ile Arg Phe Asn Gly Met Asn Phe Pro Pro Asn
        115                 120                 125

Gly Pro Val Met Gln Lys Lys Thr Leu Lys Trp Glu Pro Ser Thr Glu
    130                 135                 140

Lys Leu His Val Arg Asp Gly Leu Leu Val Gly Asn Ile Asn Met Ala
145                 150                 155                 160

Leu Leu Leu Glu Gly Gly His Tyr Leu Cys Asp Phe Lys Thr Thr
                165                 170                 175

Tyr Lys Ala Lys Lys Val Val Gln Leu Pro Asp Tyr His Phe Val Asp
            180                 185                 190

His Arg Ile Glu Ile Leu Ser Asn Asp Ser Asp Tyr Asn Lys Val Lys
                195                 200                 205

Leu Tyr Glu His Gly Val Ala Arg Tyr Ser Pro Leu Pro Lys Ser Gly
    210                 215                 220

Leu Val Glu Val Gln Gly Lys Ala Ile Met Thr Ala
225                 230                 235

<210> SEQ ID NO 5
<211> LENGTH: 851
<212> TYPE: DNA
<213> ORGANISM: Zoanthus sp

<400> SEQUENCE: 5
gagttgagtt ctcgacttca gttgtatcac ttttgacgta tcaagtgatc tattctcaac    60
atggcccatt caaagcacgg actaacagat gacatgacaa tgcatttccg tatggaaggg   120
tgcgtcgatg gacataagtt tgtaatcgag ggcaacggca atggaaatcc tttcaagggg   180
aaacagttta ttaatctgtg tgtgattgaa ggaggaccac tgccattctc cgaagacata   240
ttgtctgctg cgtttgacta cggaaacagg ctcttcactg aatatcctga aggcatagtt   300
gactatttca gaactcgtgt cctgctggga tatacgtggc acaggtcttt tcgctttgaa   360
gatggagcag tttgcatatg cagtgcagat ataacagtaa atgttaggga aaactgcatt   420
tatcatgagt ccacgtttta tggagtgaac tttcctgctg atggacctgt gatgaaaaag   480
atgacaacta ttgggaacc gtcctgcgag aaaatcatac caataaatag tcagaagata   540
ttaaagggg atgtctccat gtacctcctt ctgaaggatg gtgggcgtta ccgctgccag   600
tttgacacaa tttacaaagc aaagactgag ccaaaagaaa tgccggactg gcacttcatc   660
cagcataagc tcaaccgtga agaccgcagc gatgctaaga atcagaaatg caactgata   720
gaacatgcta ttgcatcccg atctgcttta ccctgataac aaaggagttg ctattgcatg   780
tgcatgccta ttacgctgat aaaaatgtag ttttaacatg caattgtatg tgcatgcaca   840
ttaccctgat a                                                        851

<210> SEQ ID NO 6
<211> LENGTH: 231
<212> TYPE: PRT
<213> ORGANISM: Zoanthus sp

<400> SEQUENCE: 6

Met Ala His Ser Lys His Gly Leu Thr Asp Asp Met Thr Met His Phe
1               5                   10                  15

Arg Met Glu Gly Cys Val Asp Gly His Lys Phe Val Ile Glu Gly Asn
            20                  25                  30
```

```
Gly Asn Gly Asn Pro Phe Lys Gly Lys Gln Phe Ile Asn Leu Cys Val
            35                  40                  45

Ile Glu Gly Gly Pro Leu Pro Phe Ser Glu Asp Ile Leu Ser Ala Ala
 50                  55                  60

Phe Asp Tyr Gly Asn Arg Leu Phe Thr Glu Tyr Pro Glu Gly Ile Val
 65                  70                  75                  80

Asp Tyr Phe Lys Asn Ser Cys Pro Ala Gly Tyr Thr Trp His Arg Ser
                85                  90                  95

Phe Arg Phe Glu Asp Gly Ala Val Cys Ile Cys Ser Ala Asp Ile Thr
               100                 105                 110

Val Asn Val Arg Glu Asn Cys Ile Tyr His Glu Ser Thr Phe Tyr Gly
            115                 120                 125

Val Asn Phe Pro Ala Asp Gly Pro Val Met Lys Met Thr Thr Asn
            130                 135                 140

Trp Glu Pro Ser Cys Glu Lys Ile Ile Pro Ile Asn Ser Gln Lys Ile
145                 150                 155                 160

Leu Lys Gly Asp Val Ser Met Tyr Leu Leu Lys Asp Gly Gly Arg
                165                 170                 175

Tyr Arg Cys Gln Phe Asp Thr Ile Tyr Lys Ala Lys Thr Glu Pro Lys
                180                 185                 190

Glu Met Pro Asp Trp His Phe Ile Gln His Lys Leu Asn Arg Glu Asp
                195                 200                 205

Arg Ser Asp Ala Lys Asn Gln Lys Trp Gln Leu Ile Glu His Ala Ile
            210                 215                 220

Ala Ser Arg Ser Ala Leu Pro
225                 230
```

<210> SEQ ID NO 7
<211> LENGTH: 1178
<212> TYPE: DNA
<213> ORGANISM: Scolymia cubensis

<400> SEQUENCE: 7

```
tgtgacattc agtcatatag gagcctctat cggagctgag gtcccattca ccgttgtgat    60
ttggacggga gcagatcgag aacaacmagg gctgtacgag tctgataatt tactttacat   120
ctaccaacat gcagcgtgct gggatgaagg ttaaggaaca tatgaagatc aaactgcgta   180
tgggaggtac tgtaaacgga agcatttcg cggttaatgg acaggagac ggctacccctt   240
atcagggaaa acagattttg aaacttatcg tcgaaggcag cgaacctctg cctttcgctt   300
ttgatatctt gtcagcagca ttccagtatg gcaacagggc attcaccgaa tacccaacag   360
agatagcaga ctatttcaag cagtcgtttg agtttggcga ggggttctcc tgggaacgaa   420
gtttcacttt cgaagatggg gccatttgcg tcgccaccaa cgatataacg atggttggtg   480
gtgagtttca gtatgatatt cgatttgatg gtctgaactt ccctgaagat ggtccagtga   540
tgcaaaagaa aaccgtaaaa tgggagccat ccactgagat aatgtatatg caaaatggag   600
tgctgaaggg tgaggttaac atggctctgt gcttcaaga caaagccat accgttgcg    660
acctcaaaac tacttacaaa gctaagaata atgtgccgca tcctccaggc taccactatg   720
tggatcactg cattgaaata ctcgaagaac gtaaggatca cgttaagctg cgggagcatg   780
ctaaagctcg ttctagcctg tcacctacca gtgcaaaaga acgaaaggct aggtgatag    840
tcaaaaagac aacaagacga aaatgaaagg tgttcattgt tagaatttga tatttcgat    900
tcaatgattc gttaagggat ttgctagagg ctagctaaca ggttaacatc ataaggatag   960
```

```
agattycgtt gcggagttag aaccttwata ttttccgaat tccamctaga gtcgttgaga    1020
aatttattag agactagctt tagagttact tttgtggaaa aaaaggtttc cattttttgc    1080
gttattacag catttaaagc ataggaatag agattcggtt atggaaaata acagtaggaa    1140
aatacgttgt gaaataaac ttgttgtcga aaaaaaaa                            1178
```

<210> SEQ ID NO 8
<211> LENGTH: 234
<212> TYPE: PRT
<213> ORGANISM: Scolymia cubensis

<400> SEQUENCE: 8

```
Met Gln Arg Ala Gly Met Lys Val Lys Glu His Met Lys Ile Lys Leu
  1               5                  10                  15

Arg Met Gly Gly Thr Val Asn Gly Lys His Phe Ala Val Asn Gly Thr
             20                  25                  30

Gly Asp Gly Tyr Pro Tyr Gln Gly Lys Gln Ile Leu Lys Leu Ile Val
         35                  40                  45

Glu Gly Ser Glu Pro Leu Pro Phe Ala Phe Asp Ile Leu Ser Ala Ala
     50                  55                  60

Phe Gln Tyr Gly Asn Arg Ala Phe Thr Glu Tyr Pro Thr Glu Ile Ala
 65                  70                  75                  80

Asp Tyr Phe Lys Gln Ser Glu Phe Gly Glu Gly Phe Ser Trp Glu
                 85                  90                  95

Arg Ser Phe Thr Phe Glu Asp Gly Ala Ile Cys Val Ala Thr Asn Asp
            100                 105                 110

Ile Thr Met Val Gly Gly Glu Phe Gln Tyr Asp Ile Arg Phe Asp Gly
        115                 120                 125

Leu Asn Phe Pro Glu Asp Gly Pro Val Met Gln Lys Thr Val Lys
130                 135                 140

Trp Glu Pro Ser Thr Glu Ile Met Tyr Met Gln Asn Gly Val Leu Lys
145                 150                 155                 160

Gly Glu Val Asn Met Ala Leu Leu Leu Gln Asp Lys Ser His Tyr Arg
                165                 170                 175

Cys Asp Leu Lys Thr Thr Tyr Lys Ala Lys Asn Asn Val Pro His Pro
            180                 185                 190

Pro Gly Tyr His Tyr Val Asp His Cys Ile Glu Ile Leu Glu Glu Arg
        195                 200                 205

Lys Asp His Val Lys Leu Arg Glu His Ala Lys Ala Arg Ser Ser Leu
    210                 215                 220

Ser Pro Thr Ser Ala Lys Glu Arg Lys Ala
225                 230
```

<210> SEQ ID NO 9
<211> LENGTH: 819
<212> TYPE: DNA
<213> ORGANISM: Scolymia cubensis

<400> SEQUENCE: 9

```
cctggtgatt tggacgagag cagatcgaga atagcaaggt tttaccagcg tgataattta     60
ctttacatct aacaacatgc aatctgctgg gaagaagaat gtcgttaagg acttcatgaa    120
gatcacactg cgtatggacg gtgctgtaaa cgggaagccc ttcgcggtta atggaacagg    180
agatggcaac cctatggtg gaatacgag tttgaagctt accgtcgatg caacaaaacc    240
tctgcctttt gcttttgata tcttgtcagc agcattccag tatggcaaca gggcattcac    300
```

-continued

```
cgaataccca aaagagatat cagactattt caagcagtcg tttgagtttg gcgaggggtt    360
tacctgggaa cgaagtttca ctttcgaaga cggggccatt tgcgtcgcca cgaacgatat    420
aaagatggtt ggcgatgagt ttcaatataa cattcgattt gatggtgtga atttccctga    480
agatggtccw gtyatgcaga agaaaacggt gaagtgggag ccatccacag agataatgcg    540
tgtgcaaggt ggagtgctaa aggtgaggt taacatggct ctgttgctta agacaaaag     600 ccattaccga tgtgacttca aaactactta caaagctaag aatcctgtcc cgccgacggc    660
gcttccagac taccactatg tggatcactg tattgaaatc accgaggaaa atagggatta    720
cgttaagctg caggagtatg ctaaagctcg ttctggcctg cacctgcccg aactgcaaaa    780
gtaaaggctt aggcgatagt caagacgaca acgagaaga                          819
```

<210> SEQ ID NO 10
<211> LENGTH: 235
<212> TYPE: PRT
<213> ORGANISM: Scolymia cubensis

<400> SEQUENCE: 10

```
Met Gln Ser Ala Gly Lys Lys Asn Val Val Lys Asp Phe Met Lys Ile
 1               5                  10                  15

Thr Leu Arg Met Asp Gly Ala Val Asn Gly Lys Pro Phe Ala Val Asn
             20                  25                  30

Gly Thr Gly Asp Gly Asn Pro Tyr Gly Gly Ile Gln Ser Leu Lys Leu
         35                  40                  45

Thr Val Asp Gly Asn Lys Pro Leu Pro Phe Ala Phe Asp Ile Leu Ser
     50                  55                  60

Ala Ala Phe Gln Tyr Gly Asn Arg Ala Phe Thr Glu Tyr Pro Lys Glu
 65                  70                  75                  80

Ile Ser Asp Tyr Phe Lys Gln Ser Phe Glu Phe Gly Glu Gly Phe Thr
                 85                  90                  95

Trp Glu Arg Ser Phe Thr Phe Glu Asp Gly Ala Ile Cys Val Ala Thr
            100                 105                 110

Asn Asp Ile Lys Met Val Gly Asp Glu Phe Gln Tyr Asn Ile Arg Phe
        115                 120                 125

Asp Gly Val Asn Phe Pro Glu Asp Gly Pro Val Met Gln Lys Lys Thr
    130                 135                 140

Val Lys Trp Glu Pro Ser Thr Glu Ile Met Arg Val Gln Gly Gly Val
145                 150                 155                 160

Leu Lys Gly Glu Val Asn Met Ala Leu Leu Leu Lys Asp Lys Ser His
                165                 170                 175

Tyr Arg Cys Asp Phe Lys Thr Thr Tyr Lys Ala Lys Asn Pro Val Pro
            180                 185                 190

Pro Thr Ala Leu Pro Asp Tyr His Tyr Val Asp His Cys Ile Glu Ile
        195                 200                 205

Thr Glu Glu Asn Arg Asp Tyr Val Lys Leu Gln Glu Tyr Ala Lys Ala
    210                 215                 220

Arg Ser Gly Leu His Leu Pro Glu Leu Gln Lys
225                 230                 235
```

<210> SEQ ID NO 11
<211> LENGTH: 807
<212> TYPE: DNA
<213> ORGANISM: Ricordea florida

<400> SEQUENCE: 11

```
tgtgaaagtt aacattttac tttacttcta ccagcatgag tgcactcaaa gaggaaatga    60
aaatcaagct tacattggtg ggcgttgtta acgggcaccc attcaagatc attggggacg   120
gaaaaggcaa acccatgag ggatcgcagg aattaaccct tgccgtggtg aaggagggc    180 ctctgccttt ctcttatgat atcctgacaa cgatagttca ctatggcaac agggcatttg   240
tgaactaccc aaaggacata ccagatattt tcaagcagac tgctctggt cctggtgctg    300 gatattcctg gcaaaggacc atgagttttg aagacggagg cgtttgcact gctacgagcc   360
atatcagggt ggatggcgac actttcaatt atgacattca cttcatggga gcggatttcc   420
ctcttaatgg tccagtgatg cagaaaagaa cagtgaaatg ggagccatcc actgagataa    480
tgtttcaatg tgatggattg ctgaggggtg atgttgccat gtctctgttg ctgaaaggag   540
gcggccatta ccgatgtgac tttaaaacta tttataaacc aagaagaat gtcaagatgc    600 caggttacca ttttgtggac cactgcattg agataacgag tcaacaggac gattacaacg   660
tggttgagct gtacgagggt gctgtagccc actactctcc tctgcagaaa ccatgccaag   720
caaaggcata agccaaaca acccaagagg acaacaagac atttaatcaa atcacatctt    780
tgtatttttg gttagagttg aaaaaaa                                      807
```

<210> SEQ ID NO 12
<211> LENGTH: 231
<212> TYPE: PRT
<213> ORGANISM: Ricordea florida

<400> SEQUENCE: 12

```
Met Ser Ala Leu Lys Glu Glu Met Lys Ile Lys Leu Thr Leu Val Gly
  1               5                  10                  15

Val Val Asn Gly His Pro Phe Lys Ile Ile Gly Asp Gly Lys Gly Lys
                 20                  25                  30

Pro Tyr Glu Gly Ser Gln Glu Leu Thr Leu Ala Val Val Glu Gly Gly
             35                  40                  45

Pro Leu Pro Phe Ser Tyr Asp Ile Leu Thr Thr Ile Val His Tyr Gly
         50                  55                  60

Asn Arg Ala Phe Val Asn Tyr Pro Lys Asp Ile Pro Asp Ile Phe Lys
 65                  70                  75                  80

Gln Thr Cys Ser Gly Pro Gly Ala Gly Tyr Ser Trp Gln Arg Thr Met
                 85                  90                  95

Ser Phe Glu Asp Gly Gly Val Cys Thr Ala Thr Ser His Ile Arg Val
                100                 105                 110

Asp Gly Asp Thr Phe Asn Tyr Asp Ile His Phe Met Gly Ala Asp Phe
            115                 120                 125

Pro Leu Asn Gly Pro Val Met Gln Lys Arg Thr Val Lys Trp Glu Pro
        130                 135                 140

Ser Thr Glu Ile Met Phe Gln Cys Asp Gly Leu Leu Arg Gly Asp Val
145                 150                 155                 160

Ala Met Ser Leu Leu Leu Lys Gly Gly Gly His Tyr Arg Cys Asp Phe
                165                 170                 175

Lys Thr Ile Tyr Lys Pro Lys Lys Asn Val Lys Met Pro Gly Tyr His
            180                 185                 190

Phe Val Asp His Cys Ile Glu Ile Thr Ser Gln Gln Asp Asp Tyr Asn
        195                 200                 205

Val Val Glu Leu Tyr Glu Gly Ala Val Ala His Tyr Ser Pro Leu Gln
    210                 215                 220
```

```
Lys Pro Cys Gln Ala Lys Ala
225                 230
```

<210> SEQ ID NO 13
<211> LENGTH: 796
<212> TYPE: DNA
<213> ORGANISM: Ricordea florida

<400> SEQUENCE: 13

```
agtcacctcg gtgtttttag gacaggaagg atcacgagca agagaagaac tgtgaaagtt      60
aacactttac tctacttcta ccagcatgag tgcactcaaa gaggaaatga aaatcaagct     120
taaaatggtg ggcgttgtta acgggcagtc atttcagatc gatggggaag gaaaaggcaa     180
accttacgag ggatcacaga aattaaccct tgaagtggtg gaaggagggc ctctgctctt     240
ctcttatgat atcctgacaa cgatatttca gtatggcaac agggcattcg tgaactaccc     300
aaaggacata ccagatattt tcaagcagac ctgctctggt cctgatggtg gattttcctg     360
gcaaaggacc atgacttatg aagacggagg ggtttgcact gcttcaaacc acatcagcgt     420
ggacggcgac actttttatt atgtgataag atttaatgga gagaattttc ctccaaatgg     480
tccagtaatg cagaaaagaa cagtgaaatg ggagccatcc actgagataa tgtttgaacg     540
tgatggattg ctgaggggtg acattgccat gtctctgttg ctgaaaggag gcggccatta     600
ccgatgtgac tttaaaacta tttatacacc caagaggaag gtcaacatgc aggttacca     660
ttttgtggac cactgcattg agatacagaa gcacgacaag gattacaaca tggctgtgct     720
ctctgaggat gctgtagccc acaactctcc tctggagaaa aaagccaag caaaggcgta     780
aagccaaaca acctaa                                                      796
```

<210> SEQ ID NO 14
<211> LENGTH: 231
<212> TYPE: PRT
<213> ORGANISM: Ricordea florida

<400> SEQUENCE: 14

```
Met Ser Ala Leu Lys Glu Glu Met Lys Ile Lys Leu Lys Met Val Gly
1               5                   10                  15
Val Val Asn Gly Gln Ser Phe Gln Ile Asp Gly Glu Gly Lys Gly Lys
                20                  25                  30
Pro Tyr Glu Gly Ser Gln Lys Leu Thr Leu Glu Val Val Glu Gly Gly
            35                  40                  45
Pro Leu Leu Phe Ser Tyr Asp Ile Leu Thr Thr Ile Phe Gln Tyr Gly
        50                  55                  60
Asn Arg Ala Phe Val Asn Tyr Pro Lys Asp Ile Pro Asp Ile Phe Lys
65                  70                  75                  80
Gln Thr Cys Ser Gly Pro Asp Gly Gly Phe Ser Trp Gln Arg Thr Met
                85                  90                  95
Thr Tyr Glu Asp Gly Gly Val Cys Thr Ala Ser Asn His Ile Ser Val
            100                 105                 110
Asp Gly Asp Thr Phe Tyr Tyr Val Ile Arg Phe Asn Gly Glu Asn Phe
        115                 120                 125
Pro Pro Asn Gly Pro Val Met Gln Lys Arg Thr Val Lys Trp Glu Pro
    130                 135                 140
Ser Thr Glu Ile Met Phe Glu Arg Asp Gly Leu Leu Arg Gly Asp Ile
145                 150                 155                 160
Ala Met Ser Leu Leu Leu Lys Gly Gly Gly His Tyr Arg Cys Asp Phe
                165                 170                 175
```

```
Lys Thr Ile Tyr Thr Pro Lys Arg Lys Val Asn Met Pro Gly Tyr His
            180                 185                 190

Phe Val Asp His Cys Ile Glu Ile Gln Lys His Asp Lys Asp Tyr Asn
            195                 200                 205

Met Ala Val Leu Ser Glu Asp Ala Val Ala His Asn Ser Pro Leu Glu
    210                 215                 220

Lys Lys Ser Gln Ala Lys Ala
225                 230

<210> SEQ ID NO 15
<211> LENGTH: 795
<212> TYPE: DNA
<213> ORGANISM: Montastraea cavernosa

<400> SEQUENCE: 15
acgcagggat tcaccctggt gatttggaag agagcagacc gagaacaaca agagctgtat      60
aaggctgata tcttacttta cgtctaccat catgagtgtg attaaatcag tcatgaagat     120
caagctgcgt atggaaggca gtgtaaacgg cacaacttc gtaattgttg gagaaggaga      180
aggcaagcct tatgagggaa cacagagtat ggaccttaca gtcaaagaag gcgcacctct     240
gcctttcgcc tacgatatca tgacaacagt attccattac ggcaataggg tattcgcaaa     300
atacccaaaa catatcccag actatttcaa gcagatgttt cctgaggagt attcctggga     360
acgaagcatg aatttcgaag gcgggggcat ttgcaccgcc aggaacgaga taacaatgga     420
aggcgactgt tttttcaata agttcgatt tgatggtgtg aacttccccc ccaatggtcc      480
agtcatgcag aagaagacgc tgaaatggga gccatccact gaaaaaatgt atgtgcgtga     540
tggagtgctg acgggtgata tcaacatggc tttgttgctt gaaggaggtg gccattaccg     600
atgtgacttc agaactactt acagagctaa gaagaagggt gtcaagttac agattatca     660 ctttgaggat cactccattg agattttgcg ccatgacaaa gaatacactg aggttaagct     720
gtatgagcat gccgaagctc attctgggct gccgagggtg gcaaagtaaa ggcttaacga     780
aaagccaaga ccaca                                                      795

<210> SEQ ID NO 16
<211> LENGTH: 235
<212> TYPE: PRT
<213> ORGANISM: Montastraea cavernosa

<400> SEQUENCE: 16

Arg Leu Ile Ser Tyr Phe Thr Ser Thr Ile Met Ser Val Ile Lys Ser
1               5                  10                  15

Val Met Lys Ile Lys Leu Arg Met Glu Gly Ser Val Asn Gly His Asn
            20                  25                  30

Phe Val Ile Val Gly Glu Gly Glu Gly Lys Pro Tyr Glu Gly Thr Gln
        35                  40                  45

Ser Met Asp Leu Thr Val Lys Glu Gly Ala Pro Leu Pro Phe Ala Tyr
    50                  55                  60

Asp Ile Met Thr Thr Val Phe His Tyr Gly Asn Arg Val Phe Ala Lys
65                  70                  75                  80

Tyr Pro Lys His Ile Pro Asp Tyr Phe Lys Gln Met Phe Pro Glu Glu
                85                  90                  95

Tyr Ser Trp Glu Arg Ser Met Asn Phe Glu Gly Gly Gly Ile Cys Thr
            100                 105                 110

Ala Arg Asn Glu Ile Thr Met Glu Gly Asp Cys Phe Phe Asn Lys Val
```

```
                 115                 120                 125
Arg Phe Asp Gly Val Asn Phe Pro Pro Asn Gly Pro Val Met Gln Lys
    130                 135                 140

Lys Thr Leu Lys Trp Glu Pro Ser Thr Glu Lys Met Tyr Val Arg Asp
145                 150                 155                 160

Gly Val Leu Thr Gly Asp Ile Asn Met Ala Leu Leu Leu Glu Gly Gly
                165                 170                 175

Gly His Tyr Arg Cys Asp Phe Arg Thr Thr Tyr Arg Ala Lys Lys Lys
            180                 185                 190

Gly Val Lys Leu Pro Asp Tyr His Phe Glu Asp His Ser Ile Glu Ile
        195                 200                 205

Leu Arg His Asp Lys Glu Tyr Thr Glu Val Lys Leu Tyr Glu His Ala
    210                 215                 220

Glu Ala His Ser Gly Leu Pro Arg Val Ala Lys
225                 230                 235

<210> SEQ ID NO 17
<211> LENGTH: 1066
<212> TYPE: DNA
<213> ORGANISM: Montastraea cavernosa

<400> SEQUENCE: 17
attcgccctg gtgatttgga agagagcaga tcgagaacaa caagagctgt aaggttgata      60
tcttacttac gtctaccatc atgacaagtg ttgcacagga aaagggtgtg attaaaccag     120
acatgaagat gaagctgcgt atggaaggtg ctgtaaacgg gcacaagttc gtggttgaag     180
gagatggaaa agggaagcct ttcgacggaa cacagactat ggaccttaca gtcatagaag     240
gcgcaccatt gcctttcgct tacgatatct tgacaacagt attcgattac ggcaacaggg     300
tattcgccaa atacccagaa gacatagcag attatttcaa gcagacgttt cctgaggggt     360
acttctggga acgaagcatg acatacgaag accagggcat tgcatcgcc acaaacgaca     420
taacaatgat ggaaggcgtc gacgactgtt ttgcctataa aattcgattt gatggtgtga     480
actttcctgc caatggtcca gttatgcaga ggaagacgct gaaatgggag ccatccactg     540
agataatgta tgcgcgtgat ggagtgctga agggtgatgt taacatggct ctgttgcttg     600
aaggaggtgg ccattaccga tgtgacttca aaactactta caaagctaag aaggttgtcc     660
ggttgccaga ctatcacttt gtggaccatc gcattgagat tgtgagccac gacaaagatt     720
acaacaaggt taagctgcac gagcatgccg aagctcgtca tggactgtca aggaaggcca     780
agtaaaggct taatgaaaag tcaagacgac aacgaggaga acaaagtac tttttttgtta     840
aatttgaagg catttactcg gaattagtat ttgatacttt cgattcaagg atttgttccg     900
ggatttgtta gagactagct ctagagttgt attttgtgaa aaaagatagt ttccagtttt     960
tgcgggatta cagcatgggg atagactttt taaactcagt tgtggtcaaa tgcaagtaag    1020
aaaactgtag tgagaataaa cttgttatcg aagccgaaaa aaaaaa                    1066

<210> SEQ ID NO 18
<211> LENGTH: 234
<212> TYPE: PRT
<213> ORGANISM: Montastraea cavernosa

<400> SEQUENCE: 18

Met Thr Ser Val Ala Gln Glu Lys Gly Val Ile Lys Pro Asp Met Lys
1               5                   10                  15

Met Lys Leu Arg Met Glu Gly Ala Val Asn Gly His Lys Phe Val Val
```

-continued

```
                    20                  25                  30
Glu Gly Asp Gly Lys Gly Lys Pro Phe Asp Gly Thr Gln Thr Met Asp
     35                  40                  45

Leu Thr Val Ile Glu Gly Ala Pro Leu Pro Phe Ala Tyr Asp Ile Leu
 50                  55                  60

Thr Thr Val Phe Asp Tyr Gly Asn Arg Val Phe Ala Lys Tyr Pro Glu
 65                  70                  75                  80

Asp Ile Ala Asp Tyr Phe Lys Gln Thr Phe Pro Glu Gly Tyr Phe Trp
                 85                  90                  95

Glu Arg Ser Met Thr Tyr Glu Asp Gln Gly Ile Cys Ile Ala Thr Asn
            100                 105                 110

Asp Ile Thr Met Met Glu Gly Val Asp Asp Cys Phe Ala Tyr Lys Ile
            115                 120                 125

Arg Phe Asp Gly Val Asn Phe Pro Ala Asn Gly Pro Val Met Gln Arg
            130                 135                 140

Lys Thr Leu Lys Trp Glu Pro Ser Thr Glu Ile Met Tyr Ala Arg Asp
145                 150                 155                 160

Gly Val Leu Lys Gly Asp Val Asn Met Ala Leu Leu Glu Gly Gly
                165                 170                 175

Gly His Tyr Arg Cys Asp Phe Lys Thr Thr Tyr Lys Ala Lys Lys Val
            180                 185                 190

Val Arg Leu Pro Asp Tyr His Phe Val Asp His Arg Ile Glu Ile Val
            195                 200                 205

Ser His Asp Lys Asp Tyr Asn Lys Val Lys Leu His Glu His Ala Glu
        210                 215                 220

Ala Arg His Gly Leu Ser Arg Lys Ala Lys
225                 230
```

<210> SEQ ID NO 19
<211> LENGTH: 898
<212> TYPE: DNA
<213> ORGANISM: Condylactis gigantea

<400> SEQUENCE: 19

```
acagctgttc atccacgctc attcaagacg ccgtcaactt tattccagtc aggaaaatgt    60
atccttggat caaggaaacc atgcgcagta aggtttacat ggaaggagat gttaacaacc   120
acgccttcaa gtgcactgca gtaggagaag gaaaaccata caaggctcaa caagacctga   180
cgattaccgt cactgaagga ggtcctctgc catttgcttt cgacattctt tcacacgcct   240
ttcagtatgg caacaaggtg ttcaccgatt accccgacga tattcctgat ttctttaagc   300
agtctctctc ggatggtttt acttggagaa gagtaagcac statgacgat ggaggagtcc   360
tcacagttac ccaagacact agtctgaagg agattgcat tatttgcaac attaaagtcc   420
atggcactaa cttccccgaa atggtccgg tgatgcaaaa caagaccgat ggatgggagc   480
catccagcac tgaaacggtt attccacaag atggaggaat tgttgctgcg cgatcacccg   540
cactaaggct gcgtgataaa ggtcatctta tctgccacat ggaaacaact tacaagccaa   600
acaaagaggt gaagctgcca gaactccact tcatcatttt gcgaatggaa aagctgagtg   660
ttagtgacga tgggaagacc attaagcagc acgagtatgt ggtggctagc tactccaaag   720
tgccttcgaa gataggacgt caatgatcat ttcccttatt aaatatcaat gatgtggctt   780
tcaattttcc aaaattttgt taagacatag gtcttttgga ttttggtaa ccccaacctt   840
aattcccaat aattttttgtt ggaaagtcaa ataaaaccag ccttccctgg gcctttaa    898
```

<210> SEQ ID NO 20
<211> LENGTH: 229
<212> TYPE: PRT
<213> ORGANISM: Condylactis gigantea

<400> SEQUENCE: 20

| | | | | | | | | | | | | | | | |
|---|---|---|---|---|---|---|---|---|---|---|---|---|---|---|---|
| Met | Tyr | Pro | Trp | Ile | Lys | Glu | Thr | Met | Arg | Ser | Lys | Val | Tyr | Met | Glu |
| 1 | | | | 5 | | | | | 10 | | | | | 15 | |
| Gly | Asp | Val | Asn | Asn | His | Ala | Phe | Lys | Cys | Thr | Ala | Val | Gly | Glu | Gly |
| | | | 20 | | | | | 25 | | | | | 30 | | |
| Lys | Pro | Tyr | Lys | Gly | Ser | Gln | Asp | Leu | Thr | Ile | Thr | Val | Thr | Glu | Gly |
| | | | 35 | | | | 40 | | | | | 45 | | | |
| Gly | Pro | Leu | Pro | Phe | Ala | Phe | Asp | Ile | Leu | Ser | His | Ala | Phe | Gln | Tyr |
| | 50 | | | | | 55 | | | | | 60 | | | | |
| Gly | Asn | Lys | Val | Phe | Thr | Asp | Tyr | Pro | Asp | Asp | Ile | Pro | Asp | Phe | Phe |
| 65 | | | | | 70 | | | | | 75 | | | | | 80 |
| Lys | Gln | Ser | Leu | Ser | Asp | Gly | Phe | Thr | Trp | Arg | Arg | Val | Ser | Thr | Tyr |
| | | | | 85 | | | | | 90 | | | | | 95 | |
| Asp | Asp | Gly | Gly | Val | Leu | Thr | Val | Thr | Gln | Asp | Thr | Ser | Leu | Lys | Gly |
| | | | 100 | | | | | 105 | | | | | 110 | | |
| Asp | Cys | Ile | Ile | Cys | Asn | Ile | Lys | Val | His | Gly | Thr | Asn | Phe | Pro | Glu |
| | | 115 | | | | | 120 | | | | | 125 | | | |
| Asn | Gly | Pro | Val | Met | Gln | Asn | Lys | Thr | Asp | Gly | Trp | Glu | Pro | Ser | Ser |
| | 130 | | | | | 135 | | | | | 140 | | | | |
| Thr | Glu | Thr | Val | Ile | Pro | Gln | Asp | Gly | Gly | Ile | Val | Ala | Ala | Arg | Ser |
| 145 | | | | | 150 | | | | | 155 | | | | | 160 |
| Pro | Ala | Leu | Arg | Leu | Arg | Asp | Lys | Gly | His | Leu | Ile | Cys | His | Met | Glu |
| | | | | 165 | | | | | 170 | | | | | 175 | |
| Thr | Thr | Tyr | Lys | Pro | Asn | Lys | Glu | Val | Lys | Leu | Pro | Glu | Leu | His | Phe |
| | | | 180 | | | | | 185 | | | | | 190 | | |
| His | His | Leu | Arg | Met | Glu | Lys | Leu | Ser | Val | Ser | Asp | Asp | Gly | Lys | Thr |
| | | 195 | | | | | 200 | | | | | 205 | | | |
| Ile | Lys | Gln | His | Glu | Tyr | Val | Val | Ala | Ser | Tyr | Ser | Lys | Val | Pro | Ser |
| | 210 | | | | | 215 | | | | | 220 | | | | |
| Lys | Ile | Gly | Arg | Gln | | | | | | | | | | | |
| 225 | | | | | | | | | | | | | | | |

<210> SEQ ID NO 21
<211> LENGTH: 1030
<212> TYPE: DNA
<213> ORGANISM: Agaricia fragilis

<400> SEQUENCE: 21

| | |
|---|---|
| caaggaagcc aaatctttta ccagagatct cgcgtgaaag caacctatga gtgatggcga | 60 |
| tttctactct aaagaacgtc atcatcatcg ttattatata ctcctgcagc acttgtgctg | 120 |
| tttggtcgaa ttcaaactct gaatcctctt tcactaatgg gattgcagag gaaatgaaga | 180 |
| ctagggtaca tttggagggt actgttaacg ggcactcctt tacaattaaa ggcgaaggaa | 240 |
| gaggctaccc ttacaaagga gaacagttta tgagccttga ggtcgtcaat ggtgctcctc | 300 |
| tgccgttctc ttttgatatc ttgacaccag catttatgta tggcaacaga gtgttccaca | 360 |
| agtacccacc aaacatacca gactatttca agcagacgtt tcctgaaggg tatcactggg | 420 |
| aaagaaacat tccctttgaa gatcaggccg cgtgcacggt aaccagccac ataagattgg | 480 |
| aagaggaaga gaggcgtttt gtaaatacg tcagatttca ctgtgtgaac tttccccta | 540 |

```
atggtccagt catgcagagg aggatactga aatgggagcc atccactgag aacatttatc    600
cgcgtgatgg gtttctggag ggccatgttg atatgactct tcgggttgaa ggaggtggct    660
attaccgagc tgagttcaaa agtacttaca aagggaagac cccagtccgc gacatgccag    720
actttcactt catagaccac cgcattgaga ttacggagca tgacgaagac tacaccaatg    780
ttgagctgca tgacgtatcc tgggctcgtt actctatgct gccgactatg taagcggaaa    840
aggcaaggca acaagacgca aaaccgccct gtttgtctct tttcataaga gatttgacaa    900
ccgtggttct ttgccattta atttgaatta gtttaaatta aatctttggg attgatgtag    960
acgctttggt tgctaagtaa gaaaacattt gtgattatta aatttgttgc ctgaagcaaa   1020
aaaaaaaaaa                                                          1030
```

<210> SEQ ID NO 22
<211> LENGTH: 259
<212> TYPE: PRT
<213> ORGANISM: Agaricia fragilis

<400> SEQUENCE: 22

```
Met Ala Ile Ser Thr Leu Lys Asn Val Ile Ile Val Ile Ile Tyr
  1               5                  10                  15
Ser Cys Ser Thr Cys Ala Val Trp Ser Asn Ser Asn Ser Glu Ser Ser
                 20                  25                  30
Phe Thr Asn Gly Ile Ala Glu Glu Met Lys Thr Arg Val His Leu Glu
             35                  40                  45
Gly Thr Val Asn Gly His Ser Phe Thr Ile Lys Gly Glu Gly Arg Gly
 50                  55                  60
Tyr Pro Tyr Lys Gly Glu Gln Phe Met Ser Leu Glu Val Val Asn Gly
 65                  70                  75                  80
Ala Pro Leu Pro Phe Ser Phe Asp Ile Leu Thr Pro Ala Phe Met Tyr
                 85                  90                  95
Gly Asn Arg Val Phe Thr Lys Tyr Pro Pro Asn Ile Pro Asp Tyr Phe
            100                 105                 110
Lys Gln Thr Phe Pro Glu Gly Tyr His Trp Glu Arg Asn Ile Pro Phe
         115                 120                 125
Glu Asp Gln Ala Ala Cys Thr Val Thr Ser His Ile Arg Leu Glu Glu
130                 135                 140
Glu Glu Arg Arg Phe Val Asn Asn Val Arg Phe His Cys Val Asn Phe
145                 150                 155                 160
Pro Pro Asn Gly Pro Val Met Gln Arg Ile Leu Lys Trp Glu Pro
                165                 170                 175
Ser Thr Glu Asn Ile Tyr Pro Arg Asp Gly Phe Leu Glu Gly His Val
            180                 185                 190
Asp Met Thr Leu Arg Val Glu Gly Gly Tyr Tyr Arg Ala Glu Phe
         195                 200                 205
Lys Ser Thr Tyr Lys Gly Lys Thr Pro Val Arg Asp Met Pro Asp Phe
    210                 215                 220
His Phe Ile Asp His Arg Ile Glu Ile Thr Glu His Asp Glu Asp Tyr
225                 230                 235                 240
Thr Asn Val Glu Leu His Asp Val Ser Trp Ala Arg Tyr Ser Met Leu
                245                 250                 255
Pro Thr Met
```

<210> SEQ ID NO 23
<211> LENGTH: 1024

<210> TYPE: DNA
<213> ORGANISM: Ricordea florida

<400> SEQUENCE: 23

```
agccacttcg gtgtcttgtc gagaggaagg atcacgaaca agagaagagc tgtaaaagtt      60
aaaatttac  tttacttctt ccagcatgaa tgcacttcaa gaggaaatga aaatcaagct     120
tacaatggtg gcgttgtta  acgggcagtc atttaagatc gatgggaaag gaaaagggaa     180
accttacgag ggatcacagg aattgaccct aaagtggtg  gaaggcgggc tctgctctt      240
ctcttatgat atcctgacaa cgatatttca gtatggcaac agggcattcg tgaactaccc     300
aaaggacata ccagatattt tcaagcaaac gtgttctggt cttgatggcg gatattcgtg     360
gcaaaggacc atgacttatg aggacggagg ggtttgtact gctacaagca acgtcagcgt     420
ggtcggcgac actttcaatt atgaaattca ctttatgggg gcgaattttc ctccaaatgg     480
tccrgtgatg cagaaaagaa cagtgaagtg ggagccctcc actgagataa tgtttgaacg     540
tgatggattg ctgaggggtg atgttcccat gtctctgttg ctgaaaggag gcgaccatta     600
ccgatgtgac tttaaaacta tttataaacc caacaagaag gtcaagctgc aggttacca     660
ttttgtggac cactgcattg agataaagag tcaagagaat gattacaaca tggttgcgct     720
ctttgaggat gctgtagcac actactctcc tctggagaaa aagagccagg caaaggcgta     780
aatccaaaca acctaagaag acgacaaggc attcaatcta atcgcatgtt tgaattttg      840
gttaggaatg tgtttgggtca gactaggtct agaacgtttc attttggctg gatttgtttt    900
actcagttat agacaagaaa aaaatcttaa atgacttggg ttggatttag ctttcggcac     960
tgtcaattcc ggattcctta gaaatatttg agaccaagcc ttttttttgag ctgagaacgt    1020
aatc                                                                  1024
```

<210> SEQ ID NO 24
<211> LENGTH: 231
<212> TYPE: PRT
<213> ORGANISM: Ricordea florida

<400> SEQUENCE: 24

```
Met Asn Ala Leu Gln Glu Glu Met Lys Ile Lys Leu Thr Met Val Gly
  1               5                  10                  15
Val Val Asn Gly Gln Ser Phe Lys Ile Asp Gly Lys Gly Lys Gly Lys
             20                  25                  30
Pro Tyr Glu Gly Ser Gln Glu Leu Thr Leu Lys Val Val Glu Gly Gly
         35                  40                  45
Pro Leu Leu Phe Ser Tyr Asp Ile Leu Thr Thr Ile Phe Gln Tyr Gly
     50                  55                  60
Asn Arg Ala Phe Val Asn Tyr Pro Lys Asp Ile Pro Asp Ile Phe Lys
 65                  70                  75                  80
Gln Thr Cys Ser Gly Leu Asp Gly Gly Tyr Ser Trp Gln Arg Thr Met
                 85                  90                  95
Thr Tyr Glu Asp Gly Gly Val Cys Thr Ala Thr Ser Asn Val Ser Val
            100                 105                 110
Val Gly Asp Thr Phe Asn Tyr Glu Ile His Phe Met Gly Ala Asn Phe
        115                 120                 125
Pro Pro Asn Gly Pro Val Met Gln Lys Arg Thr Val Lys Trp Glu Pro
    130                 135                 140
Ser Thr Glu Ile Met Phe Glu Arg Asp Gly Leu Leu Arg Gly Asp Val
145                 150                 155                 160
```

```
Pro Met Ser Leu Leu Lys Gly Gly Asp His Tyr Arg Cys Asp Phe
            165                 170                 175

Lys Thr Ile Tyr Lys Pro Asn Lys Val Lys Leu Pro Gly Tyr His
            180                 185                 190

Phe Val Asp His Cys Ile Glu Ile Lys Ser Gln Glu Asn Asp Tyr Asn
            195                 200                 205

Met Val Ala Leu Phe Glu Asp Ala Val Ala His Tyr Ser Pro Leu Glu
            210                 215                 220

Lys Lys Ser Gln Ala Lys Ala
225             230

<210> SEQ ID NO 25
<211> LENGTH: 913
<212> TYPE: DNA
<213> ORGANISM: Montastraea cavernosa

<400> SEQUENCE: 25
```

| | | | | | |
|---|---|---|---|---|---|
| agagctgtag | ggtgatatct | tacttacgtc | taccatcatg | accagtgttg | cacaggaaaa | 60 |
| gggtgtgatt | aaaccagaca | tgaagatgaa | gctgcgtatg | gaaggtgctg | taaacgggca | 120 |
| caagttcgtg | attgaaggag | atggaaaagg | gaagcctttc | gacggaacac | agactatgga | 180 |
| ccttacagtc | atagaaggcg | caccattgcc | tttcgcttac | gctatcttga | caacagtatt | 240 |
| cgattacggc | aacagggtat | tcgccaaata | cccagaagac | atagcagatt | atttcaagca | 300 |
| gacatttcct | gagggtact | tctgggaacg | aagcatgaca | tacgaagacc | agggcatttg | 360 |
| catcgccaca | acgacataa | caatgatgaa | aggcgtcgac | gactgttttg | tctataaaat | 420 |
| tcgatttgat | ggtgtgaact | ttcctgccaa | tggtccagtt | atgcagagga | agacgctgaa | 480 |
| atgggagcca | tccactgaga | aaatgtatgc | gcgtgatgga | gtgctgaagg | gtgatgttaa | 540 |
| catggctctg | ttgcttgaag | gaggtggcca | ttaccgatgt | gacttcaaaa | ctacttacag | 600 |
| agctaagaag | gttgtccagt | tgccagacta | tcattttgtg | gaccatcgca | ttgagattgt | 660 |
| gagccacgac | aaagattaca | acaaggttaa | gctgtatgag | catgccgaag | ctcattctgg | 720 |
| gctgccgagg | caggccaagt | aaaggcttaa | tgaaaagcca | agacgacaac | aaggagaaac | 780 |
| aaagtatttt | ttttgttaaa | tttcaaggca | tttactcgga | attagtattt | gatactttcg | 840 |
| attcaaggat | ttgtttcggg | acttgttaga | gaccagctct | agagttgtat | tttgtgaaaa | 900 |
| aaagatagtt | tcc | | | | | 913 |

```
<210> SEQ ID NO 26
<211> LENGTH: 234
<212> TYPE: PRT
<213> ORGANISM: Montastraea cavernosa

<400> SEQUENCE: 26

Met Thr Ser Val Ala Gln Glu Lys Gly Val Ile Lys Pro Asp Met Lys
1               5                   10                  15

Met Lys Leu Arg Met Glu Gly Ala Val Asn Gly His Lys Phe Val Ile
            20                  25                  30

Glu Gly Asp Gly Lys Gly Lys Pro Phe Asp Gly Thr Gln Thr Met Asp
        35                  40                  45

Leu Thr Val Ile Glu Gly Ala Pro Leu Pro Phe Ala Tyr Ala Ile Leu
    50                  55                  60

Thr Thr Val Phe Asp Tyr Gly Asn Arg Val Phe Ala Lys Tyr Pro Glu
65                  70                  75                  80

Asp Ile Ala Asp Tyr Phe Lys Gln Thr Phe Pro Glu Gly Tyr Phe Trp
```

```
              85                  90                  95
Glu Arg Ser Met Thr Tyr Glu Asp Gln Gly Ile Cys Ile Ala Thr Asn
            100                 105                 110
Asp Ile Thr Met Met Lys Gly Val Asp Asp Cys Phe Val Tyr Lys Ile
        115                 120                 125
Arg Phe Asp Gly Val Asn Phe Pro Ala Asn Gly Pro Val Met Gln Arg
    130                 135                 140
Lys Thr Leu Lys Trp Glu Pro Ser Thr Glu Lys Met Tyr Ala Arg Asp
145                 150                 155                 160
Gly Val Leu Lys Gly Asp Val Asn Met Ala Leu Leu Leu Glu Gly Gly
                165                 170                 175
Gly His Tyr Arg Cys Asp Phe Lys Thr Thr Tyr Arg Ala Lys Lys Val
            180                 185                 190
Val Gln Leu Pro Asp Tyr His Phe Val Asp His Arg Ile Glu Ile Val
        195                 200                 205
Ser His Asp Lys Asp Tyr Asn Lys Val Lys Leu Tyr Glu His Ala Glu
    210                 215                 220
Ala His Ser Gly Leu Pro Arg Gln Ala Lys
225                 230

<210> SEQ ID NO 27
<211> LENGTH: 1133
<212> TYPE: DNA
<213> ORGANISM: Montastraea annularis

<400> SEQUENCE: 27
tggttaacgc agagtcgcgg ggggttcctg gctaataatt gattctatttt tgggtgtgac      60
attcaggttt aaagcagcat cctcagtgct gaggtctcat tcaccctggt gatttggaag     120
agagcagatc gagaacacca gagctgtat tacgctaaaa tcttacttgc ctctaccacc     180
atgagtatga ttaaaccaga aatgaagatc aagatgcgta tggacggtgc tgtaaacggg     240
cacaagttcg tgattacagg ggaaggaagc ggcgagcctt cgagggaaa acagactatg     300
aacctgacag tcatagacgg cggacctctg cctttcgctt cgacatcctt gacaacagca     360
ttcgattacg gcamcagggt attcgccaaa tacccagaag acatcccaga ctatttcaag     420
cagtcgtttc ctgagggggtt ttcttgggaa cgaagcatga cttacgaaga cgggggcatt     480
tgcatcgcca caaatgacat aaaaatggaa ggcgactgct tttcctatga aattcgattt     540
gatgggggtga ctttcctgc caatagtcca gttatgcaga agaagaccgt gaaatgggag     600
ccatgcactg rggaaatgta tgtgcgtgat ggagtgctta aggtggtct aacatggct     660
ctgttgcttg aaggaggtgg ccatttccga tgtgacttga aaactactta caaagctaag     720
aaggttgtcc agatgccaga ctatcacttt gtgaatcacc gacttgagat aacatggcat     780
gacgaggatt acaacaatgt taagctgtct gagcatgcag aagctcattc tggactgcca     840
aggcaggcca ataaaggct tgacgaaaag ccaaaacggc aaagagtaca agaaagtata     900
tataaatgta tattttttcaa ctgaaaggca ttccactcgg aattagtatt tgatactttc     960
aattcaagga tttatttggg gatttgctag ccactagctt tattgttaaa ttaagttaaa    1020
gacggtttag cattttttcg gtattacaac ataggcacag acgtcttaac cccagtagtg    1080
gtcaggtaca agtaagaaaa ctttggtgag aatagacttg tagtcgaaaa aaa           1133

<210> SEQ ID NO 28
<211> LENGTH: 224
<212> TYPE: PRT
```

-continued

```
<213> ORGANISM: Montastraea annularis
<220> FEATURE:
<221> NAME/KEY: VARIANT
<222> LOCATION: 65, 144
<223> OTHER INFORMATION: Xaa = Any Amino Acid

<400> SEQUENCE: 28

Met Ser Met Ile Lys Pro Glu Met Lys Ile Lys Met Arg Met Asp Gly
 1               5                  10                  15

Ala Val Asn Gly His Lys Phe Val Ile Thr Gly Glu Gly Ser Gly Glu
                20                  25                  30

Pro Phe Glu Gly Lys Gln Thr Met Asn Leu Thr Val Ile Asp Gly Gly
            35                  40                  45

Pro Leu Pro Phe Ala Phe Asp Ile Leu Thr Thr Ala Phe Asp Tyr Gly
    50                  55                  60

Xaa Arg Val Phe Ala Lys Tyr Pro Glu Asp Ile Pro Asp Tyr Phe Lys
65                  70                  75                  80

Gln Ser Phe Pro Glu Gly Phe Ser Trp Glu Arg Ser Met Thr Tyr Glu
                85                  90                  95

Asp Gly Gly Ile Cys Ile Ala Thr Asn Asp Ile Lys Met Glu Gly Asp
            100                 105                 110

Cys Phe Ser Tyr Glu Ile Arg Phe Asp Gly Val Asn Phe Pro Ala Asn
        115                 120                 125

Ser Pro Val Met Gln Lys Lys Thr Val Lys Trp Glu Pro Cys Thr Xaa
    130                 135                 140

Glu Met Tyr Val Arg Asp Gly Val Leu Lys Gly Gly Leu Asn Met Ala
145                 150                 155                 160

Leu Leu Leu Glu Gly Gly Gly His Phe Arg Cys Asp Leu Lys Thr Thr
                165                 170                 175

Tyr Lys Ala Lys Lys Val Val Gln Met Pro Asp Tyr His Phe Val Asn
            180                 185                 190

His Arg Leu Glu Ile Thr Trp His Asp Glu Asp Tyr Asn Asn Val Lys
        195                 200                 205

Leu Ser Glu His Ala Glu Ala His Ser Gly Leu Pro Arg Gln Ala Lys
    210                 215                 220
```

CHROMOPHORES/FLUOROPHORES AND METHODS FOR USING THE SAME

CROSS-REFERENCE TO RELATED APPLICATIONS

This application is a continuation in part of International Application Serial No. PCT/US02/36499 filed on Nov. 12, 2002 and designating the United States; which application (pursuant to 35 U.S.C. § 119 (e)) claims priority to the filing date of U.S. Provisional Patent Application Ser. No. 60/332,980 filed Nov. 13, 2001; the disclosure of which is herein incorporated by reference.

INTRODUCTION

1. Field of the Invention

The field of this invention is chromoproteins and fluorescent proteins.

2. Background of the Invention

Labeling is a tool for marking a protein, cell, or organism of interest and plays a prominent role in many biochemistry, molecular biology and medical diagnostic applications. A variety of different labels have been developed, including radiolabels, chromolabels, fluorescent labels, chemiluminescent labels, etc. However, there is continued interest in the development of new labels. Of particular interest is the development of new protein labels, including chromo- and/or fluorescent protein labels.

3. Relevant Literature

U.S. Patents of interest include: U.S. Pat. Nos. 6,066,476; 6,020,192; 5,985,577; 5,976,796; 5,968,750; 5,968,738; 5,958,713; 5,919,445; 5,874,304; and 5,491,084. International Patent Publications of interest include: WO 00/46233; WO 99/49019; and DE 197 18 640 A. Also of interest are: Anderluh et al., Biochemical and Biophysical Research Communications (1996) 220:437-442; Dove et al., Biological Bulletin (1995) 189:288-297; Fradkov et al., FEBS Lett. (2000) 479(3):127-30; Gurskaya et al., FEBS Lett., (2001) 507(1):16-20; Gurskaya et al., BMC Biochem. (2001) 2:6; Lukyanov, K., et al (2000) J Biol Chemistry 275(34):25879-25882; Macek et al., Eur. J. Biochem. (1995) 234:329-335; Martynov et al., J. Biol. Chem. (2001) 276:21012-6; Matz, M. V., et al., (1999) Nature Biotechnol.,17:969-973; Terskikh et al., Science (2000) 290:1585-8;Tsien, Annual Rev. of Biochemistry (1998) 67:509-544; Tsien, Nat. Biotech. (1999) 17:956-957; Ward et al., J. Biol. Chem. (1979) 254:781-788; Wiedermann et al., Jarhrestagung der Deutschen Gesellschact fur Tropenokologie-gto. Ulm. 17-19.02.1999. Poster P4.20; Yarbrough et al., Proc Natl Acad Sci USA (2001) 98:462-7.

SUMMARY OF THE INVENTION

Nucleic acid compositions encoding novel chromo/fluoroproteins and mutants thereof, as well as the proteins encoded the same, are provided. The proteins of interest are proteins that are colored and/or fluorescent, where this feature arises from the interaction of two or more residues of the protein. The subject proteins are further characterized in that they are either obtained from non-bioluminescent Cnidarian, e.g., Anthozoan, species or are obtained from Anthozoan non-Pennatulacean (sea pen) species. Specific proteins of interest include the following specific proteins: (1) Green fluorescent protein from Heteractis crispa (hcriGFP); (2) Green fluorescent protein from Dendronephthya sp. (dendGFP); (3) Red fluorescent protein from Zoanthus sp. (zoanRFP); (4) Green fluorescent protein from Scolymia cubensis (scubGFP1); (5) Green fluorescent protein from Scolymia cubensis (scubGFP2); (6) Red fluorescent protein from Ricordea florida (rfloRFP); (7) Green fluorescent protein from Ricordea florida (rfloGFP); (8) Red fluorescent protein from Montastraea cavernosa (mcavRFP); (9) Green fluorescent protein from Montastraea cavernosa (mcavGFP); (10) Green fluorescent protein from Condylactis gigantea (cgigGFP); (11) Green fluorescent protein from Agaricia fragilis (afraGFP); (12) Green fluorescent protein from Ricordea florida (rfloGFP2); (13) Green fluorescent protein from Montastraea cavernosa (mcavGFP2); and (14) Green fluorescent protein homolog from Montastraea annularis (mannFP). Also of interest are proteins that are substantially similar to, or mutants of, the above specific proteins. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

BRIEF DESCRIPTION OF THE FIGURES

FIGS. 4A to 4D. Summary of spectral features and chromophore structures in the family of GFP-like proteins. Note that this paper uses different names for GFP-like proteins than proposed in original publications (the original names, where available, are given in brackets in the first column; see text for nomenclature details).

FIG. 5. Summary of the major clades of GFP-like proteins from sub-class Zoantharia.

FIGS. 7A to 7C. Alignment of the currently cloned and spectroscopically characterized GFP-like proteins. Numeration above the alignment is according to GFP from *Aequorea victoria*.

FIG. 8 provides the nucleotide and amino acid sequence of wild type *Heteractis crispa* hcriGFP. (SEQ ID NO:01 & 02)

FIG. 9 provides the nucleotide and amino acid sequence of wild type *Dendronephthya* sp. dendGFP. (SEQ ID NO:03 & 04)

FIG. 10 provides the nucleotide and amino acid sequence of wild type *Zoanthus* sp. zoanRFP. (SEQ ID NO:05 & 06)

FIG. 11 provides the nucleotide and amino acid sequence of wild type *Scolymia cubensis* scubGFP1. (SEQ ID NO:07 & 08)

FIG. 12 provides the nucleotide and amino acid sequence of wild type *Scolymia cubensis* scubGFP2. (SEQ ID NO:09 & 10)

FIG. 13 provides the nucleotide and amino acid sequence of wild type *Ricordea florida* rfloRFP. (SEQ ID NO:11 & 12)

FIG. 14 provides the nucleotide and amino acid sequence of wild type *Ricordea florida* rfloGFP. (SEQ ID NO:13 & 14)

FIG. 15 provides the nucleotide and amino acid sequence of wild type *Montastraea cavernosa* mcavRFP. (SEQ ID NO:15 & 16)

FIG. 16 provides the nucleotide and amino acid sequence of wild type *Montastraea cavernosa* mcavGFP. (SEQ ID NO:17 & 18)

FIG. 17 provides the nucleotide and amino acid sequence of wild type *Condylactis gigantea* cgigGFP. (SEQ ID NO:19 & 20).

FIG. 18 provides the nucleotide and amino acid sequence of wild type *Agaricia fragilis* afraGFP. (SEQ ID NO: 21& 22).

FIG. 19 provides the nucleotide and amino acid sequence of wild type *Ricordea florida* rfloGFP2. (SEQ ID NO: 23& 24).

FIG. 20 provides the nucleotide and amino acid sequence of wild type *Montastraea cavernosa* mcavGFP2. (SEQ ID NO: 25& 26).

FIG. 21 provides the nucleotide and amino acid sequence of wild type *Montastraea annularis* mannFP. (SEQ ID NO: 27& 28).

FEATURES OF THE INVENTION

Figure 1:
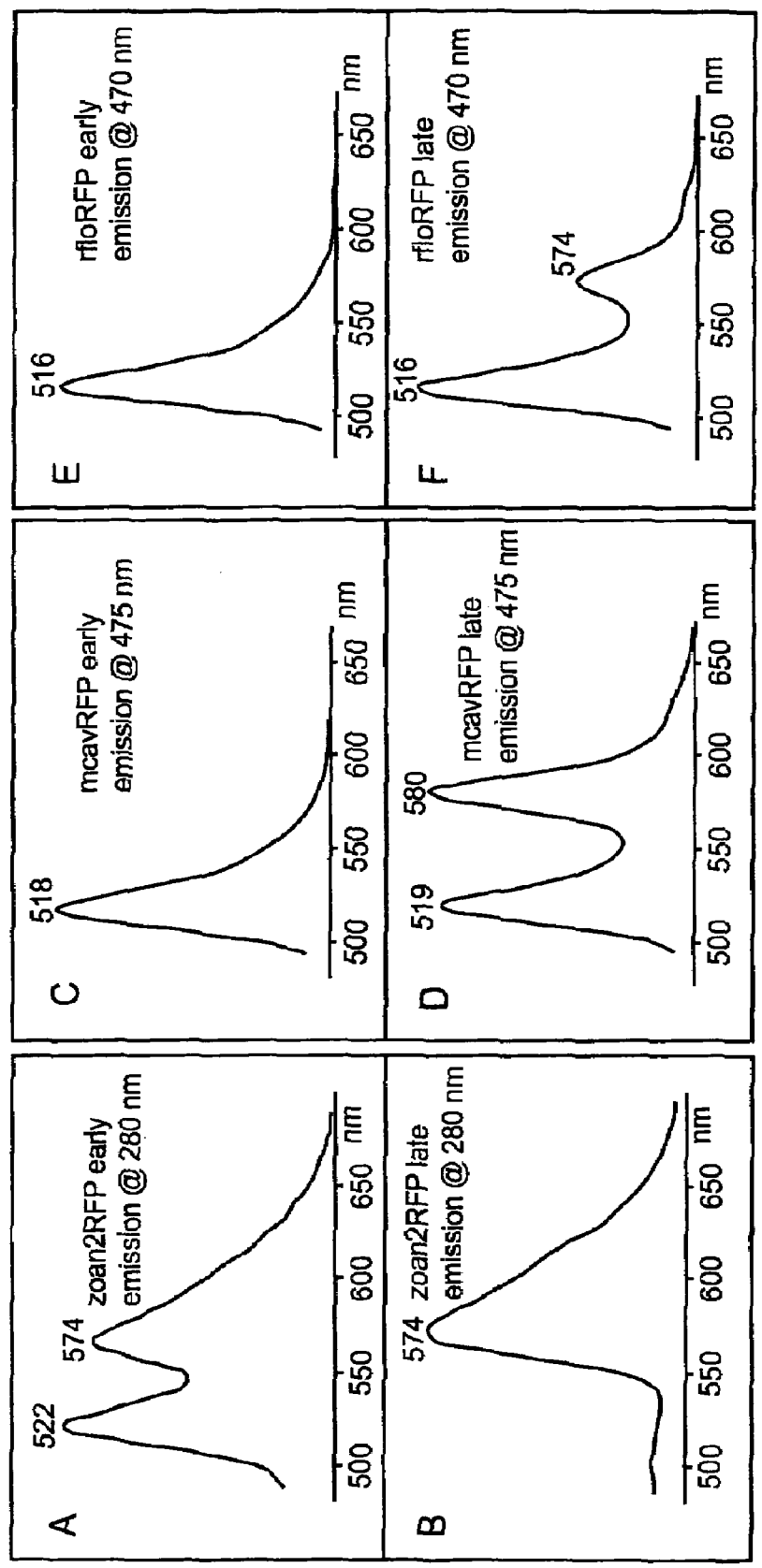
FIG. 1. Changes of emission spectra during maturation of the new red-emitters: zoan2RFP (A, B), mcavRFP (C, D) and rfloRFP (E, F). The excitation wavelength is given within each graph. Horizontal axis is wavelength in nanometers, vertical axis is fluorescence intensity. Maturation stages: A, C, E—early; B, D, F—late (see Methods for details). All the three proteins exhibit "timer" phenotype (green emission at first and red emission arising later). Note that zoan2RFP matures significantly faster than mcavRFP and rfloRFP: even at the "early" stage the red emission peak is very pronounced, and by the "late" stage the protein converts into red completely. In contrast, mcavRFP and rfloRFP fail to undergo such a complete maturation.

The subject invention provides a nucleic acid present in other than its natural environment, wherein the nucleic acid encodes a chromo- or fluorescent protein and is from a non-bioluminescent *Cnidarian* species. In certain embodiments, the non-bioluminescent *Cnidarian* species is an *Anthozoan* species. In certain embodiments, the nucleic acid is isolated. In certain embodiments, the nucleic acid is present in other than its natural environment, where the nucleic acid encodes an *Anthozoan* chromo- or fluorescent protein and is from a non-*Pennatulacean Anthozoan* species. In certain embodiments, the nucleic acid has a sequence of residues that is substantially the same as or identical to a nucleotide sequence of at least 10 residues in length of SEQ ID NOS:01, 03, 05, 07, 09, 11, 13, 15, 17; 19; 21; 23; 25; and 27. In certain embodiments, the nucleic acid has a sequence similarity of at least about 60% with a sequence of at least 10 residues in length selected from the group of sequences consisting of SEQ ID NOS:01, 03, 05, 07, 09, 11, 13, 15, 17; 19; 21; 23; 25; and 27. In certain embodiments, the nucleic acid encodes a chromo and/or fluorescent protein that is either: (a) from a non-bioluminescent *Cnidarian* species; or (b) from a non-*Pennatulacean Anthozoan* species. In certain embodiments, the nucleic acid encodes a protein that has an amino acid sequence selected from the group consisting of: SEQ ID NOS: 02; 04; 06; 08; 10; 12; 14; 16; 18; 20; 22; 24; 26; and 28. In certain embodiments, the nucleic acid encodes a mutant protein of a chromo and/or fluorescent protein that is either: (a) from a non-bioluminescent *Cnidarian* species; or (b) from a non-*Pennatulacean Anthozoan* species; where in certain embodiments the mutant protein comprises at least one point mutation as compared to its wild type protein; and in other embodiments the mutant protein comprises at least one deletion mutation as compared to its wild type protein.

Also provided are fragments of the provided nucleic acids. Also provided are isolated nucleic acids or mimetics thereof that hybridize under stringent conditions to the provided nucleic acids. Also provided are constructs comprising a vector and a nucleic acid or the present invention. Also provided are expression cassettes that include: (a) a transcriptional initiation region functional in an expression host; (b) a nucleic acid of the present invention; and (c) a transcriptional termination region functional in said expression host. Also provided are cells, or the progeny thereof, comprising an expression cassette of the present invention as part of an extrachromosomal element or integrated into the genome of a host cell as a result of introduction of said expression cassette into said host cell.

Also provided are methods of producing a chromo and/or fluorescent protein that include: growing a cell of the present invention, whereby said protein is expressed; and isolating said protein substantially free of other proteins.

Also provided are proteins or fragments thereof encoded by a nucleic acid of the present invention.

Also provided are antibodies binding specifically to a protein of the present invention.

Also provided are transgenic cells or the progeny thereof that include a transgene selected that includes a nucleic acid of the present invention.

Also provided are transgenic organisms that include a transgene that includes a nucleic acid of the present invention.

Also provided are applications that employ a chromo- or fluorescent protein of the present invention.

Also provided are applications that employ a nucleic acid encoding a chromo- or fluorescent protein of the present invention.

Also provided are kits that include a nucleic acid according the subject invention and instructions for using said nucleic acid.

DEFINITIONS

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985);

"Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243 (1969), 3552-59 is used.

The term "immunologically active" defines the capability of the natural, recombinant or synthetic chromo/fluorescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a polypeptide, an antibody, or a host cell that is in an environment different from that in which the polynucleotide, the polypeptide, the antibody, or the host cell naturally occurs.

Bioluminescence (BL) is defined as emission of light by living organisms that is well visible in the dark and affects visual behavior of animals (See e.g., Harvey, E. N. (1952). *Bioluminescence*. New York: Academic Press; Hastings, J. W. (1995). Bioluminescence. In: *Cell Physiology* (ed. by N. Speralakis). pp. 651-681. New York: Academic Press.; Wilson, T. and Hastings, J. W. (1998). Bioluminescence. *Annu Rev Cell Dev Biol* 14, 197-230.). Bioluminescence does not include so-called ultra-weak light emission, which can be detected in virtually all living structures using sensitive luminometric equipment (Murphy, M. E. and Sies, H.(1990). Visible-range low-level chemiluminescence in biological systems. *Meth.Enzymol.*186, 595-610; Radotic, K, Radenovic, C, Jeremic, M. (1998.) Spontaneous ultra-weak bioluminescence in plants: origin, mechanisms and properties. *Gen Physiol Biophys* 17, 289-308), and from weak light emission which most probably does not play any ecological role, such as the glowing of bamboo growth cone (Totsune, H., Nakano, M., Inaba, H.(1993). Chemiluminescence from bamboo shoot cut. *Biochem. Biophys.Res Comm.* 194, 1025-1029) or emission of light during fertilization of animal eggs (Klebanoff, S. J., Froeder, C. A., Eddy, E. M., Shapiro, B. M. (1979). Metabolic similarities between fertilization and phagocytosis. Conservation of peroxidatic mechanism. *J. Exp. Med.* 149, 938-953; Schomer, B. and Epel, D. (1998). Redox changes during fertilization and maturation of marine invertebrate eggs. *Dev Biol* 203, 1-11).

DESCRIPTION OF THE SPECIFIC EMBODIMENTS

Nucleic acid compositions encoding novel chromo/fluoroproteins and mutants thereof, as well as the proteins encoded the same, are provided. The proteins of interest are proteins that are colored and/or fluorescent, where this feature arises from the interaction of two or more residues of the protein. The subject proteins are further characterized in that they are either obtained from non-bioluminescent *Cnidarian*, e.g., *Anthozoan*, species or are obtained from non-*Pennatulacean* (sea pen) *Anthozoan* species. Specific proteins of interest include the following specific proteins: (1) Green fluorescent protein from *Heteractis crispa* (hcriGFP); (2) Green fluorescent protein from *Dendronephthya* sp. (dendGFP); (3) Red fluorescent protein from *Zoanthus* sp. (zoanRFP); (4) Green fluorescent protein from *Scolymia cubensis* (scubGFP1); (5) Green fluorescent protein from *Scolymia cubensis* (scubGFP2); (6) Red fluorescent protein from *Ricordea florida* (rfloRFP); (7) Green fluorescent protein from *Ricordea florida* (rfloGFP); (8) Red fluorescent protein from *Montastraea cavernosa* (mcavRFP); (9) Green fluorescent protein from *Montastraea cavernosa* (mcavGFP); (10) Green fluorescent protein from *Condylactis gigantea* (cgigGFP); (11) Green fluorescent protein from *Agaricia fragilis* (afraGFP); (12) Green fluorescent protein from *Ricordea florida* (rfloGFP2); (13) Green fluorescent protein from *Montastraea cavernosa* (mcavGFP2); and (14) Green fluorescent protein homolog from *Montastraea annularis* (mannFP). Also of interest are proteins that are substantially similar to, or mutants of, the above specific proteins. Also provided are fragments of the nucleic acids and the peptides encoded thereby, as well as antibodies to the subject proteins, and transgenic cells and organisms that include the subject nucleic acid/protein compositions. The subject protein and nucleic acid compositions find use in a variety of different applications. Finally, kits for use in such applications, e.g., that include the subject nucleic acid compositions, are provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, methodologies and other invention components that are described in the publications which might be used in connection with the presently described invention.

In further describing the subject invention, the subject nucleic acid compositions will be described first, followed by a discussion of the subject protein compositions, antibody compositions and transgenic cells/organisms. Next a review of representative methods in which the subject proteins find use is provided.

Nucleic Acid Compositions

As summarized above, the subject invention provides nucleic acid compositions encoding chromo- and fluoroproteins and mutants thereof, as well as fragments and homologues of these proteins. By chromo and/or fluorescent protein is meant a protein that is colored, i.e., is pigmented, where the protein may or may not be fluorescent, e.g., it may exhibit low, medium or high fluorescence upon irradiation with light of an excitation wavelength. In any event, the subject proteins of interest are those in which the colored characteristic, i.e., the chromo and/or fluorescent characteristic, is one that arises from the interaction of two or more residues of the protein, and not from a single residue, more specifically a single side chain of a single residue, of the protein. As such, fluorescent proteins of the subject invention do not include proteins that exhibit fluorescence only from residues that act by themselves as intrinsic fluors, i.e., tryptophan, tyrosine and phenylalanine. As such, the fluorescent proteins of the subject invention are fluorescent proteins whose fluorescence arises from some structure in the protein that is other than the above specified single residues, e.g., it arises from an interaction of two or more residues.

By nucleic acid composition is meant a composition comprising a sequence of DNA having an open reading frame that encodes a chromo/fluoro polypeptide of the subject invention, i.e., a chromo/fluoroprotein gene, and is capable, under appropriate conditions, of being expressed as a chromo/fluoro protein according to the subject invention.

Also encompassed in this term are nucleic acids that are homologous, substantially similar or identical to the nucleic acids of the present invention. Thus, the subject invention provides genes and coding sequences thereof encoding the proteins of the subject invention, as well as homologs thereof. The subject nucleic acids are present in other than their natural environment, e.g., they are isolated, present in enriched amounts, etc., from their naturally occurring environment, e.g., the organism from which they are obtained.

The nucleic acids are further characterized in that they encode proteins that are either from: (1) non-bioluminescent species, often non-bioluminescent *Cnidarian* species, e.g., non-bioluminescent *Anthozoan* species; or (2) from *Anthozoan* species that are not *Pennatulacean* species, i.e., that are not sea pens. As such, the nucleic acids may encode proteins from bioluminescent *Anthozoan* species, so long as these species are not *Pennatulacean* species, e.g., that are not *Renillan* or *Ptilosarcan* species. Specific nucleic acids of interest are those that encode the following specific proteins: (1) Green fluorescent protein from *Heteractis crispa* (hcriGFP) (Genbank Accession No. AF420592); (2) Green fluorescent protein from *Dendronephthya* sp. (dendGFP) (Genbank Accession No. AF420591); (3) Red fluorescent protein from *Zoanthus* sp. (zoanRFP) (Genbank Accession No. AY059642); (4) Green fluorescent protein from *Scolymia cubensis* (scubGFP1) (Genbank Accession No. AY037767); (5) Green fluorescent protein from *Scolymia cubensis* (scubGFP2) (Genbank Accession No. AY037771); (6) Red fluorescent protein from *Ricordea florida* (rfloRFP) (Genbank Accession No. AY037773); (7) Green fluorescent protein from *Ricordea florida* (rfloGFP) (Genbank Accession No. AY037772); (8) Red fluorescent protein from *Montastraea cavernosa* (mcavRFP) (Genbank Accession No. AY037770); (9) Green fluorescent protein from *Montastraea cavernosa* (mcavGFP) (Genbank Accession No. AY037769); (10) Green fluorescent protein from *Condylactis gigantea* (cgigGFP) (Genbank Accession No. AY03776); (11) Green fluorescent protein from *Agaricia fragilis* (afraGFP); (12) Green fluorescent protein from *Ricordea florida* (rfloGFP2); (13) Green fluorescent protein from *Montastraea cavernosa* (mcavGFP2); and (14) Green fluorescent protein homolog from *Montastraea annularis* (mannFP). Also of interest are derived from, or are mutants, homologues of, the above specific nucleic acids.

In addition to the above described specific nucleic acid compositions, also of interest are homologues of the above sequences. With respect to homologues of the subject nucleic acids, the source of homologous genes may be any species of plant or animal or the sequence may be wholly or partially synthetic. In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). The sequences provided herein are essential for recognizing related and homologous nucleic acids in database searches. Of particular interest in certain embodiments are nucleic acids of substantially the same length as the nucleic acid identified as SEQ ID NOS: 01, 03, 05, 07, 09, 11, 13, 15, 17, 19, 21, 23, 25 or 27, where by substantially the same length is meant that any difference in length does not exceed about 20 number %, usually does not exceed about 10 number % and more usually does not exceed about 5 number %; and have sequence identity to any of these sequences of at least about 90%, usually at least about 95% and more usually at least about 99% over the entire length of the nucleic acid. In many embodiments, the nucleic acids have a sequence that is substantially similar (i.e. the same as) or identical to the sequences of SEQ ID NOS: 01, 03, 05, 07, 09, 11, 13, 15, 17, 21, 23, 25, 27. By substantially similar is meant that sequence identity will generally be at least about 60%, usually at least about 75% and often at least about 80, 85, 90, or even 95%.

Also provided are nucleic acids that encode the proteins encoded by the above described nucleic acids, but differ in sequence from the above described nucleic acids due to the degeneracy of the genetic code.

Also provided are nucleic acids that hybridize to the above described nucleic acid under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Nucleic acids encoding mutants of the proteins of the invention are also provided. Mutant nucleic acids can be generated by random mutagenesis or targeted mutagenesis, using well-known techniques which are routine in the art. In some embodiments, chromo- or fluorescent proteins encoded by nucleic acids encoding homologues or mutants have the same fluorescent properties as the wild-type fluorescent protein. In other embodiments, homologue or mutant nucleic acids encode chromo- or fluorescent proteins with altered spectral properties, as described in more detail herein.

One category of mutant that is of particular interest is the non-aggregating mutant. In many embodiments, the non-aggregating mutant differs from the wild type sequence by a mutation in the N-terminus that modulates the charges appearing on side groups of the N-terminus residues, e.g., to reverse or neutralize the charge, in a manner sufficient to produce a non-aggregating mutant of the naturally occurring protein or mutant, where a particular protein is considered to be non-aggregating if it is determined be non-aggregating using the assay reported in U.S. patent application Ser. No. 60/270,983, the disclosure of which is herein incorporated by reference.

Another category of mutant of particular interest is the modulated oligomerization mutant. A mutant is considered to be a modulated oligomerization mutant if its oligomerization properties are different as compared to the wild type protein. For example, if a particular mutant oligomerizes to a greater or lesser extent than the wild type, it is considered to be an oligomerization mutant. Of particular interest are oligomerization mutants that do not oligomerize, i.e., are monomers under physiological (e.g., intracellular) conditions, or oligomerize to a lesser extent that the wild type, e.g., are dimers or trimers under intracellular conditions.

Nucleic acids of the subject invention may be cDNA or genomic DNA or a fragment thereof. In certain embodiments, the nucleic acids of the subject invention include one or more of the open reading frames encoding specific fluorescent proteins and polypeptides, and introns, as well as adjacent 5' and 3' non-coding nucleotide sequences involved in the regulation of expression, up to about 20 kb beyond the coding region, but possibly further in either direction. The subject nucleic acids may be introduced into an appropriate vector for extrachromosomal maintenance or for integration into a host genome, as described in greater detail below.

The term "cDNA" as used herein is intended to include all nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest comprises the nucleic acid present between the initiation codon and the stop codon, as defined in the listed sequences, including all of the introns that are normally present in a native chromosome. It may further include 5' and 3' un-translated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject proteins. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least about 15 nt, usually at least about 18 nt or about 25 nt, and may be at least about 50 nt. In some embodiments, the subject nucleic acid molecules may be about 100 nt, about 200 nt, about 300 nt, about 400 nt, about 500 nt, about 600 nt, about 700 nt, or about 720 nt in length. The subject nucleic acids may encode fragments of the subject proteins or the full-length proteins, e.g., the subject nucleic acids may encode polypeptides of about 25 aa, about 50 aa, about 75 aa, about 100 aa, about 125 aa, about 150 aa, about 200 aa, about 210 aa, about 220 aa, about 230 aa, or about 240 aa, up to the entire protein.

The subject nucleic acids are isolated and obtained in substantial purity, generally as other than an intact chromosome. Usually, the DNA will be obtained substantially free of other nucleic acid sequences that do not include a nucleic acid of the subject invention or fragment thereof, generally being at least about 50%, usually at least about 90% pure and are typically "recombinant", i.e. flanked by one or more nucleotides with which it is not normally associated on a naturally occurring chromosome.

The subject polynucleotides (e.g., a polynucleotide having a sequence of SEQ ID NOS: 01, 03, 05, 07, 09, 11, 13, 15, 17, 19, 21, 23, 25, 27 etc.), the corresponding cDNA, the full-length gene and constructs of the subject polynucleotides are provided. These molecules can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual*, 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Also provided are nucleic acids that encode fusion proteins of the subject proteins, or fragments thereof, which are fused to a second protein, e.g., a degradation sequence, a signal peptide, etc. Fusion proteins may comprise a subject polypeptide, or fragment thereof, and a non-*Anthozoan* polypeptide ("the fusion partner") fused in-frame at the N-terminus and/or C-terminus of the subject polypeptide. Fusion partners include, but are not limited to, polypeptides that can bind antibody specific to the fusion partner (e.g., epitope tags); antibodies or binding fragments thereof; polypeptides that provide a catalytic function or induce a cellular response; ligands or receptors or mimetics thereof; and the like. In such fusion proteins, the fusion partner is generally not naturally associated with the subject *Anthozoan* portion of the fusion protein, and is typically not an *Anthozoan* protein or derivative/fragment thereof, i.e., it is not found in *Anthozoan* species.

Also provided are constructs comprising the subject nucleic acids inserted into a vector, where such constructs may be used for a number of different applications, including propagation, protein production, etc. Viral and non-viral vectors may be prepared and used; including plasmids. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a subject polynucleotide, e.g., as set forth in SEQ ID NOS:01; 03; 05; 07; 09; 11; 13; 15; 17; 19; 21; 23; 25 or 27, is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, *Xenopus* Oocytes, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (USA) (1983) 80:21-25; and Siebenlist et al., *Cell* (1980) 20:269.

Yeast. Expression systems in yeast include those described in Hinnen et al., *Proc. Natl. Acad. Sci.* (USA) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154: 737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Natl. Acad. Sci.* (USA) (1984) 81:1470-1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci.* (USA) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci.* (USA) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject proteins without manipulation of the encoding nucleic acid itself, but instead through integration of a regulatory sequence into the genome of cell that already includes a gene encoding the desired protein, as described in the above incorporated patent documents.

Also provided are homologs of the subject nucleic acids. Homologs are identified by any of a number of methods. A fragment of the provided cDNA may be used as a hybridization probe against a cDNA library from the target organism of interest, where low stringency conditions are used.

The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/1.5 mM sodium citrate). Nucleic acids having a region of substantial identity to the provided sequences, e.g., allelic variants, genetically altered versions of the gene, etc., bind to the provided sequences under stringent hybridization conditions. By using probes, particularly labeled probes of DNA sequences, one can isolate homologous or related genes.

Also of interest are promoter elements of the subject genomic sequences, where the sequence of the 5' flanking region may be utilized for promoter elements, including enhancer binding sites, e.g., that provide for regulation of expression in cells/tissues where the subject proteins gene are expressed.

Also provided are small DNA fragments of the subject nucleic acids, which fragments are useful as primers for PCR, hybridization screening probes, etc. Larger DNA fragments, i.e., greater than 100 nt are useful for production of the encoded polypeptide, as described in the previous section. For use in geometric amplification reactions, such as geometric PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of *Anthozoan* protein gene expression in the sample.

The subject nucleic acids, including flanking promoter regions and coding regions, may be mutated in various ways known in the art to generate targeted changes in promoter strength, sequence of the encoded protein, properties of the encoded protein, including fluorescent properties of the encoded protein, etc. The DNA sequence or protein product of such a mutation will usually be substantially similar to the sequences provided herein, e.g. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more aa residues. Techniques for in vitro mutagenesis of cloned genes are known. Examples of protocols for site specific mutagenesis may be found in Gustin et al. (1993), *Biotechniques* 14:22; Barany (1985), *Gene* 37:111-23; Colicelli et al. (1985), *Mol. Gen. Genet* 199:537-9; and Prentki et al. (1984), *Gene* 29:303-13. Methods for site specific mutagenesis can be found in Sambrook et al., *Molecular Cloning: A Laboratory Manual*, CSH Press 1989, pp. 15.3-15.108; Weiner et al. (1993), *Gene* 126:35-41; Sayers et al. (1992), *Biotechniques* 13:592-6; Jones and Winistorfer (1992), *Biotechniques* 12:528-30; Barton et al. (1990), *Nucleic Acids Res* 18:7349-55; Marotti and Tomich (1989), *Gene Anal. Tech.* 6:67-70; and Zhu (1989), *Anal Biochem* 177:120-4. Such mutated nucleic acid derivatives may be used to study structure-function relationships of a particular chromo/fluorescent protein, or to alter properties of the protein that affect its function or regulation.

Of particular interest in many embodiments is the following specific mutation protocol, which protocol finds use in mutating chromoproteins (e.g., colored proteins that have little if any fluorescence) into fluorescent mutants. In this protocol, the sequence of the candidate protein is aligned with the amino acid sequence of *Aequorea Victoria* wild type GFP, according to the protocol reported in Matz et al., "Fluorescent proteins from non-bioluminescent *Anthozoa* species," Nature Biotechnology (October 1999) 17: 969-973. Residue 148 of the aligned chromoprotein is identified and then changed to Ser, e.g., by site directed mutagenesis, which results in the production of a fluorescent mutant of the wild type chromoprotein. See e.g., NFP-7 described below, which wild type protein is a chromoprotein that is mutated into a fluorescent protein by substitution of Ser for the native Ala residue at position 148.

Also of interest are humanized versions of the subject nucleic acids. As used herein, the term "humanized" refers to changes made to the a nucleic acid sequence to optimize the codons for expression of the protein in human cells (Yang et al., *Nucleic Acids Research* 24 (1996), 4592-4593). See also U.S. Pat. No. 5,795,737 which describes humanization of proteins, the disclosure of which is herein incorporated by reference.

Protein/Polypeptide Compositions

Also provided by the subject invention are chromo- and/or fluorescent proteins and mutants thereof, as well as polypeptide compositions related thereto. As the subject proteins are chromoproteins, they are colored proteins, which may be fluorescent, low or non-fluorescent. As used herein, the terms chromoprotein and fluorescent protein do not include luciferases, such as *Renilla* luciferase, and refer to any protein that is pigmented or colored and/or fluoresces when irradiated with light, e.g., white light or light of a specific wavelength (or narrow band of wavelengths such as an excitation wavelength). The term polypeptide composition as used herein refers to both the full-length protein, as well as portions or fragments thereof. Also included in this term are variations of the naturally occurring protein, where such variations are homologous or substantially similar to the naturally occurring protein, and mutants of the naturally occurring proteins, as described in greater detail below. The subject polypeptides are present in other than their natural environment.

In many embodiments, the subject proteins have an absorbance maximum ranging from about 300 to 700, usually from about 350 to 650 and more usually from about 400 to 600 nm. Where the subject proteins are fluorescent proteins, by which is meant that they can be excited at one wavelength of light following which they will emit light at another wavelength, the excitation spectra of the subject proteins typically ranges from about 300 to 700, usually from about 350 to 650 and more usually from about 400 to 600 nm while the emission spectra of the subject proteins typically ranges from about 400 to 800, usually from about 425 to 775 and more usually from about 450 to 750 nm. The subject proteins generally have a maximum extinction coefficient that ranges from about 10,000 to 50,000 and usually from about 15,000 to 45,000. The subject proteins typically range in length from about 150 to 300 and usually from about 200 to 300 amino acid residues, and generally have a molecular weight ranging from about 15 to 35 kDa, usually from about 17.5 to 32.5 kDa.

In certain embodiments, the subject proteins are bright, where by bright is meant that the chromoproteins and their fluorescent mutants can be detected by common methods (e.g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient. Brightness of a chromoproteins may be expressed by its maximal extinction coefficient.

In certain embodiments, the subject proteins fold rapidly following expression in the host cell. By rapidly folding is meant that the proteins achieve their tertiary structure that gives rise to their chromo- or fluorescent quality in a short period of time. In these embodiments, the proteins fold in a period of time that generally does not exceed about 3 days, usually does not exceed about 2 days and more usually does not exceed about 1 day.

Specific proteins of interest include the following specific proteins: (1) Green fluorescent protein from *Heteractis crispa* (hcriGFP); (2) Green fluorescent protein from *Dendronephthya* sp. (dendGFP); (3) Red fluorescent protein from *Zoanthus* sp. (zoanRFP); (4) Green fluorescent protein from *Scolymia cubensis* (scubGFP1); (5) Green fluorescent protein from *Scolymia cubensis* (scubGFP2); (6) Red fluorescent protein from *Ricordea florida* (rfloRFP); (7) Green fluorescent protein from *Ricordea florida* (rfloGFP); (8) Red fluorescent protein from *Montastraea cavernosa* (mcavRFP); (9) Green fluorescent protein from *Montastraea cavernosa* (mcavGFP); (10) Green fluorescent protein from *Condylactis gigantea* (cgigGFP); (11) Green fluorescent protein from *Agaricia fragilis* (afraGFP); (12) Green fluorescent protein from *Ricordea florida* (rfloGFP2); (13) Green fluorescent protein from *Montastraea cavernosa* (mcavGFP2); and (14) Green fluorescent protein homolog from *Montastraea annularis* (mannFP).

Homologs or proteins (or fragments thereof) that vary in sequence from the above provided specific amino acid sequences of the subject invention, i.e., SEQ ID NOS: 02; 04; 06; 08; 10; 12; 14; 16; 18; 20; 22; 24; 26 or 28, are also provided. By homolog is meant a protein having at least about 10%, usually at least about 20% and more usually at least about 30%, and in many embodiments at least about 35%, usually at least about 40% and more usually at least about 60% amino acid sequence identity to the protein of the subject invention, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151-153. (Parameters used are ktuple 1, gap penalty 3, window, 5 and diagonals saved 5). In many embodiments, homologues of interest have much higher sequence identify, e.g., 65%, 70%, 75%, 80%, 85%, 90% or higher.

Also provided are proteins that are substantially identical to the wild type protein, where by substantially identical is meant that the protein has an amino acid sequence identity to the sequence of wild type protein of at least about 60%, usually at least about 65% and more usually at least about 70%, where in some instances the identity may be much higher, e.g., 75%, 80%, 85%, 90%, 95% or higher.

In many embodiments, the subject homologues have structural features found in the above provided specific sequences, where such structural features include the β-can fold.

Proteins which are mutants of the above-described naturally occurring proteins are also provided. Mutants may retain biological properties of the wild-type (e.g., naturally occurring) proteins, or may have biological properties which differ from the wild-type proteins. The term "biological property" of the subject proteins includes, but is not limited to, spectral properties, such as absorbance maximum, emission maximum, maximum extinction coefficient, brightness (e.g., as compared to the wild-type protein or another reference protein such as green fluorescent protein from *A. Victoria*), and the like; in vivo and/or in vitro stability (e.g., half-life); etc. Mutants include single amino acid changes, deletions of one or more amino acids, N-terminal truncations, C-terminal truncations, insertions, etc.

Mutants can be generated using standard techniques of molecular biology, e.g., random mutagenesis, and targeted mutagenesis. Several mutants are described herein. Given the guidance provided in the Examples, and using standard techniques, those skilled in the art can readily generate a wide variety of additional mutants and test whether a biological property has been altered. For example, fluorescence intensity can be measured using a spectrophotometer at various excitation wavelengths.

Those proteins of the subject invention that are naturally occurring proteins are present in a non-naturally occurring environment, e.g., are separated from their naturally occurring environment. In certain embodiments, the subject proteins are present in a composition that is enriched for the subject protein as compared to its naturally occurring environment. For example, purified protein is provided, where by purified is meant that the protein is present in a composition that is substantially free of non-chromo/fluoroprotein proteins of interest, where by substantially free is meant that less than 90%, usually less than 60% and more usually less than 50% of the composition is made up of non-chromoproteins or mutants thereof of interest. The proteins of the subject invention may also be present as an isolate, by which is meant that the protein is substantially free of other proteins and other naturally occurring biologic molecules, such as oligosaccharides, polynucleotides and fragments thereof, and the like, where the term "substantially free" in this instance means that less than 70%, usually less than 60% and more usually less than 50% of the composition containing the isolated protein is some other naturally occurring biological molecule. In certain embodiments, the proteins are present in substantially pure form, where by "substantially pure form" is meant at least 95%, usually at least 97% and more usually at least 99% pure.

In addition to the naturally occurring proteins, polypeptides that vary from the naturally occurring proteins, e.g., the mutant proteins described above, are also provided. Generally such polypeptides include an amino acid sequence encoded by an open reading frame (ORF) of the gene encoding the subject wild type protein, including the full length protein and fragments thereof, particularly biologically active fragments and/or fragments corresponding to functional domains, and the like; and including fusions of the subject polypeptides to other proteins or parts thereof. Fragments of interest will typically be at least about 10 aa in length, usually at least about 50 aa in length, and may-be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length. In some embodiments, the subject polypeptides are about 25 aa, about 50 aa, about 75 aa, about 100 aa, about 125 aa, about 150 aa, about 200 aa, about 210 aa, about 220 aa, about 230 aa, or about 240 aa in length, up to the entire protein. In some embodiments, a protein fragment retains all or substantially all of a biological property of the wild-type protein.

The subject proteins and polypeptides may be obtained from naturally occurring sources or synthetically produced. For example, wild type proteins may be derived from biological sources which express the proteins, e.g., non-bioluminescent *Cnidarian*, e.g., *Anthozoan*, species, such as the specific ones listed above. The subject proteins may also be derived from synthetic means, e.g., by expressing a recombinant gene or nucleic acid coding sequence encoding the protein of interest in a suitable host, as described above. Any convenient protein purification procedures may be employed, where suitable protein purification methodologies are described in Guide to Protein Purification, (Deuth-ser ed.) (Academic Press, 1990). For example, a lysate may prepared from the original source and purified using HPLC, exclusion chromatography, gel electrophoresis, affinity chromatography, and the like.

Antibody Compositions

Also provided are antibodies that specifically bind to the subject fluorescent proteins. Suitable antibodies are obtained by immunizing a host animal with peptides comprising all or a portion of the subject protein. Suitable host animals include mouse, rat sheep, goat, hamster, rabbit, etc. The origin of the protein immunogen will generally be a *Cnidarian* species, specifcally a non-bioluminescent *Cnidarian* species, such as an *Anthozoan* species or a non-*Petalucean Anthozoan* species. The host animal will generally be a different species than the immunogen, e.g., mice, etc.

The immunogen may comprise the complete protein, or fragments and derivatives thereof. Preferred immunogens comprise all or a part of the protein, where these residues contain the post-translation modifications found on the native target protein. Immunogens are produced in a variety of ways known in the art, e.g., expression of cloned genes using conventional recombinant methods, isolation from *Anthozoan* species of origin, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Transgenics

The subject nucleic acids can be used to generate transgenic, non-human plants or animals or site specific gene modifications in cell lines. Transgenic cells of the subject invention include on or more nucleic acids according to the subject invention present as a transgene, where included within this definition are the parent cells-transformed to include the transgene and the progeny thereof. In many embodiments, the transgenic cells are cells that do not normally harbor or contain a nucleic acid according to the subject invention. In those embodiments where the transgenic cells do naturally contain the subject nucleic acids, the nucleic acid will be present in the cell in a position other than its natural location, i.e. integrated into the genomic material of the cell at a non-natural location. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Transgenic organisms of the subject invention include cells and multicellular organisms, e.g., plants and animals, that are endogenous knockouts in which expression of the endogenous gene is at least reduced if not eliminated. Transgenic organisms of interest also include cells and multicellular organisms, e.g., plants and animals, in which the protein or variants thereof is expressed in cells or tissues where it is not normally expressed and/or at levels not normally present in such cells or tissues.

DNA constructs for homologous recombination will comprise at least a portion of the gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc. Representative examples of the use of transgenic animals include those described infra.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons)(1993) pp 275-295. In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction. With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is *Agrobacterium* mediated transformation. With *Agrobacterium* mediated transformation, co-integrative or binary vectors comprising the exogenous DNA are prepared and then introduced into an appropriate *Agrobacterium* strain, e.g. *A. tumefaciens*. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

Utility

The subject chromoproteins and fluorescent mutants thereof find use in a variety of different applications, where the applications necessarily differ depending on whether the protein is a chromoprotein or a fluorescent protein. Representative uses for each of these types of proteins will be described below, where the follow described uses are merely representative and are in no way meant to limit the use of the subject proteins to those described below.

Chromoproteins

The subject chromoproteins of the present invention find use in a variety of different applications. One application of interest is the use of the subject proteins as coloring agents which are capable of imparting color or pigment to a particular composition of matter. Of particular interest in certain embodiments are non-toxic chromoproteins. The subject chromoproteins may be incorporated into a variety of different compositions of matter, where representative compositions of matter include: food compositions, pharmaceuticals, cosmetics, living organisms, e.g., animals and plants, and the like. Where used as a coloring agent or pigment, a sufficient amount of the chromoprotein is incorporated into the composition of matter to impart the desired color or pigment thereto. The chromoprotein may be incorporated into the composition of matter using any convenient protocol, where the particular protocol employed will necessarily depend, at least in part, on the nature of the composition of matter to be colored. Protocols that may be employed include, but are not limited to: blending, diffusion, friction, spraying, injection, tattooing, and the like.

The chromoproteins may also find use as labels in analyte detection assays, e.g., assays for biological analytes of interest. For example, the chromoproteins may be incorporated into adducts with analyte specific antibodies or binding fragments thereof and subsequently employed in immunoassays for analytes of interest in a complex sample, as described in U.S. Pat. No. 4,302,536; the disclosure of which is herein incorporated by reference. Instead of antibodies or binding fragments thereof, the subject chromoproteins or chromogenic fragments thereof may be conjugated to ligands that specifically bind to an analyte of interest, or other moieties, growth factors, hormones, and the like; as is readily apparent to those of skill in the art.

In yet other embodiments, the subject chromoproteins-may-be used as selectable markers in recombinant DNA applications, e.g., the production of transgenic cells and organisms, as described above. As such, one can engineer a particular transgenic production protocol to employ expression of the subject chromoproteins as a selectable marker, either for a successful or unsuccessful protocol. Thus, appearance of the color of the subject chromoprotein in the phenotype of the transgenic organism produced by a particular process can be used to indicate that the particular organism successfully harbors the transgene of interest, often integrated in a manner that provides for expression of the transgene in the organism. When used a selectable marker, a nucleic acid encoding for the subject chromoprotein can be employed in the transgenic generation process, where this process is described in greater detail supra. Particular transgenic organisms of interest where the subject proteins may be employed as selectable markers include transgenic plants, animals, bacteria, fungi, and the like.

In yet other embodiments, the chromoproteins (and fluorescent proteins) of the subject invention find use in sunscreens, as selective filters, etc., in a manner similar to the uses of the proteins described in WO 00/46233.

Fluorescent Proteins

The subject fluorescent proteins of the present invention (as well as other components of the subject invention described above) find use in a variety of different applications, where such applications include, but are not limited to, the following. The first application of interest is the use of the subject proteins in fluorescence resonance energy transfer (FRET) applications. In these applications, the subject proteins serve as donor and/or acceptors in combination with a second fluorescent protein or dye, e.g., a fluorescent protein as described in Matz et al., Nature Biotechnology (October 1999) 17:969-973, a green fluorescent protein from *Aequoria Victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference, other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference. Specific examples of where FRET assays employing the subject fluorescent proteins may be used include, but are not limited to: the detection of protein-protein interactions, e.g., mammalian two-hybrid system, transcription factor dimerization, membrane protein multimerization, multiprotein complex formation, etc., as a biosensor for a number of different events, where a peptide or protein covalently links a FRET fluorescent combination including the subject fluorescent proteins and the linking peptide or protein is, e.g., a protease specific substrate, e.g., for caspase mediated cleavage, a linker that undergoes conformational change upon receiving a signal which increases or decreases FRET, e.g., PKA regulatory domain (cAMP-sensor), phosphorylation, e.g., where there is a phosphorylation site in the linker or the linker has binding specificity to phosphorylated/dephosphorylated domain of another protein, or the linker has $Ca^{2+}$ binding domain. Representative fluorescence resonance energy transfer or FRET applications in which the subject proteins find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

The subject fluorescent proteins also find use as biosensors in prokaryotic and eukaryotic cells, e.g. as $Ca^{2+}$ ion indicator; as pH indicator, as phorphorylation indicator, as an indicator of other ions, e.g., magnesium, sodium, potassium, chloride and halides. For example, for detection of Ca ion, proteins containing an EF-hand motif are known to translocate from the cytosol to membranes upon $Ca^{2+}$ binding. These proteins contain a myristoyl group that is buried within the molecule by hydrophobic interactions with other regions of the protein. Binding of $Ca^{2+}$ induces a conformational change exposing the myristoyl group which then is available for the insertion into the lipid bilayer (called a "$Ca^{2+}$-myristoyl switch"). Fusion of such a EF-hand containing protein to Fluorescent Proteins (FP) could make it an indicator of intracellular $Ca^{2+}$ by monitoring the translocation from the cytosol to the plasma membrane by confocal microscopy. EF-hand proteins suitable for use in this system include, but are not limited to: recoverin (1-3), calcineurin B, troponin C, visinin, neurocalcin, calmodulin, parvalbumin, and the like. For pH, a system based on hisactophilins may be employed. Hisactophilins are myristoylated histidine-rich proteins known to exist in *Dictyostelium*. Their binding to actin and acidic lipids is sharply pH-dependent within the range of cytoplasmic pH variations. In living cells membrane binding seems to override the interaction of hisactophilins with actin filaments. At pH≦6.5 they locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By fusing FPs (Fluoresent Proteins) to hisactophilin the intracellular distribution of the fusion protein can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells. Substantial pH-dependent redistribution of hisactophilin-FP from the cytosol to the plasma membrane occurs within 1-2 min and reaches a steady state level after 5-10 min. The reverse reaction takes place on a similar time scale. As such, hisactophilin-fluorescent protein fusion protein that acts in an analogous fashion can be used to monitor cytosolic pH changes in real time in live mammalian cells. Such methods have use in high throuhgput applications, e.g., in the measurement of pH changes as consequence of growth factor receptor activation (e.g. epithelial or platelet-derived growth factor) chemotactic stimulation/cell locomotion, in the detection of intracellular pH changes as second messenger, in the monitoring of intracellular pH in pH manipulating experiments, and the like. For detection of PKC activity, the reporter system exploits the fact that a molecule called MARCKS (myristoylated alanine-rich C kinase substrate) is a PKC substrate. It is anchored to the plasma membrane via myristoylation and a stretch of positively charged amino acids (ED-domain) that bind to the negatively charged plasma membrane via electrostatic interactions. Upon PKC activation the ED-domain becomes phosphorylated by PKC, thereby becoming negatively charged, and as a consequence of electrostatic repulsion MARCKS translocates from the plasma membrane to the cytoplasm (called the "myristoyl-electrostatic switch"). Fusion of the N-terminus of MARCKS ranging from the myristoylation motif to the ED-domain of MARCKS to fluorescent proteins of the present invention makes the above a detector system for PKC activity. When phosphorylated by PKC, the fusion protein translocates from the plasma membrane to the cytosol. This translocation is followed by standard fluorescence microscopy or confocal microscopy e.g. using the Cellomics technology or other High Content Screening systems (e.g. Universal Imaging Corp./Becton Dickinson). The above reporter system has application in High Content Screening, e.g., screening for PKC inhibitors, and as an indicator for PKC activity in many screening scenarios for potential reagents interfering with this signal transduction pathway. Methods of using fluorescent proteins as biosensors also include those described in U.S. Pat. Nos. 972,638; 5,824,485 and 5,650,135 (as well as the references cited therein) the disclosures of which are herein incorporated by reference.

The subject fluorescent proteins also find use in applications involving the automated screening of arrays of cells expressing fluorescent reporting groups by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth, etc.; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin) as tools for High Content Screening: co-localization of other fluorescent fusion proteins with these localization markers as indicators of movements of intracellular fluorescent fusion proteins/peptides or as marker alone; and the like. Examples of applications involving the automated screening of arrays of cells in which the subject fluorescent proteins find use include: U.S. Pat. No. 5,989,835; as well as WO/0017624; WO 00/26408; WO 00/17643; and WO 00/03246; the disclosures of which are herein incorporated by reference.

The subject fluorescent proteins also find use in high through-put screening assays. The subject fluorescent proteins are stable proteins with half-lives of more than 24 h. Also provided are destabilized versions of the subject fluorescent proteins with shorter half-lives that can be used as transcription reporters for drug discovery. For example, a protein according to the subject invention can be fused with a putative proteolytic signal sequence derived from a protein with shorter half-life, e.g., PEST sequence from the mouse ornithine decarboxylase gene, mouse cyclin B1 destruction box and ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening, e.g., AP1, NFAT, NFkB, Smad, STAT, p53, E2F, Rb, myc, CRE, ER, GR and TRE, and the like.

The subject proteins can be used as second messenger detectors, e.g., by fusing the subject proteins to specific domains: e.g., PKCgamma Ca binding domain, PKCgamma DAG binding domain, SH2 domain and SH3 domain, etc.

Secreted forms of the subject proteins can be prepared, e.g. by fusing secreted leading sequences to the subject proteins to construct secreted forms of the subject proteins, which in turn can be used in a variety of different applications.

The subject proteins also find use in fluorescence activated cell sorting applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo marker in animals (e.g., transgenic animals). For example, expression of the subject protein can be driven by tissue specific promoters, where such methods find use in research for gene therapy, e.g., testing efficiency of transgenic expression, among other applications. A representative application of fluorescent proteins in transgenic animals that illustrates this class of applications of the subject proteins is found in WO 00/02997, the disclosure of which is herein incorporated by reference.

Additional applications of the subject proteins include: as markers following injection into cells or animals and in calibration for quantitative measurements (fluorescence and protein); as markers or reporters in oxygen biosensor devices for monitoring cell viability; as markers or labels for animals, pets, toys, food, etc.; and the like.

The subject fluorescent proteins also find use in protease cleavage assays. For example, cleavage inactivated fluorescence assays can be developed using the subject proteins, where the subject proteins are engineered to include a protease specific cleavage sequence without destroying the fluorescent character of the protein. Upon cleavage of the fluorescent protein by an activated protease fluorescence would sharply decrease due to the destruction of a functional chromophor. Alternatively, cleavage activated fluorescence can be developed using the subject proteins, where the subject proteins are engineered to contain an additional spacer sequence in close proximity/or inside the chromophor. This variant would be significantly decreased in its fluorescent activity, because parts of the functional chromophor would be divided by the spacer. The spacer would be framed by two identical protease specific cleavage sites. Upon cleavage via the activated protease the spacer would be cut out and the two residual "subunits" of the fluorescent protein would be able to reassemble to generate a functional fluorescent protein. Both of the above types of application could be developed in assays for a variety of different types of proteases, e.g., caspases, etc.

The subject proteins can also be used is assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes also allowing colocalization of membrane proteins in specific phospholipid rafts can be accomplished with the subject proteins. For example, the PH domain of GRP1 has a high affinity to phosphatidyl-inositol tri-phosphate (PIP3) but not to PIP2. As such, a fusion protein between the PH domain of GRP1 and the subject proteins can be constructed to specifically label PIP3 rich areas in biological membranes.

Yet another application of the subject proteins is as a fluorescent timer, in which the switch of one fluorescent color to another (e.g. green to red) concomitant with the ageing of the fluorescent protein is used to determine the activation/deactivation of gene expression, e.g., developmental gene expression, cell cycle dependent gene expression, circadian rhythm specific gene expression, and the like The antibodies of the subject invention, described above, also find use in a number of applications, including the differentiation of the subject proteins from other fluorescent proteins.

Kits

Also provided by the subject invention are kits for use in practicing one or more of the above described applications, where the subject kits typically include elements for making the subject proteins, e.g., a construct comprising a vector that includes a coding region for the subject protein. The subject kit components are typically present in a suitable storage medium, e.g., buffered solution, typically in a suitable container. Also present in the subject kits may be antibodies to the provided protein. In certain embodiments, the kit comprises a plurality of different vectors each encoding the subject protein, where the vectors are designed for expression in different environments and/or under different conditions, e.g., constitutive expression where the vector includes a strong promoter for expression in mammalian cells, a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Introduction

In the following experimental section, we present eleven new GFP-like proteins.

II. Materials and Methods

A. Collection of Samples

Samples (100-500 mg of tissue) of *Montastraea cavernosa, Condylactis gigantea, Scolumia cubensis* and *Ricordea florida* were collected at Florida Keys Marine Sanctuary (Long Key), under National Marine Sanctuary authorization FKNMS-2000-009. The samples were collected during night dives, candidate specimens were picked on the basis of their appearance under ultraviolet flashlight. Other samples (*Dendronephthya* sp., Heteractis crispa, *Discosoma* sp.3, *Zoanthus* sp. 2) were picked from private seawater aquariums.

B. Cloning and Expression of GFP-Like Proteins

Total RNA was isolated from the tissue samples following the protocol described in Chomczynski, P. & Sacchi, N. (1987) *Anal Biochem* 162, 156-9. Total cDNA was amplified using SMART™ cDNA amplification kit (Clontech). These amplified cDNA samples were used to amplify 3'-fragments of cDNAs coding for GFP-like proteins and then obtain the missing 5'-flanks, exactly as described in Matz, M. V., Fradkov, A. F., Labas, Y. A., Savitsky, A. P., Zaraisky, A. G., Markelov, M. L. & Lukyanov, S. A. (1999) *Nat Biotechnol* 17, 969-73. After determining the complete cDNA sequence, the coding regions were amplified using the same cDNA samples as were used to clone the 3'- and 5'-flanks as templates. An upstream ("N-terminal") primer had a 5'-heel (5'-tTGAtTGAtTGAAGGAGAaatatc) carrying stop codons (bold) in all frames and bacterial ribosome-binding site (underlined), followed by the target cDNA sequence (20-22 bases) starting with initiation codon of the ORF. The downstream ("C-terminal") primer was 22-25 bases long and corresponded to the antisense sequence of cDNA around the stop codon of the ORF. The resulting fragments were cloned using PGEM-T vector cloning kit (Promega) following the manufacturer's protocol, using *Escherichia coli* JM109 strain as host. The colonies were grown on LB/agar/carbenicillin plates supplemented with 0.3 mM IPTG for 16-20 hours at 37° C., and then incubated for two days at 4° C. The fluorescent colonies were selected using fluorescent microscope and streaked widely on new plates. The same colonies were used for overnight culture inoculation followed by plasmid isolation and sequencing, to confirm the identity of the clone. The bacteria were harvested from the plates, suspended in 1 ml of PBS and disrupted by sonication. The lysate was cleared by centrifugation, and its fluorescent properties were determined using LS-50B spectrofluorometer (Perkin Elmer Instruments). For mcavRFP and rfloGFP, the "early" samples were harvested after 24 hours at 37° C., "late" samples—after 24 hours at 37 C followed by four days at 4° C.

C. Phylogenetic analysis

The alignment of GFP-like proteins (see supplemental data) was constructed after Matz, M. V., Fradkov, A. F., Labas, Y. A., Savitsky, A. P., Zaraisky, A. G., Markelov, M. L. & Lukyanov, S. A. (1999) *Nat Biotechnol* 17, 969-73 taking in account constraints of the protein structure. Then the DNA alignment was made following the protein alignment; excluding the poorly aligned N- and C-terminal regions. The phylogenetic tree was constructed using Tree-Puzzle software (Strimmer, K. & von Haeseler, A. (1996) *Mol. Biol. Evol.* 13, 964-969) under HKY model of DNA evolution ( Hasegawa, M., Kishino, H. & Yano, K. (1985) *J. Mol. Evol.* 22,160-174), assuming that the variability of sites follows gamma-distribution with alpha parameter estimated from the dataset. The tree was confirmed to be the maximum likelihood tree by PAML software (Yang, Z. (2000) (University College (available on the worldwide web at abacus (dot)gene(dot)ucl(dot)ac(dot)uk/software/paml(dot)html), London, England)) under REV model (Yang, Z. H., Goldman, N. & Friday, A. (1994) *Molecular Biology and Evolution* 11, 316-324). The tree built by Tree-Puzzle from protein alignment (JTT model, (Jones, D. T., Taylor, W. R. & Thornton, J. M. (1992) *CABIOS* 8, 275-282) had the same topology but lower support values due to smaller number of informative sites in the protein alignment.

III. Results and Discussion

A. Nomenclature

For the sake of clarity of phylogenetic analysis representation, in this paper we are using new nomenclature for GFP-like proteins. Our protein identification tags include four-letter leader composed of first letter of genus name and three initial letters of species name, followed by definition of color type: GFP—green, RFP—red, YFP—yellow, CP—chromoprotein (non-fluorescent). When the species is not defined, the leader is four initial letters of the genus name. In the case of multiple non-identified species of the same genus, a number is added to the leader (such as in dis3GFP or zoan2RFP); in the case of several proteins of the same color type found in the same species, the number is added to the color definition (such as in scubGFP1 and scubGFP2). For *Aequorea victoria* GFP and drFP583 from *Discosoma* sp., widely accepted common names are kept: GFP and DsRed.

B. New GFP-like proteins

Figure 2:
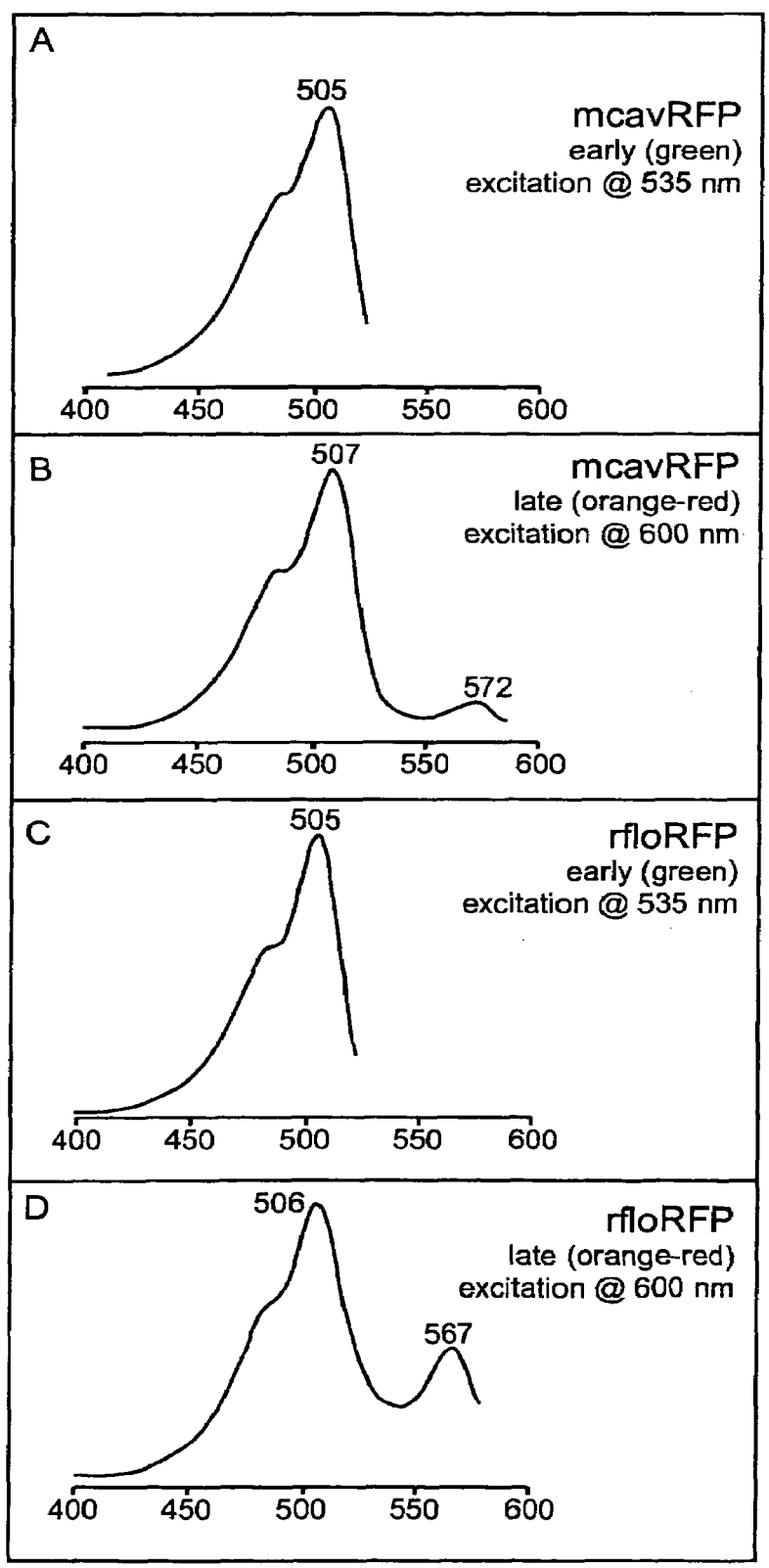
FIG. 2. Details on excitation spectra of mcavRFP (A, B) and rfloRFP (C, D). Wavelengths at which the emission was monitored are given within the graphs. A, C: excitation spectra of the green emission band in the immature protein, lacking the red emission; B, D: excitation spectra of the red emission band in more mature form. Horizontal axis is wavelength in nanometers, vertical axis is fluorescence intensity. Note that in both proteins, the major excitation peaks for immature green and mature red forms are virtually identical to each other.
Figure 3:
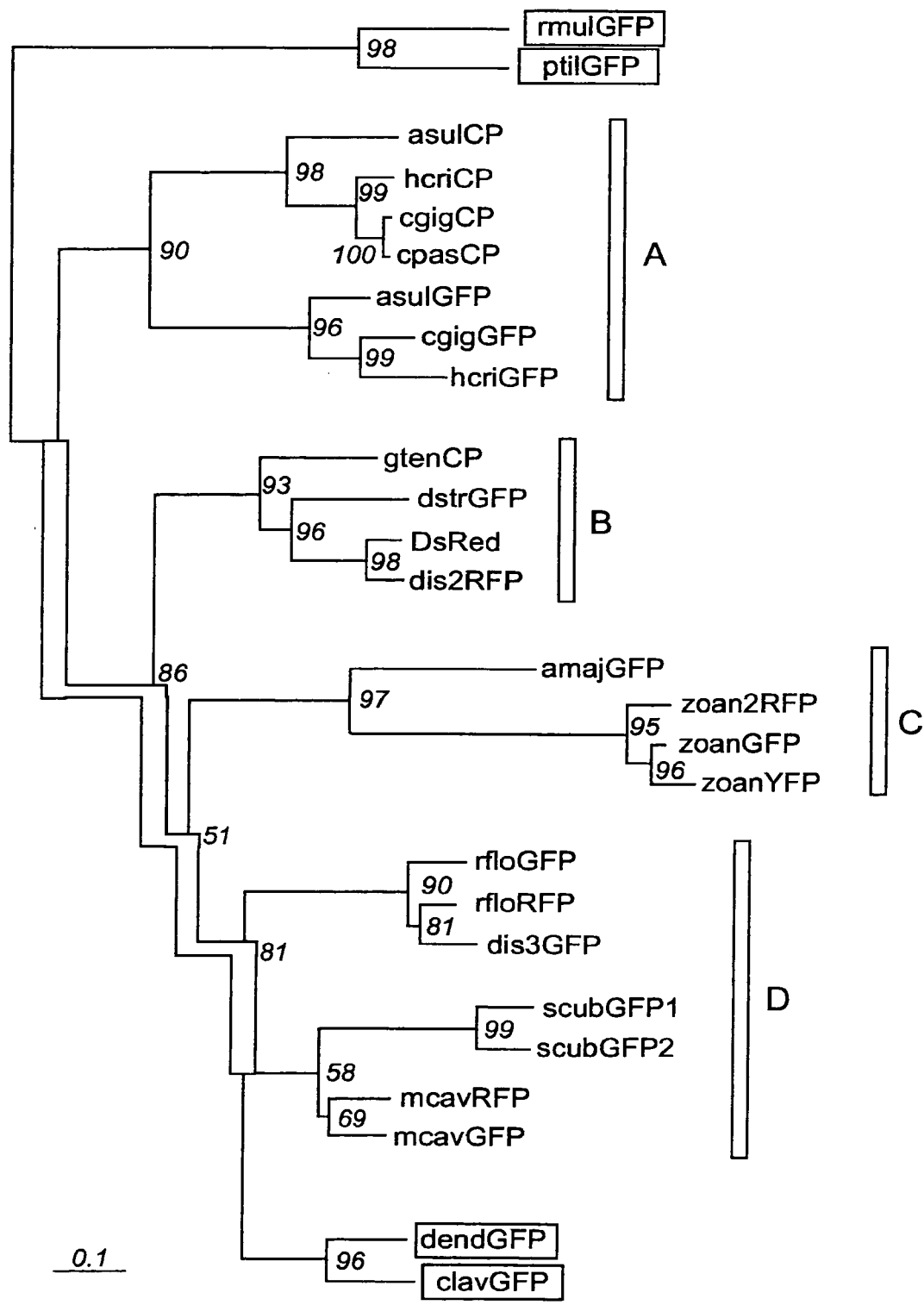
FIG. 3. The maximum-likelihood phylogenetic tree for the current dataset of anthozoan GFP-like proteins. Numbers at nodes denote the quartet-puzzling support values (1000 puzzling attempts). Proteins from Alcyonaria sub-class, which were considered outgroups, are labeled in white on black. The "stem" of the tree (thick gray line), joining two rooting groups, putatively reflects the diversity of GFP-like proteins before the separation of Alcyonaria and Zoantharia sub-classes. Gray bars marked A, B, C and D denote four distinct clades of GFP-like proteins found in Zoantharia. Scale bar: 0.1 replacements/site.
Figure 4C:
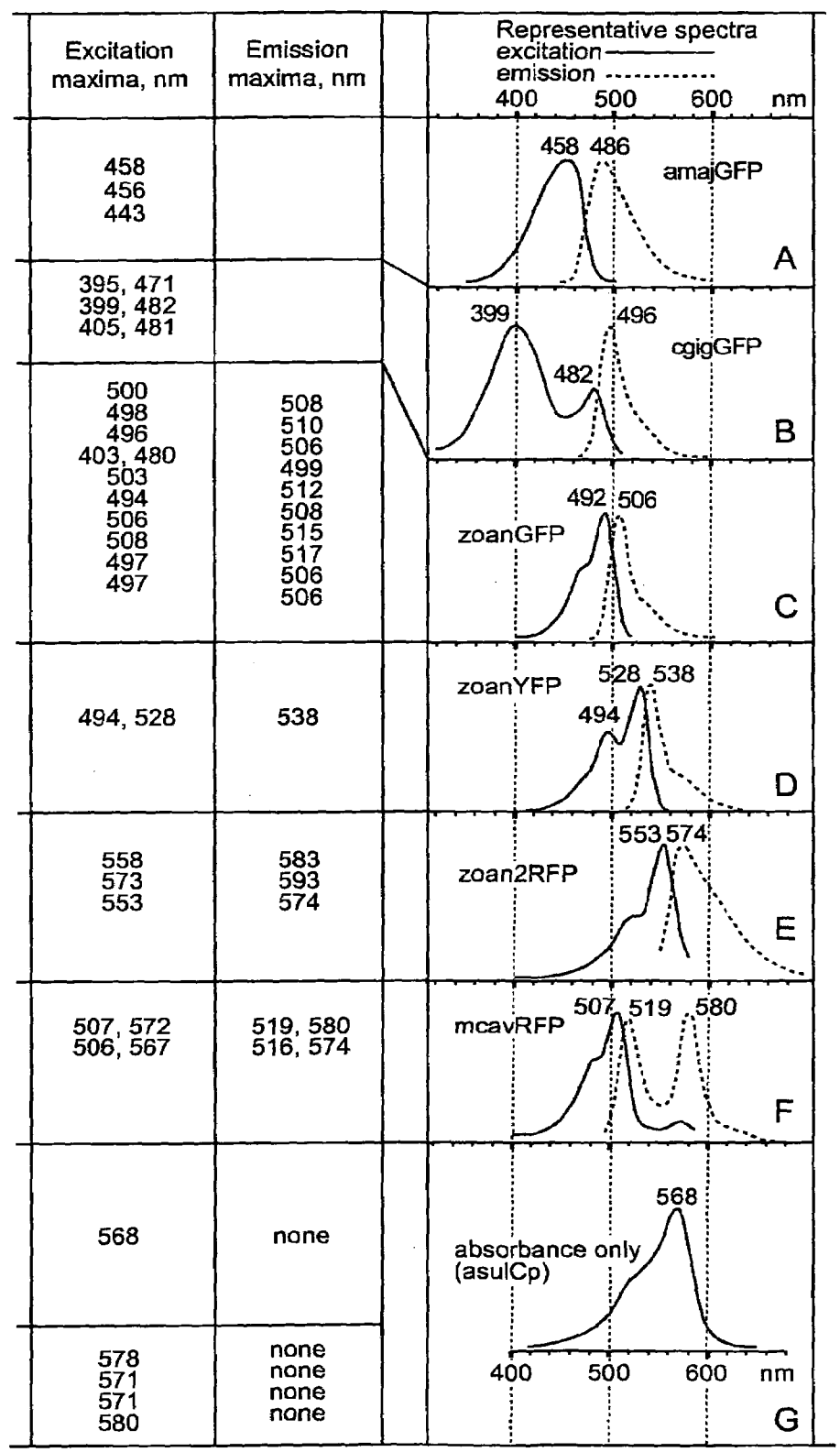
Figure 4D:
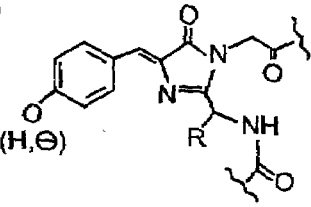
Figure 4D:
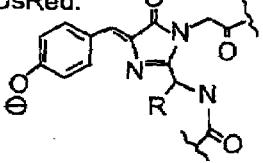
Figure 4D:
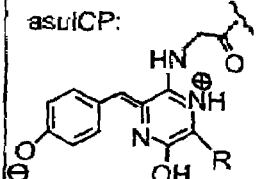
Figure 6:
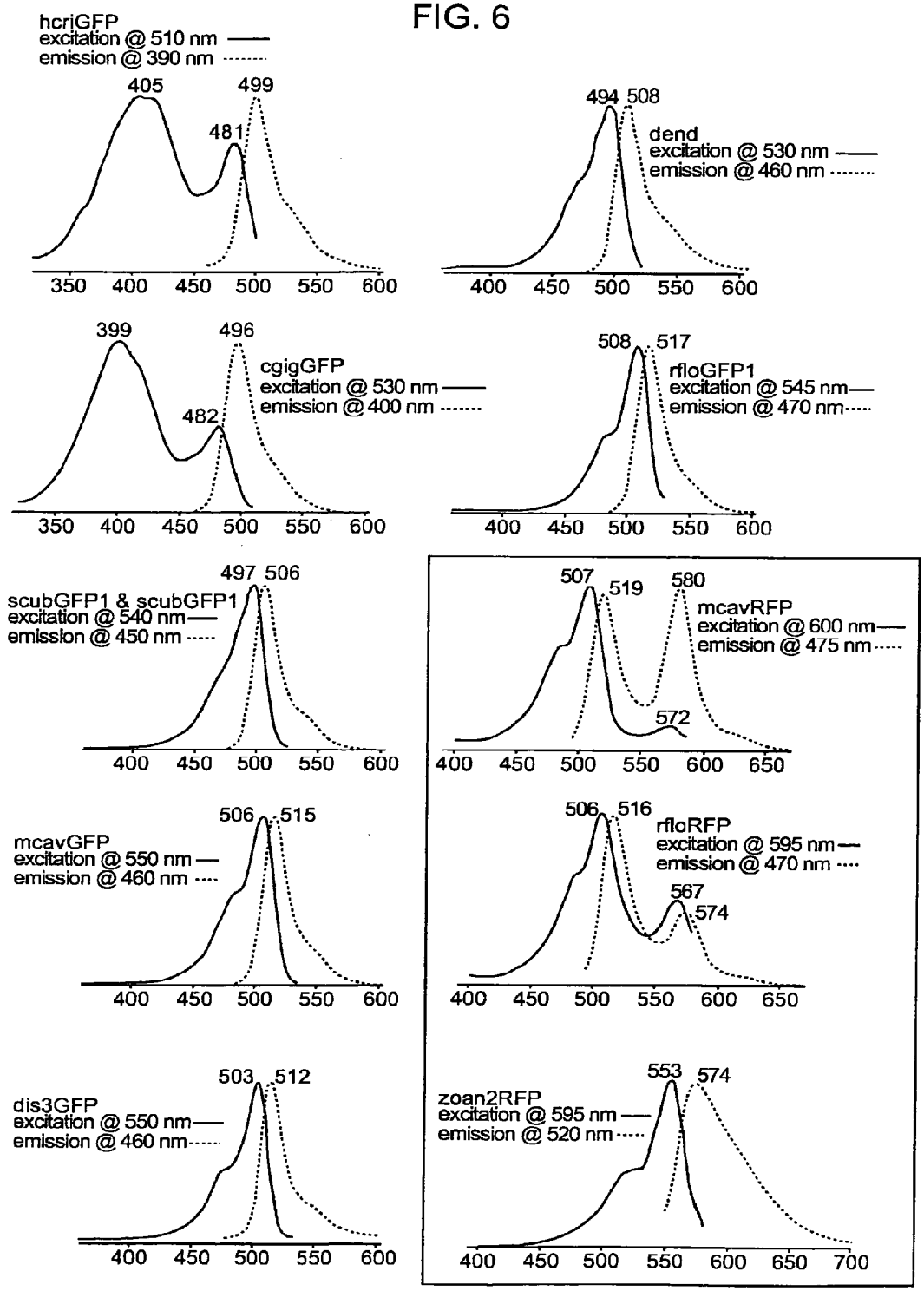
FIG. 6. Excitation (solid lines) and emission (dotted lines) spectra for the GFP-like proteins reported in this paper. The wavelengths at which the excitation or emission curves were taken are given in the legend to each graph. Horizontal axis is wavelength in nanometers, vertical axis is fluorescence intensity. The graphs for the two new orange-red proteins are boxed.

A total of fourteen new GFP-like proteins were cloned and spectroscopically characterized. The spectral features of 11 of these proteins are summarized in Table 1 appearing in the figures, as well as the other figures of the application This subset of 11 includes representatives exhibiting features not seen before in *Anthozoan* GFP-like proteins. Two green proteins from *Condylactis gigantea* (cgigGFP) and *Heteractis crispa* (hcriGFP) possess double-peaked excitation spectra very similar to the one of wild-type GFP, suggesting that their chromophores undergo photoconversion between neutral and ionized states (Brejc, K., Sixma, T. K., Kifts, P. A., Kain, S. R., Tsien, R. Y., Ormo, M. & Remington, S. J. (1997) *Proc Natl Acad Sci USA* 94, 2306-11; Palm, G. J., Zdanov, A., Gaitanaris, G. A., Stauber, R., Pavlakis, G. N. & Wlodawer, A. (1997) *Nat Struct Biol* 4, 361-5). The red-emitting protein zoan2RFP, although being very similar to DsRed in the shape of excitation/emission curves, behaves like "timer": it turns green at first and then matures into red (FIG. 1, A and B), similarly to one of the mutant variants of DsRed (Terskikh, A., Fradkov, A., Ermakova, G., Zaraisky, A., Tan, P., Kajava, A. V., Zhao, X., Lukyanov, S., Matz, M., Kim, S., Weissman, I. & Siebert, P. (2000) *Science* 290, 1585-8.). The two new red-emitters from great star coral *Montastraea cavernosa* (mcavRFP) and florida corallimorph *Ricordea florida* (rfloRFP) also show a "timer" phenotype (FIG. 1, C-F). In contrast to zoan2RFP, they failed to mature completely into red in our bacterial expression trials, which resulted in two-peak emission spectra such as shown in FIG. 1 (D and F). Remarkably, for both these proteins, the red emission band in the more mature form had major excitation peak virtually identical to the one of the immature green form, the yellow-orange excitation peak being significantly smaller (FIG. 2). This is strikingly different from the rest of the orange-red proteins, in which the red emission is excited best in yellow-orange region (FIG. 4, Table 1, spectra E). This unusual shape of excitation spectra may be due to photoconversion of the ionization states of the chromophore (by analogy with green proteins), or to even more profound differences in the chromophore structure. In favor of the latter speaks the fact that the shape of the red emission peaks of mcavRFP and rfloRFP is notably different from other orange-red proteins: it is much narrower and almost symmetrical in contrast to the wide and skewed emission peak of the others (compare spectra E and F in Table 1, FIG. 4). Meanwhile, in GFP from *Aequorea victoria*, presence or absence of photoconversion does not have much effect on the shape of emission spectra (Heim, R., Cubitt, A. B. & Tsien, R. Y. (1995) *Nature* 373, 663-4). The striking similarity of major excitation peaks for mature and immature proteins makes it tempting to suggest that in mcavRFP and rfloRFP, the "built-in" fluorescence resonance energy transfer (FRET) from immature green form of the protein to the mature red form is the major mechanism giving rise to red emission.

C. Structural/Spectral Types of GFP-Like Proteins

In our view, the best way to classify GFP-like proteins is by their color as it appears to human eye. We discriminate four color types of GFP-like proteins: green, yellow, orange-red and purple-blue, or chromoproteins (Table 1, FIG. 14). All of them share the same fold of polypeptide chain, termed "beta-can" (Ormo, M., Cubift, A. B., Kallio, K., Gross, L. A., Tsien, R. Y. & Remington, S. J. (1996) *Science* 273, 1392-5.; Yang, F., Moss, L. G. & Phillips, G. N., Jr. (1996) *Nat Biotechnol* 14, 1246-51). However, there are substantial differences between these color types as far as the chromophore structure is concerned (see Table 1). In GFP (green color), the chromophore is formed by residues 65-67 (Ser-Tyr-Gly) as a result of condensation between the carbonyl carbon of Ser-65 and the amino nitrogen of Gly-67 that produces a five-member ring, followed by the dehydrogenation of the Tyr-66 methylene bridge. All the green proteins apparently possess the same chromophore, and the differences in the spectral shapes are explained by modifications of its environment. It must be noted that the green proteins having excitation/emission spectra such as on panel A on Table 1 are sometimes called cyan or even blue, but to the human eye the color of these proteins after purification still appears bright green. In the red protein DsRed, the chromophore synthesis includes one more stage that extends the conjugated pi-system of the chromophore—dehydrogenation of the bond between the alpha carbon and amino nitrogen of the first chromophore-forming residue. Meanwhile, in the chromoproteins representative asulCP, cyclization leads to the formation of a six-member rather than five-member ring, and the critical step in creating the extended conjugated pi-system is breakage of the polypeptide chain immediately before the chromophore. Notably, no other chromoprotein contains such a chain break, as demonstrated by denaturing electrophoresis of the bacterial exprssion products (data not shown). This indicates that the chromophore structure of asulCP is exception rather than the rule within this color type. Biochemical and mutagenesis studies of the yellow zoanYFP indicated that this protein has yet another chromophore structure. So, it must be concluded that although pronounced color difference between GFP-like proteins indicates difference in chromophore structures (which makes it reasonable to use color for classification), different chromophores might be found even in the proteins of the same color, as it happens within the group of chromoproteins and probably within the orange-red group.

D. Molecular basis of color conversion

Since a chromophore synthesis pathway in DsRed is an extended form of the GFP pathway, it can be easily imagined that any mutation damaging the additional autocatalytic stage in DsRed would convert it into green protein. Indeed, at least seven different mutant variants of DsRed emitting in the green range were found during random and site specific mutagenesis. Similar reasoning should apply to the two new red proteins, because their red emission also arises as a result of further modification of the green-emitting chromophore.

It has been shown that a single amino acid replacement can convert a chromoprotein into a DsRed-like red fluorescent protein. It is particularly unexpected for asulCP from *Anemonia sulcata*, which has been directly demonstrated to contain a very dissimilar chromophore; and it still seems unlikely that its red fluorescent mutant variant actually switches to synthesizing a DsRed-type chromophore instead of original one. However, random mutations in this mutant variant resulted in appearance of green-emitting forms. Since no green-emitting intermediate stage was present in the original asulCP autocatalytic pathway, formation of green-emitting structure in these mutants signifies a substantial deviation, most probably towards a GFP/DsRed type of chromophore formation sequence judging by the shape of excitation/emission spectra of the green asulCP mutants.

Finally, yellow protein zoanYFP also can be converted into green-emitting state by at least two different amino acid replacements.

Taking these data into account, the following explanation of the observed phylogenetic pattern seems plausible: that different chromophore structures, even the most dissimilar ones, are alternative products synthesized with the help of a basically similar autocatalytic environment, rather than outcomes of prolonged evolution of different catalytic mechanisms. Apparently, just a few amino acid changes in the protein may act like a switch between alternative pathways, as exemplified by mutagenesis results on asulCP chromoprotein.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated nucleic acid present in other than its natural environment having a sequence identity of at least 95% with SEQ ID NO:17, wherein said nucleic acid encodes a chromo- or fluorescent protein.

2. The nucleic acid according to claim 1, wherein said nucleic acid comprises SEQ ID NO:17.

3. A vector comprising the nucleic acid according to claim 1.

4. An expression cassette comprising:
    (a) a transcriptional initiation region functional in an expression host;
    (b) the nucleic acid according to claim 1; and
    (c) and a transcriptional termination region functional in said expression host.

5. An isolated cell comprising the expression cassette of claim 4.

6. A kit comprising the nucleic acid according to claim 1 and instructions for using said nucleic acid.

7. The nucleic acid according to claim 1, wherein said protein has an absorbance maximum ranging from about 300 to 700 nm.

8. The nucleic acid according to claim 1, wherein said protein has an absorbance maximum ranging from about 350 to 650 nm.

9. The nucleic acid according to claim 1, wherein said protein has an absorbance maximum ranging from about 400 to 600 nm.

10. The nucleic acid according to claim 1, wherein said protein has an excitation spectrum ranging from about 300 to 700 nm and an emission spectrum ranging from about 400 to 800 nm.

* * * * *